US012678349B2

(12) United States Patent
Arora et al.

(10) Patent No.: US 12,678,349 B2
(45) **Date of Patent: *Jul. 14, 2026**

(54) FIBROUS SUBSTRATES CONTAINING FIBERS WITH FIBER ADDITIVES

(71) Applicant: The Procter & Gamble Company, Cincinnati, OH (US)

(72) Inventors: Kelyn Anne Arora, Cincinnati, OH (US); Timothy Ian Mullane, Union, KY (US); Nathan Ray Whitely, Liberty Township, OH (US); James Terry Knapmeyer, Cincinnati, OH (US); Michael Devin Long, Harrison Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 728 days.

This patent is subject to a terminal disclaimer.

(21) Appl. No.: 17/949,478

(22) Filed: Sep. 21, 2022

(65) Prior Publication Data

US 2023/0090274 A1 Mar. 23, 2023

Related U.S. Application Data

(60) Provisional application No. 63/246,911, filed on Sep. 22, 2021.

(51) Int. Cl.
*A61F 13/84* (2006.01)
*A61F 13/15* (2006.01)
(Continued)

(52) U.S. Cl.
CPC ........ *A61F 13/84* (2013.01); *A61F 13/15203* (2013.01); *A61F 13/53* (2013.01);
(Continued)

(58) Field of Classification Search
CPC ........... Y10T 428/24942; Y10T 428/29; Y10T 428/2913; Y10T 428/2915;
(Continued)

(56) References Cited

U.S. PATENT DOCUMENTS 10,182,949 B2 1/2019 Strube et al.
10,704,172 B2 7/2020 Chandrasekaran et al.
(Continued)

FOREIGN PATENT DOCUMENTS

DE 202017005952 U1 2/2018
EP 3216433 A1 9/2017
(Continued)

OTHER PUBLICATIONS

PCT Search Report and Written Opinion for PCT/US2022/076769 dated Jan. 16, 2023, 10 pages.
(Continued)

*Primary Examiner* — Maria V Ewald
*Assistant Examiner* — Ethan A. Utt
(74) *Attorney, Agent, or Firm* — Daniel S. Albrecht

(57) ABSTRACT

Patterned fibrous substrates having a plurality of individual fibers, a first region, and a second region are provided. The plurality of individual fibers comprise a functional surface additive. A plurality of individual fibers of the first region have a first diameter, and a plurality of individual fibers of the second region have a second diameter. The first diameter is less than the second diameter. The first region has a first C.I.E. L* score, and the second region has a second C.I.E. L* score. The first C.I.E. L* score is different than the second C.I.E. L* score.

22 Claims, 23 Drawing Sheets

(51) Int. Cl.

| | |
|---|---|
| ***A61F 13/53*** | (2006.01) |
| ***A61L 15/20*** | (2006.01) |
| ***A61L 15/56*** | (2006.01) |
| ***D04H 1/4291*** | (2012.01) |
| ***D04H 1/435*** | (2012.01) |
| ***D04H 1/4382*** | (2012.01) |
| ***D04H 5/06*** | (2006.01) |

(52) U.S. Cl.
CPC ............... *A61L 15/20* (2013.01); *A61L 15/56* (2013.01); *D04H 1/4291* (2013.01); *D04H 1/435* (2013.01); *D04H 1/43828* (2020.05); *D04H 5/06* (2013.01); *A61F 2013/15373* (2013.01); *A61F 2013/1556* (2013.01); *A61F 2013/530379* (2013.01); *A61F 2013/8497* (2013.01); *D10B 2401/022* (2013.01); *D10B 2509/026* (2013.01)

(58) Field of Classification Search
CPC ......... Y10T 428/2929; Y10T 428/2933; Y10T 428/2938; Y10T 428/2964; Y10T 428/24967; Y10T 442/60; Y10T 442/608; Y10T 442/637; Y10T 442/641; Y10T 442/674; B32B 5/00; B32B 5/02; B32B 5/022; B32B 5/14; B32B 5/142; B32B 27/00; B32B 27/06; B32B 27/32; B32B 33/00; B32B 2262/00; B32B 2262/02; B32B 2262/0253; B32B 2305/10; B32B 2305/20; B32B 2307/40; B32B 2307/402; B32B 2307/4206; B32B 2307/404; B32B 2307/41; B32B 2555/00; B32B 2555/02; D04H 3/00; D04H 3/005; D04H 3/007; A61F 13/00; A61F 13/15; A61F 13/45; A61F 13/49; A61F 2013/49098
USPC ....... 428/212, 364, 365, 373, 375, 392, 394, 428/397, 401; 442/327, 334, 361, 364, 442/394
See application file for complete search history.

(56) References Cited

U.S. PATENT DOCUMENTS

| | | | | |
|---|---|---|---|---|
| 2002/0170133 | A1 | 11/2002 | Mcdevitt et al. | |
| 2004/0131820 | A1 * | 7/2004 | Turner | B32B 5/12 442/337 |
| 2005/0130539 | A1 | 6/2005 | Allen et al. | |
| 2006/0058766 | A1 * | 3/2006 | Mueller | A61F 13/495 604/385.19 |
| 2010/0036347 | A1 * | 2/2010 | Hammons | A61F 13/512 604/378 |
| 2014/0343526 | A1 | 11/2014 | Knapmeyer et al. | |
| 2017/0275792 | A1 | 9/2017 | Kasahara | |
| 2018/0216269 | A1 | 8/2018 | Ashraf | |
| 2018/0318151 | A1 | 11/2018 | Bewick-Sonntag | |
| 2020/0038262 | A1 * | 2/2020 | Aviles | A61F 13/5616 |

FOREIGN PATENT DOCUMENTS

| | | | |
|---|---|---|---|
| EP | 3216435 | A1 | 9/2017 |
| WO | 2020226951 | A1 | 11/2020 |

OTHER PUBLICATIONS

All Office Actions; U.S. Appl. No. 17/949,464, filed Sep. 21, 2022.
All Office Actions; U.S. Appl. No. 17/949,488, filed Sep. 21, 2022.
Unpublished U.S. Appl. No. 17/949,464, filed Sep. 21, 2022, to Kelyn Anne Arora et al.
Unpublished U.S. Appl. No. 17/949,488, filed Sep. 21, 2022, to Kelyn Anne Arora et al.

* cited by examiner

FIBROUS SUBSTRATES CONTAINING FIBERS WITH FIBER ADDITIVES

CROSS REFERENCE TO RELATED APPLICATIONS

This application claims the benefit, under 35 U.S.C. § 119(e), of U.S. Provisional Application No. 63/246,911, filed Sep. 22, 2021, which is incorporated by reference herein in its entirety.

BACKGROUND

Fibrous substrates are useful in many industries, including the medical and hygiene industries. In these industries, fibrous substrates may be incorporated into various components of absorbent articles, such as diapers, pants, adult incontinence articles, and feminine hygiene products. Absorbent articles are often placed against the skin of a wearer for extended period of time. As such, it is desirable that the various components of the absorbent article have a soft feel against the skin. It is also desirable that the various components of the absorbent article are flexible in order to accommodate movement of the wearer. Furthermore, it is desirable for many components of absorbent articles to exhibit a high degree of absorbency. Consumers also desire absorbent articles, and the components thereof, to comprise a graphic or pattern in order to communicate information, such proper fit or placement of the article on the wearer, or to be aesthetically pleasing.

Graphics and patterns are formed on absorbent articles and components thereof using various techniques, such as deposition of inks (such as in a printing process), or embossing, especially embossing of fibrous substrate materials. Deposition of inks on an absorbent article and components thereof may be undesirable because inks disposed on outer layer components of absorbent articles may not be durable and may rub off on the skin of the wearer or on clothing or other surfaces. Creating graphics or patterns in fibrous substrate materials by embossing may be undesirable in certain instances because embossing typically results in fibers adhering to one another to create a film-like structure, leading to reduced softness, reduced flexibility, reduced absorbency, and/or reduced permeability. As such, patterned fibrous substrates and absorbent articles comprising patterned fibrous substrates should be improved.

SUMMARY

Aspects of the present disclosure may solve one or more of the problems discussed above by providing a patterned fibrous substrate comprising a plurality of individual fibers, a first region, and a second region, wherein the individual fibers of the first region and the individual fibers of the second region are substantially free of bonds other than primary bonds. The patterned fibrous substrate of the present disclosure may provide a durable graphic and/or pattern, while retaining softness, flexibility, permeability, and/or absorbency.

The present disclosure provides, in part, a patterned fibrous substrate comprising a plurality of individual fibers, a first region, and a second region. The plurality of individual fibers comprise a functional surface additive. A plurality of individual fibers of the first region have a first diameter according to the Fiber Diameter Test Method, and a plurality of individual fibers of the second region have a second diameter according to the Fiber Diameter Test Method. The first diameter is less than the second diameter. The first region has a first C.I.E. L* score, according to the Color Test Method, and the second region has a second C.I.E. L* score, according to the Color Test Method. The first C.I.E. L* score is different than the second C.I.E. L* score.

The present disclosure provides, in part, a patterned fibrous substrate comprising a plurality of individual fibers, a first region, and a second region. The plurality of individual fibers comprise a functional surface additive. A plurality of individual fibers of the first region have a first diameter according to the Fiber Diameter Test Method, and a plurality of individual fibers of the second region have a second diameter according to the Fiber Diameter Test Method. The first diameter is less than the second diameter. The first region has a first C.I.E. L* score, according to the Color Test Method, and the second region has a second C.I.E. L* score, according to the Color Test Method. The first C.I.E. L* score is different than the second C.I.E. L* score. The first region has a first region fluid permeability score (PS1), according to the Fluid Permeability Test Method, and the second region has a second region fluid permeability score (PS2), according to the Fluid Permeability Test Method. The first region fluid permeability score (PS1) is different than the second region fluid permeability score (PS2).

The present disclosure provides, in part, an absorbent article comprising a patterned fibrous substrate comprising a plurality of individual fibers, a first region, and a second region. The plurality of individual fibers comprise a functional surface additive. A plurality of individual fibers of the first region have a first diameter according to the Fiber Diameter Test Method, and a plurality of individual fibers of the second region have a second diameter according to the Fiber Diameter Test Method. The first diameter is less than the second diameter. The first region has a first C.I.E. L* score, according to the Color Test Method, and the second region has a second C.I.E. L* score, according to the Color Test Method. The first C.I.E. L* score is different than the second C.I.E. L* score.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Various non-limiting forms of the present disclosure will now be described to provide an overall understanding of the principles of the structure, function, manufacture, and use of the fibrous substrates containing fibers with fiber additives disclosed herein. One or more examples of these non-limiting forms are illustrated in the accompanying drawings. Those of ordinary skill in the art will understand that the fibrous substrates containing fibers with fiber additives described herein and illustrated in the accompanying drawings are non-limiting example forms. The features illustrated or described in connection with one non-limiting form may be combined with the features of other non-limiting forms. Such modifications and variations are intended to be included within the scope of the present disclosure.

General Description of an Absorbent Article

Figure 1:
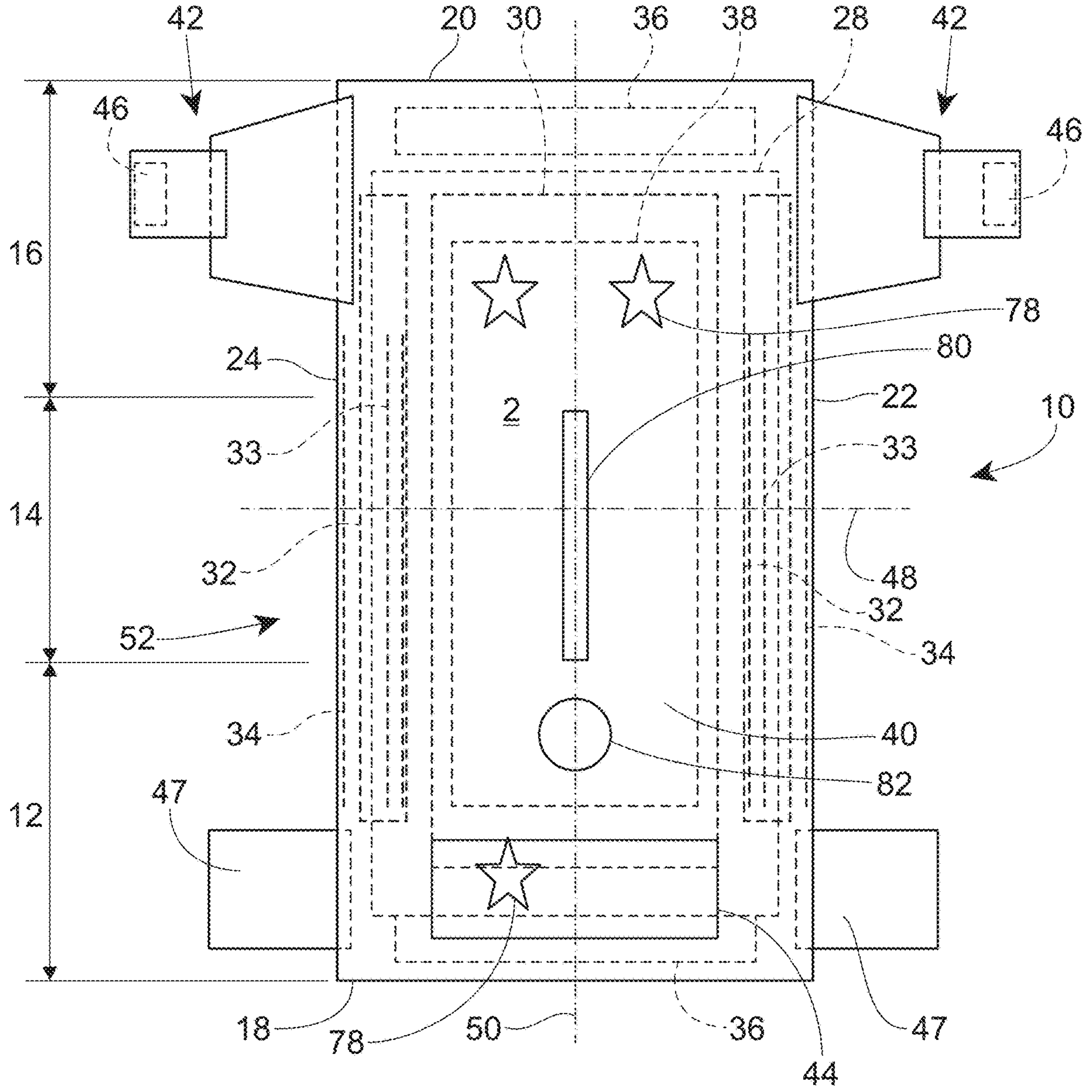
FIG. 1 is a plan view of an example absorbent article in the form of a taped diaper, garment-facing surface facing the viewer, in a flat laid-out state.
Figure 2:
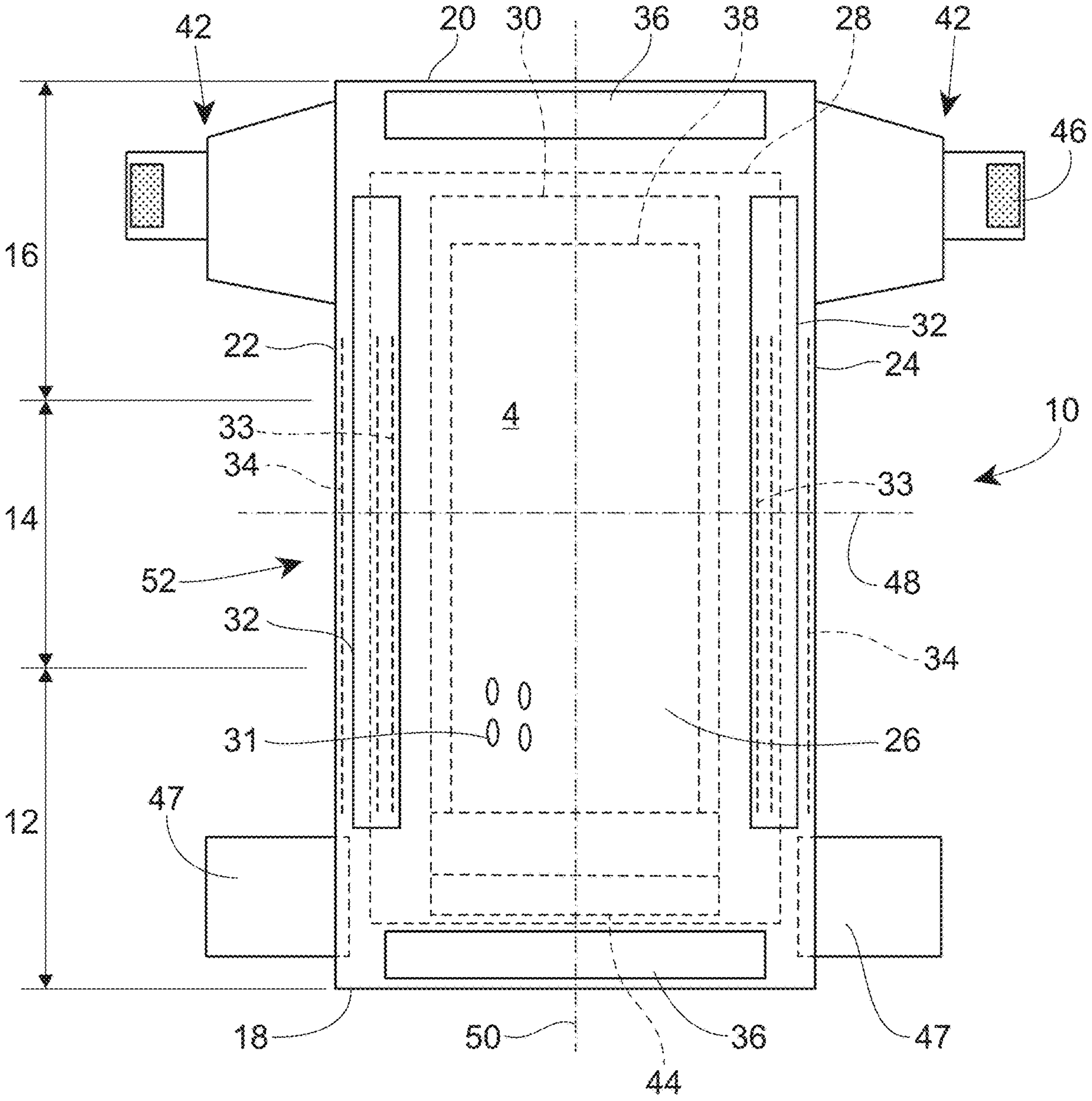
FIG. 2 is a plan view of the example absorbent article of FIG. 1, wearer-facing surface facing the viewer, in a flat laid-out state.
Figure 3:
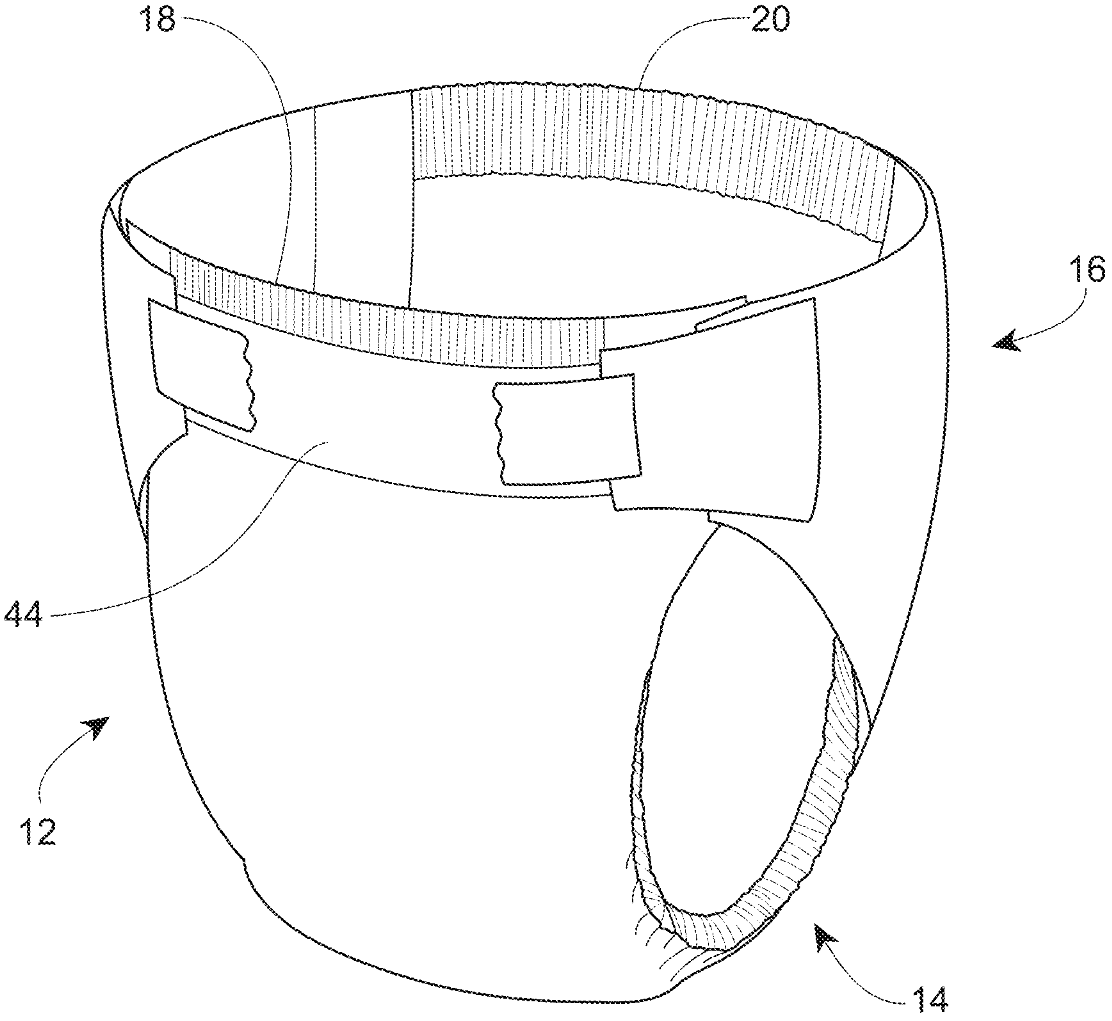
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of articles, including diapers, pants, adult incontinence products including pant- and pad style products, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
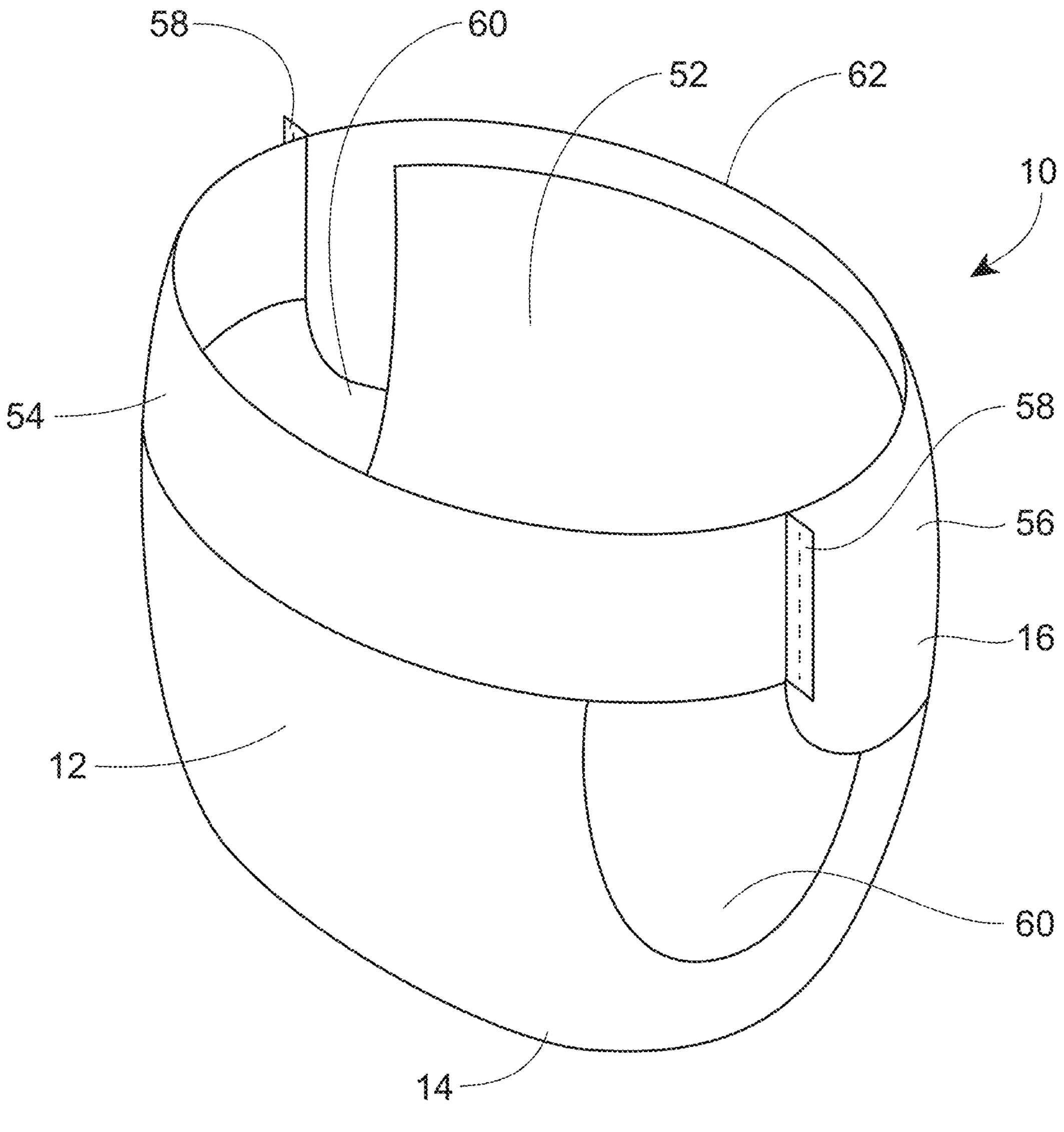
FIG. 4 is a front perspective view of an absorbent article in the form of a pant.
Figure 5:
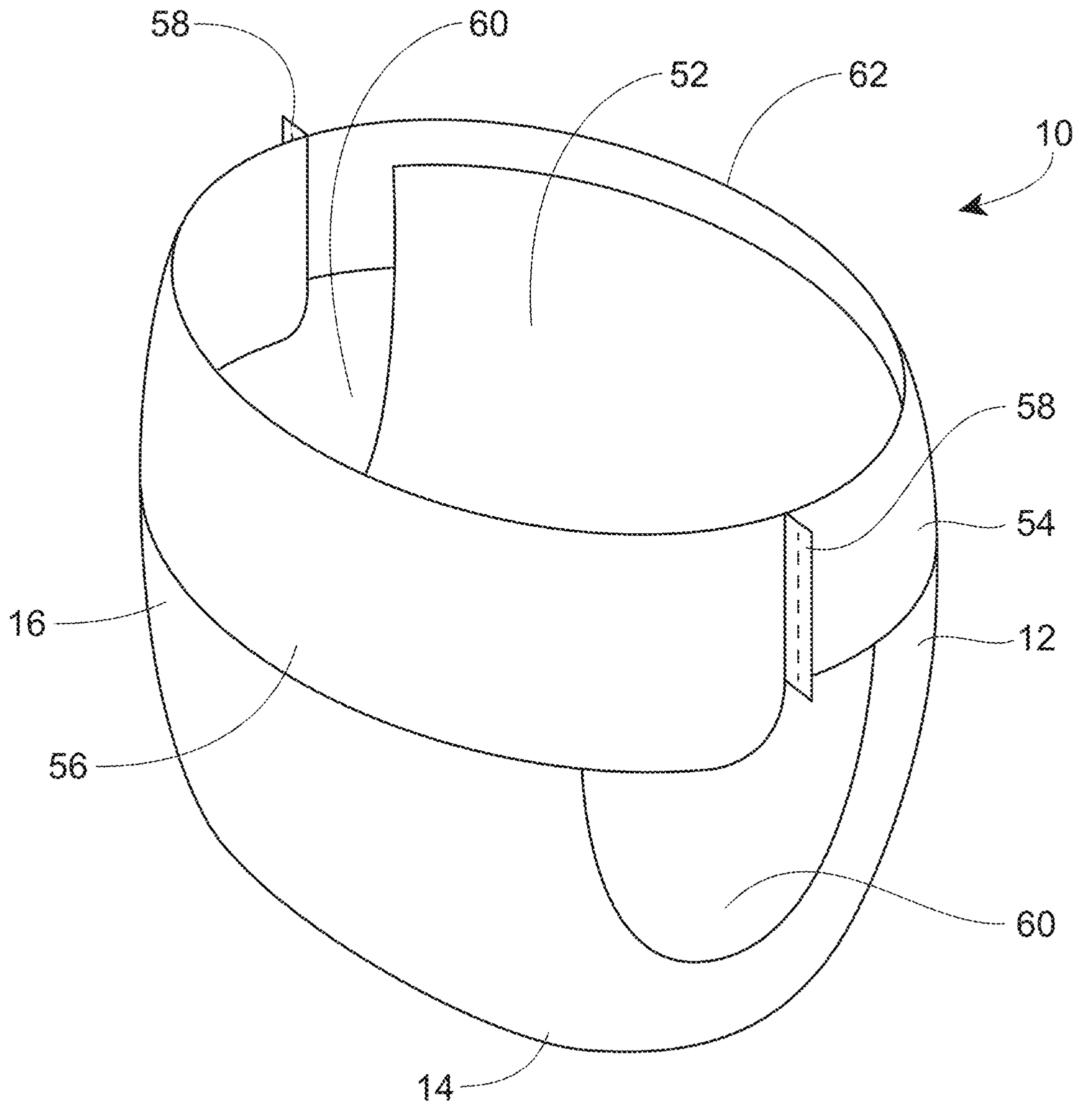
FIG. 5 is a rear perspective view of the absorbent article of FIG. 4.
Figure 6:
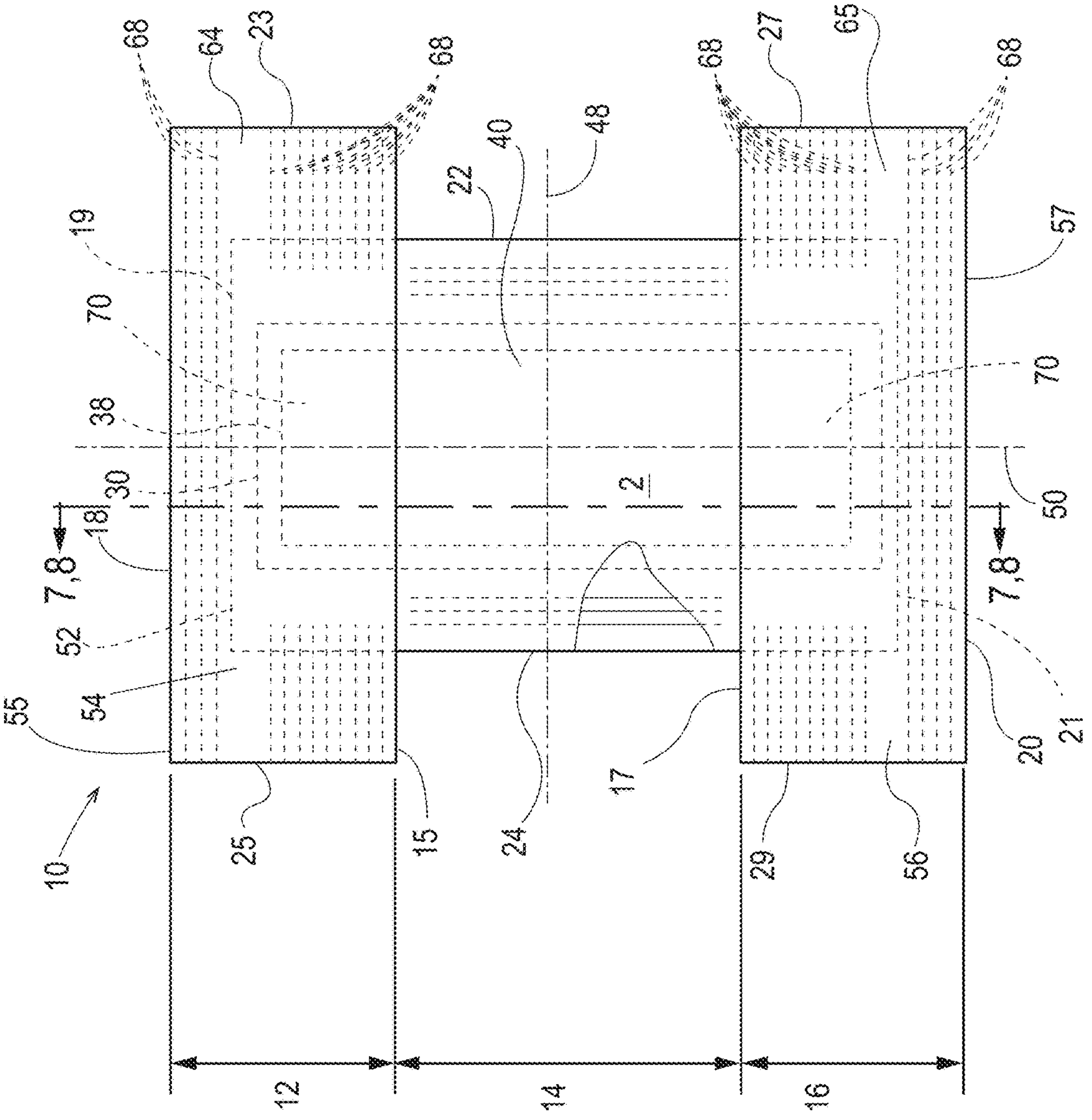
FIG. 6 is a plan view of the absorbent article of FIG. 4, laid flat, with a garment-facing surface facing the viewer.
Figure 7:
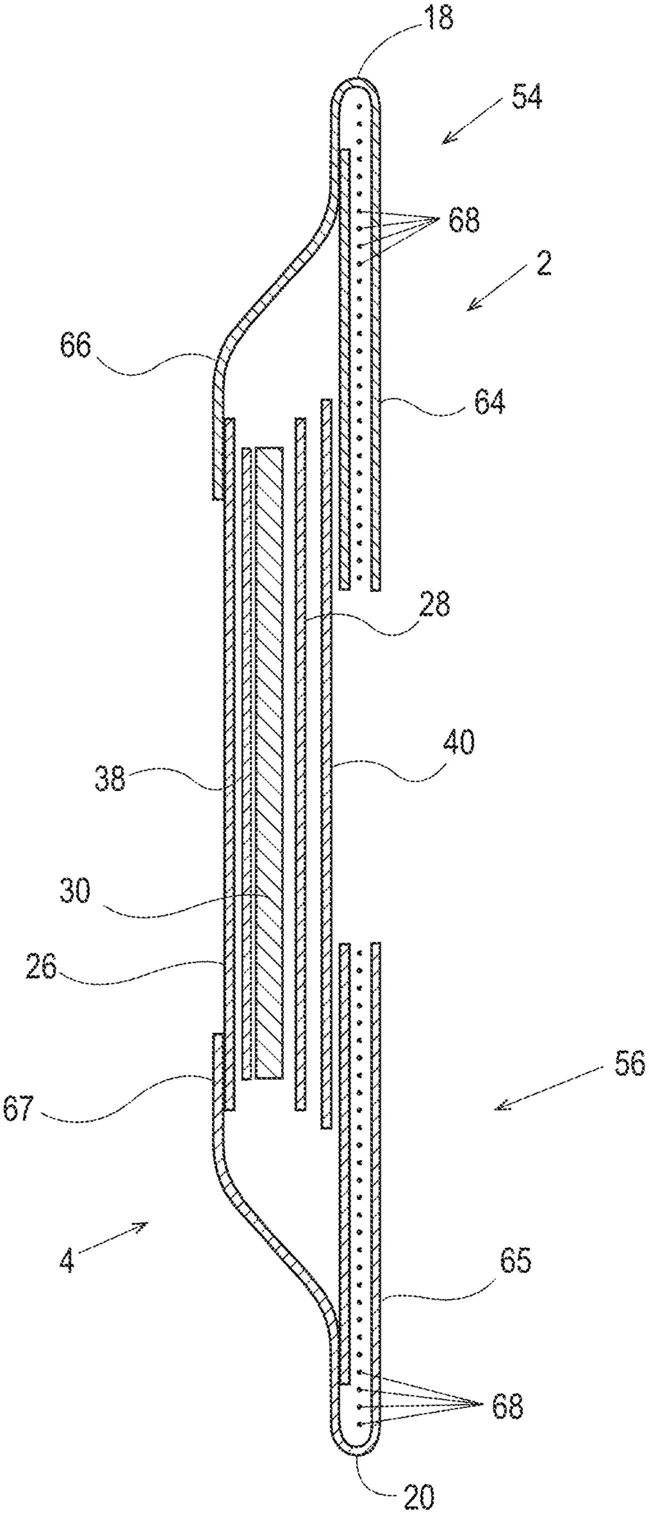
FIG. 7 is a cross-sectional view of the absorbent article taken about line 7-7 of FIG. 6.
Figure 8:
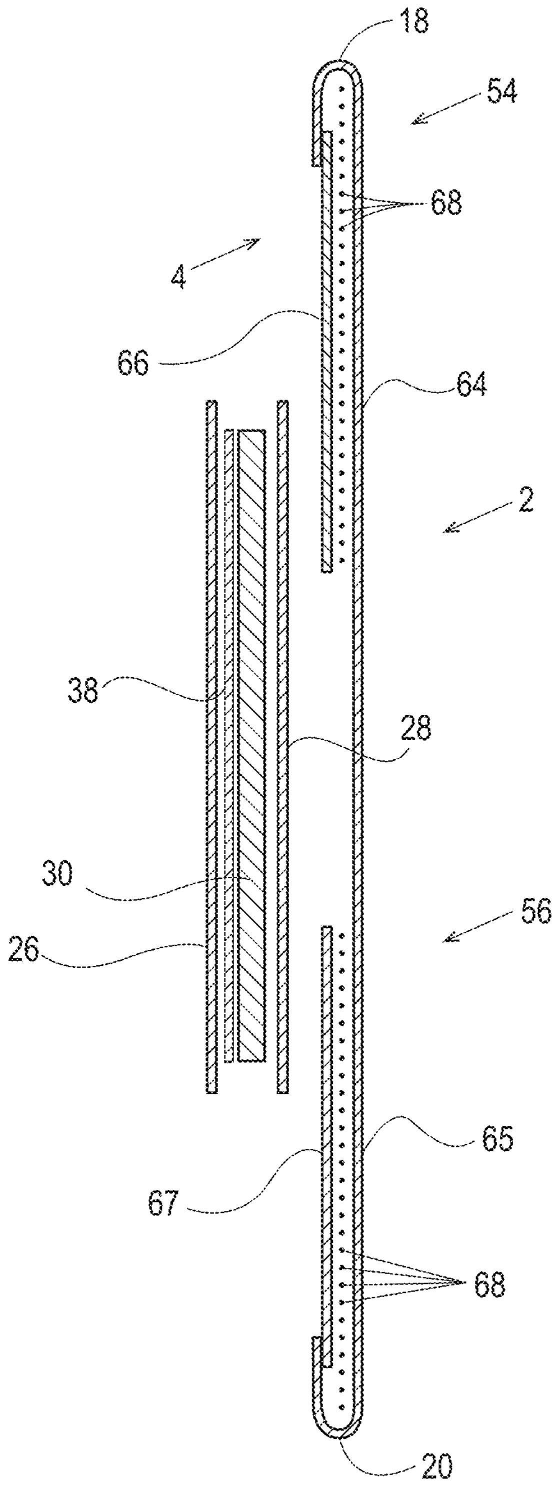
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The front belt 54 and/or the back belt 56 may comprise or be formed from the patterned fibrous substrates of the present disclosure. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

In another form, the absorbent article may be an insert for use with a reusable outer cover. The insert may be disposable or reusable. The reusable outer cover may comprise a woven or other material and may be configured as a pant or a taped diaper. In the taped context, the reusable outer cover may comprise a fastening system used to join a front waist region of the reusable outer cover to a back waist region. The fastening system may comprise snaps, buttons, and/or hooks and loops, for example. The insert may comprise a liquid permeable topsheet, a liquid impermeable backsheet, and an absorbent core positioned at least partially intermediate the topsheet and the backsheet. One or more acquisition and/or distribution materials may be positioned intermediate the topsheet and the absorbent core. The insert may comprise one or more pairs of leg cuffs and may be free of ears, side panels, and/or waistbands. In some instances, a fibrous substrate material may be positioned on a garment-facing side of the backsheet. A garment-facing surface of the insert may be attached to a wearer-facing surface of the reusable outer cover via adhesives, hook and loop fasteners, or other methods of joinder. An example insert and reusable outer cover system is disclosed in U.S. Pat. No. 9,011,402, issued on Apr. 21, 2015, to Roe et al. The insert or the reusable outer cover may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics and/or patterns (see e.g., 78 of FIG. 1). The graphics and/or patterns may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No.

9,498,389 to create a more underwear-like article. The graphics and/or patterns may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Patterned fibrous substrates of the present disclosure may be used as woven and/or nonwoven portions of the front and/or back belts in an absorbent article. The patterned fibrous substrates of the present disclosure may form a portion of, or all of, the front and/or back inner belt layers 66 and 67 and/or front and/or back outer belt layers 64 and 65, and may have an elastomeric material (e.g., strands 68 or a film (which may be apertured)) disposed at least partially therebetween.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester, polypropylene, or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The patterned fibrous substrates of the present disclosure may form portions of, or the entirety of, the topsheet in an absorbent article. The patterned fibrous substrates of the present disclosure may provide the benefits of attractive and/or functional graphics or patterns (such as, for example, placement guides) to a topsheet without the use of inks or other colorants that may rub off on the skin of a wearer, and without the use of embossing that may reduce absorbency, softness, and flexibility.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more fibrous substrate materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional features. The outer cover material 40 may be a hydroentangled nonwoven material. The patterned fibrous substrates of the present disclosure may be used as a portion of, or the entirety of, the outer cover material in an absorbent article, and may provide beneficial attractive and/or functional graphics (such as, for example, placement or fit guides) without the use of inks or other colorants that may rub off on the clothing of the wearer during use. The patterned fibrous substrates of the present disclosure may be disposed directly over a backsheet, wherein the backsheet comprises graphics (pattern, design, logo, etc.). The pattern of the patterned fibrous substrate may correspond to the backsheet graphics. The pattern of the patterned fibrous substrate may be the same as the backsheet graphics. For example, that patterned fibrous substrate may comprise a pattern of stripes, and the backsheet graphics may also be stripes. The pattern of the patterned fibrous substrate may be within the same theme as the theme of the backsheet graphics. For example, the backsheet graphics may comprise clouds, and the patterned fibrous substrate may comprise a pattern of raindrop shapes. The patterned fibrous substrate of the present disclosure may be disposed directly over a backsheet, wherein the backsheet is devoid of graphics.

Absorbent Core

Figure 9:
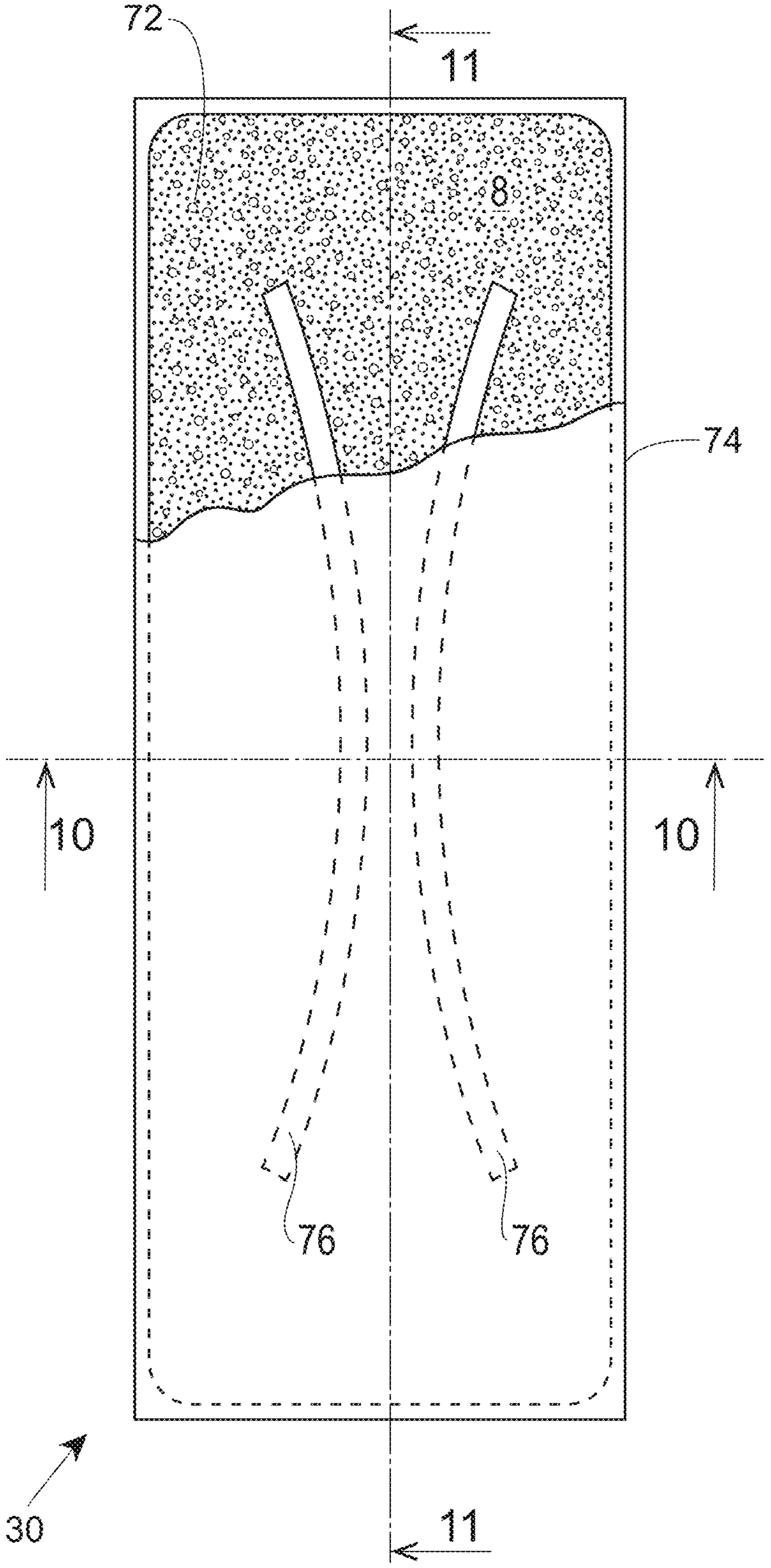
FIG. 9 is a plan view of an example absorbent core or an absorbent article.
Figure 10:
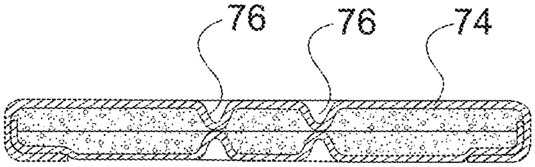
FIG. 10 is a cross-sectional view, taken about line 10-10, of the absorbent core of FIG. 9.
Figure 11:
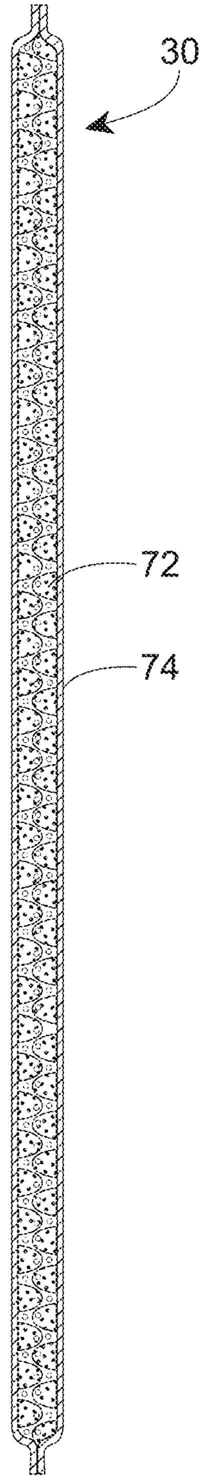
FIG. 11 is a cross-sectional view, taken about line 11-11, of the absorbent core of FIG. 10.

As used herein, the term "absorbent core" 30 refers to a component of the absorbent article 10 disposed in the article for absorbing and containing liquid such as urine received by the absorbent article. The absorbent core thus typically has a high absorbent capacity. An example absorbent core 30 is schematically shown in FIGS. 9-11. The absorbent core comprises an absorbent material 72, that is typically enclosed within or sandwiched between a core bag 74.

The core wrap may be a single material that is folded and attached to itself, or it may comprise a separate top layer and bottom layer that may be bonded or otherwise joined together. The absorbent material typically comprises superabsorbent particles which are optionally mixed with cellulose fibers. The patterned fibrous substrates of the present disclosure may form at least a portion of, or all of, the core wrap. As used herein, "absorbent core" does not include any acquisition-distribution systems, topsheet, or backsheet of the absorbent article.

The example absorbent core 30 shown in isolation in FIGS. 9-11 is in the dry state (before use). The absorbent core may typically have a generally rectangular shape as defined by its longitudinal edges and transversal front edge and back edge or may have other shapes.

Absorbent material 72 may be deposited as an absorbent layer having a generally rectangular outline, as represented in FIG. 9. A wide variety of absorbent cores may also be used. The absorbent material 72 layer may also have a non-rectangular perimeter ("shaped" core), in particular, the absorbent material 72 may define a tapering along its width towards the central region of the core (or "dog-bone" shape). In this way, the absorbent material deposition area may have a relatively narrow width in an area of the core intended to be placed in the crotch region of the absorbent article. This may provide for example better wearing comfort. Other shapes can also be used such as a "T" or "Y" or "hourglass" for the area of the absorbent material.

The absorbent material 72 may be any conventional absorbent material known in the art. For example, the absorbent material may comprise a blend of cellulose fibers and superabsorbent particles ("SAP"), typically with the percentage of SAP ranging from about 50% to about 75% by weight of the absorbent material. The absorbent material may also be free of cellulose fibers, as is known in so-called airfelt-free cores, where the absorbent material consists, or consists essentially, of SAP. The absorbent material may also be a high internal phase emulsion foam.

"Superabsorbent polymer" or "SAP" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The SAP may in particular have a CRC value of at least 20 g/g, in particular of from 20 g/g to 40 g/g. "Superabsorbent polymer particles", as used herein, refers to a superabsorbent polymer material which is in particulate form so as to be flowable in the dry state.

Various absorbent core designs comprising high amounts of SAP have been proposed in the past, see for example in U.S. Pat. No. 5,599,335 (Goldman), EP 1,447,066 (Busam), WO95/11652 (Tanzer), U.S. Pat. Appl. Pub. No. 2008/0312622 A1 (Hundorf), WO2012/052172 (Van Malderen). In particular, the SAP printing technology as disclosed in U.S. Pat. Appl. Pub. No. 2006/024433 (Blessing), U.S. Pat. Appl. Pub. No. 2008/0312617 and U.S. Pat. Appl. Pub. No. 2010/0051166 A1 (both to Hundorf et al.) may be used. The present disclosure however is not limited to a particular type of absorbent core. The absorbent core may also comprise one or more glues such as an auxiliary glue applied between the internal surface of one (or both) of the core wrap layers and the absorbent material to reduce leakage of SAP outside the core wrap. A micro-fibrous adhesive net may also be used in air-felt free cores as described in the above Hundorf references. These glues are not represented in the Figures for simplicity. Other core constructions comprising a high loft nonwoven material such as a carded nonwoven layer, having a porous structure into which SAP particles have been deposited, may also be used in present disclosure.

The absorbent material may be deposited as a continuous layer within the core wrap. The absorbent material may also be present discontinuously, for example, as individual pockets or stripes of absorbent material enclosed within the core wrap and separated from each other by material-free junction areas. A continuous layer of absorbent material, in particular of SAP, may also be obtained by combining two absorbent layers having matching discontinuous absorbent material application pattern, wherein the resulting layer is substantially continuously distributed across the absorbent particulate polymer material area, as illustrated in FIGS. 10-11. As for example taught in U.S. Pat. Appl. Pub. No. 2008/312,622 A1 (Hundorf), each absorbent material layer may thus comprise a pattern having absorbent material land areas and absorbent material-free junction areas, wherein the absorbent material land areas of the first layer correspond substantially to the absorbent material-free junction areas of the second layer and vice versa.

The basis weight (amount deposited per unit of surface) of the absorbent material may also be varied to create a profiled distribution of absorbent material, in particular in the longitudinal direction to provide more absorbency towards the center and the middle of the core, but also in the transversal direction, or both directions of the core. The absorbent core may also comprise one or more longitudinally (or otherwise) extending channels 76, which are areas of the absorbent layer substantially free of absorbent material within the absorbent material layer. The top side of the core wrap may be advantageously bonded to the bottom side of the core by adhesive, mechanical or ultra-sonic bonding through these material-free areas. Example disclosures of such channels in an airfelt-free core can be found in WO 2012/170778 (Rosati et al.) and US 2012/0312491 (Jackels). Channels may of course also be formed in absorbent cores comprising a mix of cellulose fibers and SAP particles. These channels may embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

The patterned fibrous substrates of the present disclosure may be beneficial as a portion of, or all of, the core wrap because regions of the patterned fibrous substrate with higher opacity, lower light transmission, and/or darker color (lower C.I.E. L* score) may obscure bodily exudate color, core material clumping, and/or other changes in the core due to the absorbance of bodily exudates, while exhibiting softness, flexibility, and/or absorbency.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

The patterned fibrous substrates of the present disclosure may form nonwoven portions of barrier leg cuffs in the absorbent article.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

The patterned fibrous substrates of the present disclosure may form portions of elastic waistbands in the absorbent article. An elastic waistband or waistbands may comprise a laminate, wherein the laminate comprises a patterned fibrous substrate of the present disclosure.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material. The patterned fibrous substrates of the present disclosure may for a portion of, or all of, the acquisition materials. The patterned fibrous substrate of the present disclosure may be disposed in an absorbent article such that the patterned fibrous substrate is in a face-to-face relationship with the absorbent core. The patterned fibrous substrates of the present disclosure may be beneficial as a portion of, or all of, the acquisition material because regions of the patterned fibrous substrate with higher opacity, lower light transmission, and/or darker color (lower C.I.E. L* score) may obscure bodily exudate color, core material clumping, and/or other changes in the core due to absorbance of bodily exudates, while exhibiting softness, flexibility, and/or absorbency. In addition, regions of the patterned fibrous substrate with lower opacity, higher light transmission, and/or lighter color (higher C.I.E. L* score) may permit bodily exudate coloration to be visible from the core through to the body-facing surface of the absorbent article. Furthermore, the contrast between the two regions of the patterned fibrous substrate may highlight bodily exudate deposition in the core of the absorbent article, and may be a useful and beneficial indicator to a user or caretaker of the need to change the absorbent article.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

The patterned fibrous substrates of the present disclosure may form a portion of, or all of, a landing zone area of the absorbent article.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Woven and/or nonwoven portions of the front ears and/or back ears may be formed of the patterned fibrous substrates of the present disclosure. An absorbent article of the present disclosure may comprise a landing zone area and a set of front ears and/or a set of back ears, wherein portions of, or all of the landing zone area and the front ears and/or back ears are formed of the patterned fibrous substrate of the present disclosure, such that the landing zone area comprises a pattern that coordinates with, or is the same as, the front ears and/or back ears.

Masking Layer

One or more masking layers or materials may be provided in the absorbent articles 10. A masking layer may be a layer that provides a cushiony feel when the absorbent article is touched from the garment-facing surface 2 or the wearer-facing surface 4. The masking layer may "mask" a grainy feel potentially caused by the absorbent material 72, such as superabsorbent polymers. The masking layer may "mask" bodily exudates from being visible when viewing the wearer-facing surface 4 or the garment-facing surface 2 of the absorbent article 10. The masking layer may have a basis weight in the range of about 15 gsm to about 50 gsm or about 15 gsm to about 40 gsm. The masking layer may comprise one or more nonwoven materials (e.g., a hydroentangled nonwoven material), foams, pulp layers, and/or other suitable materials. The masking layer may be the outer cover material 40. The masking layer may be the layer forming the garment-facing side or the wearer-facing side of the core bag 74. The masking layer may be a separate material positioned intermediate the garment-facing side of the core bag 74 and the liquid impermeable backsheet 28. The patterned fibrous substrates of the present disclosure may form a portion of, or all of, the masking layer. The patterned fibrous substrates of the present disclosure may be beneficial as a portion of, or all of, the masking layer because regions of the patterned fibrous substrate with higher opacity, lower light transmission, and/or darker color (lower C.I.E. L* score) may obscure bodily exudate color, core material clumping, and/or other changes in the core due to absorbance of bodily exudates, while exhibiting softness, flexibility, and/or absorbency.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g., color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate number of absorbent articles per package. By packaging the absorbent articles under compression, caregivers can easily handle and store the packages, while also providing distribution savings to manufacturers owing to the size of the packages.

Arrays

"Array" means a display of packages comprising disposable absorbent articles of different article constructions (e.g., different elastomeric materials [compositionally and/or structurally] in the side panels, side flaps and/or belts flaps, different graphic elements, different product structures, fasteners, or lack thereof). The packages may have the same brand and/or sub-brand and/or the same trademark registration and/or having been manufactured by or for a common manufacturer and the packages may be available at a common point of sale (e.g., oriented in proximity to each other in a given area of a retail store). An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Huggies," and same sub-brand, for example, "Pull-Ups." A different product in the array may have the same brand "Huggies" and the sub-brand "Little Movers." The differences between the "Pull-Ups" product of the array and the "Little Movers" product in the array may include product form, application style, different fastening designs or other structural elements intended to address the differences in physiological or psychological development. Furthermore, the packaging is distinctly different in that "Pull-Ups" is packaged in a predominately blue or pink film bag and "Little Movers" is packaged in a predominately red film bag.

Further regarding "Arrays," as another example an array may be formed by different products having different product forms manufactured by the same manufacturer, for example, "Kimberly-Clark", and bearing a common trademark registration for example, one product may have the brand name "Huggies," and sub-brand, for example, "Pull-Ups." A different product in the array may have a brand/sub-brand "Good Nites" and both are registered trademarks of The Kimberly-Clark Corporation and/or are manufactured by Kimberly-Clark. Arrays also often have the same trademarks, including trademarks of the brand, sub-brand, and/or features and/or benefits across the line-up. "On-line Array" means an "Array" distributed by a common on-line source.

Sanitary Napkin

Figure 12:
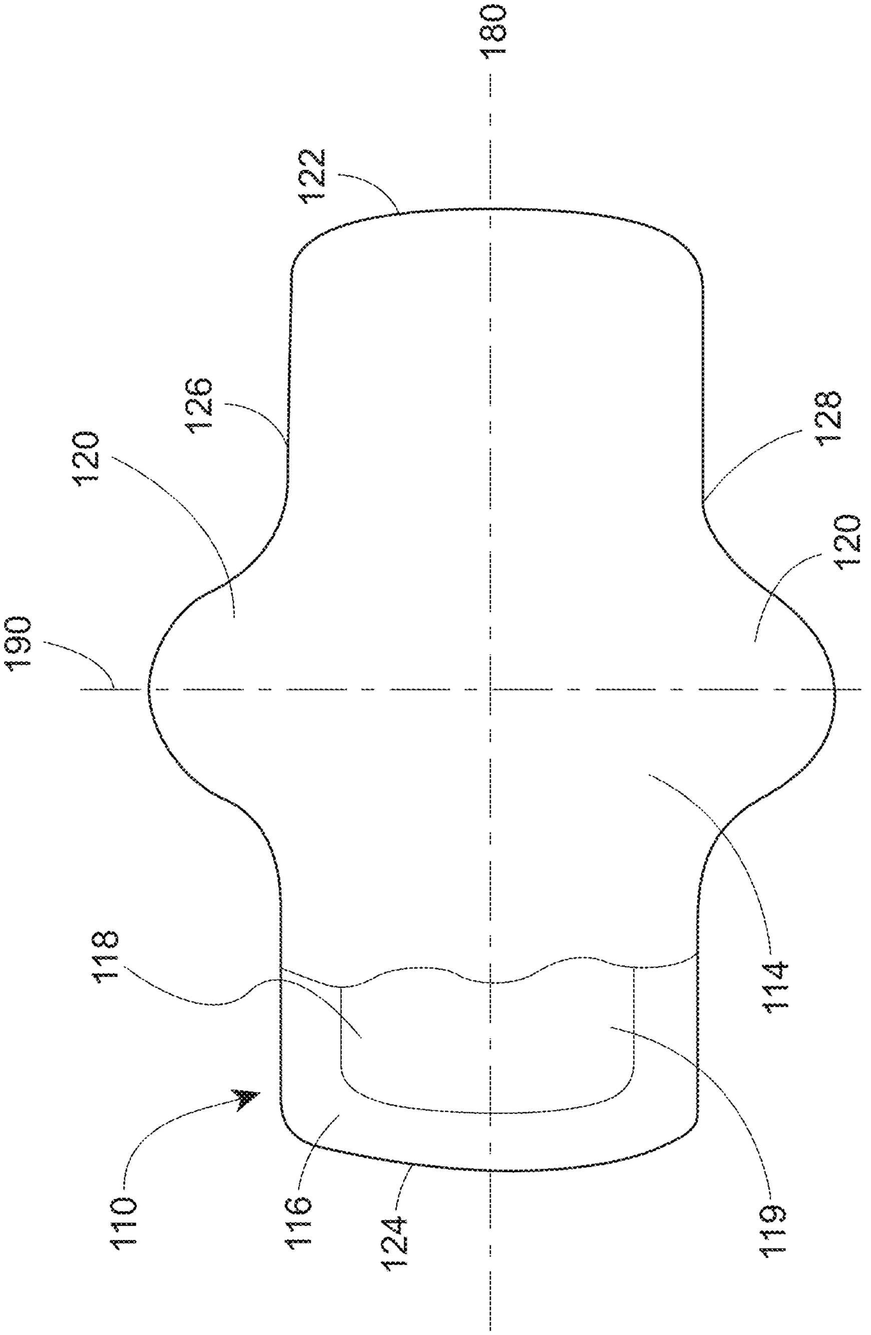
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art. The patterned fibrous substrates of the present disclosure may be used as portions of the sanitary napkin.

Patterned Fibrous Substrates

The patterned fibrous substrates of the present disclosure may comprise a plurality of individual fibers formed into a substrate, sheet, web, or bat of directionally or randomly oriented fibers. The patterned fibrous substrates may be woven or nonwoven substrates. The patterned fibrous substrates may be formed by many processes, such as meltblowing, spunbonding, solvent spinning, electrospinning, airlaying, wetlaying, weaving, and/or carding. The patterned fibrous substrate may comprise a plurality of primary bonds. "Primary bonds," as used herein, means relatively small points of consolidation of substrate fibers made during or soon after formation of the substrate and configured to hold the web structure together. Primary bonds may comprise portions of two or more individual fibers that are fused together by any known method, including heat, pressure, ultrasonic bonding, and combinations thereof. Primary bonds may be formed by any known process, including calender bonding and/or air-through bonding. The plurality of individual fibers of the fibrous substrate may additionally, or alternatively, be entangled with each other to form an entangled network of fibers, such that friction created by the entangled network of fibers holds the substrate together. The entangled network of fibers may be created by the introduction of a gas and/or liquid fluid stream through the substrate or via needling.

The patterned fibrous substrate of the present disclosure may comprise or consist of a single fiber type, or the substrate may comprise or consist of a mixture of fiber types. The plurality of individual fibers of the patterned fibrous substrate may be continuous fibers, staple length fibers, or combinations thereof. The term "continuous" within the context of fibers is distinguishable from staple length fibers in that staple length fibers are cut to a specific target length. In contrast, "continuous fibers" are not cut to a predetermined length. Instead, they can break at random lengths, but are usually longer than staple length fibers. The plurality of individual fibers may comprise natural and/or man-made (synthetic) materials. The individual fibers may comprise or consist of a single polymer component (mono-component fibers), or may comprise or consist of multi-component fibers, such as bi-component fibers. "Multi-component fibers," as used herein, means fibers comprising more than one chemical polymer species or material. The fibers may comprise petroleum sourced resins, recycled resins, and/or bio-sourced resins, such as polylactic acid, polyethylene and/or polypropylene, and polybutylene terephthalate. The fibers may comprise or consist of recycled polypropylene and/or recycled polyester. The fibers may have round, triangular, tri-lobal, or otherwise shaped cross-sections, for example. Often, the different polymer components have different melting temperatures, viscosities, glass transition temperatures, crystallinities, and/or crystallization rates. The multi-component fibers, such as bi-component fibers, may comprise sheath/core, side-by-side, islands in the sea, and/or eccentric configurations or may have other configurations. In the context of bi-component fibers, fibers comprising a core/sheath configuration may be comprised of a first polymer forming the core of the fiber, and a second polymer partially or completely surrounding the first polymer and forming the sheath of the fiber. The patterned fibrous substrates of the present disclosure may be free of pulp.

The patterned fibrous substrates of the present disclosure may comprise or consist of a plurality of individual fibers, wherein the individual fibers comprise or consist of mono-component polypropylene fibers. While mono-component fibers may consist of a single polymer component, such as polypropylene, they may also include additives, pigments, and the like. The patterned fibrous substrates of the present disclosure may comprise or consist of a plurality of individual fibers, wherein the individual fibers comprise or consist of bi-component fibers comprising a first component and a second component, wherein the first component is polyethylene, and the second component is polypropylene or polyester. The plurality of individual fibers may comprise or consist of bi-component fibers having a sheath/core structure, wherein the sheath of the fibers comprises polyethylene, and wherein the core of the fibers comprises polypropylene or polyester.

The patterned fibrous substrates of the present disclosure may comprise crimped fibers. Crimped fibers may result when the different polymer components of multi-component fibers have different melting temperatures, viscosities, glass transition temperatures, crystallinities, and/or crystallization rates, and are disposed in an eccentric sheath/core or side-by-side configuration within the fibers. As the multi-component fibers cool after formation, a first polymer component may solidify and/or shrink at a faster rate than a second polymer component while the second polymer component may have sufficient rigidity to resist compression along a longitudinal fiber axis. The continuous fibers may deform and curl up when strain on the fiber is relieved, thereby causing what is known as "crimp" in the fibers. Crimp of the fibers aids in the softness and loft of a fibrous substrate, which is consumer desirable. The patterned fibrous substrates of the present disclosure may comprise or consist of crimped bi-component fibers, wherein the sheath of the fibers comprises polyethylene, and wherein the core of the fibers comprises polyester. The crimped bi-component fibers may be carded prior to incorporation into the patterned fibrous substrate.

The plurality of individual fibers of the patterned fibrous substrates of the present disclosure may comprise a functional surface additive or a mixture of functional surface additives. The functional surface additive or mixture of functional surface additives may be incorporated into the plurality of individual fibers as a melt additive or as a topical additive.

A melt additive is a functional surface additive that may be added directly to the fibers or as a master batch to the polymer melt during spinning of the fibers. The melt additive may then bloom to the surface of the fibers and creates a film covering a portion of the external surface of the fiber and/or can create fibrils, flakes, particles, droplets, and/or other surface features. For those fibers comprising fibrils, the fibrils may extend outwardly, or radially outwardly, from the surface of the fibers.

While the fibrils extend outwardly from surfaces of individual fibers, the fibrils may also extend to or from (i.e., contact) other fibers within the same layer or a different layer of a nonwoven web and/or to fibrils extending from fibers within the same layer or a different layer of the nonwoven laminate. A similar effect may be obtained for additives which are applied to the fibers post production (topical additive), discussed further below. Without wishing to be bound by theory, it is believed that the additive, regardless of whether a melt additive or a topical additive added post fiber production, changes the surface energy of the constituent fibers and inhibits the ability for fibers to fuse or otherwise consolidate.

Functional surface additives may include fatty amides, mono-, di-, and triglycerides, silicones and copolymers thereof, fatty acids, petroleum-based waxes and oils, and hydrocarbons, including but not limited to aminosiloxanes (also known as aminosilicones or aminodimethicones), cationic siloxanes (such as SILASTOL PHP26 from SCHILL+SEILACHER GmbH, Boeblingen, Germany), glyceryl tristearate, erucamide, oleamide, and other lubricants, surfactants, and fiber finishing agents.

Further suitable functional surface additives include fatty alcohols and fatty acid esters. Non-limiting examples of suitable fatty alcohols having from about 12 to about 24 carbon atoms include saturated, un-substituted, monohydric alcohols or combinations thereof, which have a melting point less than about 110° C., preferably from about 45° C. to about 110° C. Specific examples of fatty alcohol carriers for use in present disclosure include, but are not limited to, cetyl alcohol, stearyl alcohol, cetearyl alcohol, behenyl alcohol, arachidyl alcohol, lignocaryl alcohol, and combinations thereof. Non-limiting examples of suitable fatty acid esters include those fatty acid esters derived from a mixture of C12-C28 fatty acids and short chain (C1-C8, preferably C1-C3) monohydric alcohols preferably from a mixture of C16-C24 saturated fatty acids and short chain (C1-C8, preferably C1-C3) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols (C12-C28, preferably C12-C16) and shorter chain fatty acids such as lactic acid, specific examples of which include lauryl lactate and cetyl lactate. Suitable fatty acid esters may further include an ester formed from an alcohol with two or more hydroxyl groups and one or more fatty acids having between at least 12 carbon atoms to 22 carbon atoms, or at least 14 carbon atoms, whereby within one ester compound different fatty acid-derived groups may be present. The fatty acid ester compound may be an ester of an alcohol carrying two or more, or three or more, functional hydroxyl groups per alcohol molecule, whereby all of the hydroxyl groups form an ester bond with fatty acids (either the fatty acid or mixtures thereof).

In some forms, the alcohol may have three functional hydroxyl groups. It is understood that in a fatty acid ester having more than one ester bond, such as in di- or triglycerides, the fatty acid-derived group may be the same, or they may be two or even three different fatty acids-derived groups. It is further understood that the additive component may comprise a mixture of mono- di- and/or tri-fatty acid ester (e.g., mono- di-, and/or triglyceride) esters with the same fatty-acid derived group per molecule, and/or with different fatty acid-derived groups without exceeding the scope of the invention. Preferred fatty acids in at least one embodiment may range from a C8 fatty acid to a C30 fatty acid; or from a C12 fatty acid to a C22 fatty acid. Suitable vegetable fatty acids typically include unsaturated fatty acids. The fatty acid may suitably be selected from the group comprising arachidic acid, stearic acid, palmitic acid, myristic acid, myristoleic acid, oleic acid, linoleic acid, linolenic acid, and arachidonic acid. In another further embodiment, a substantially saturated fatty acid is preferred, particularly when saturation arises as a result of hydrogenation of fatty acid precursor. The fatty acids may range from a C12 fatty acid to a C22 fatty acid as illustrated in [1],

[1]

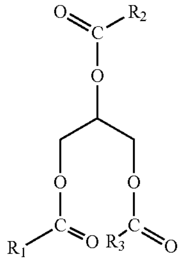

where R1, R2, and R3 each have a number of carbon atoms ranging from 11 to 21. In at least one other embodiment, the fatty acids may range from a C16 fatty acid to a C20 fatty acid.

In some forms, a substantially saturated fatty acid is preferred, particularly when saturation arises as a result of hydrogenation of fatty acid precursor. In at least one further form, a C18 fatty acid, stearic acid, is preferred. An example of the stearic acid-substituted fatty acid is [2-octadecanoyloxy-1-(octadecanoyloxymethyl)ethyl]octadecanoate having a CAS registry number of 555-43-1. It should be understood that the preferred triglyceride ester has an esterified glycerol backbone having no non-hydrogen substituents on the glycerol backbone.

In some forms, the one or more additives may comprise a mono- and/or di-glyceride ester, and/or a triglyceride ester, (with one, two or three fatty acid-derived groups). It should be understood that while [1] illustrates a simple triglyceride in which all three pendent fatty acids may be the same, other embodiments may include a mixed triglyceride in which two or even three different pendent fatty acids are present without exceeding the scope of the invention. It should be further understood that while the triglyceride ester is illustrated in [1] is a single triglyceride ester formulation, the triglyceride ester used in the preparation of the master batch may include a plurality of triglyceride esters having different pendent fatty acid groups and/or one or more derivatives of the fatty acid, without exceeding the scope of the invention. It should be further understood that while the triglyceride ester illustrated in [1] is a monomer, the triglyceride ester used in the preparation of the master batch may include a polymerized triglyceride ester, such as a polymerized, saturated glyceride ester without exceeding the scope of the invention. It should be further understood that the polymerized triglyceride ester may comprise a mixture of polymers having different numbers of monomeric units included in the polymer. For example, the polymerized triglyceride ester may include a mixture of monoesters, diesters, and the like.

The fatty acids used to form the ester compounds include fatty acid derivatives for the purpose of the present disclosure. A mono-fatty acid ester, or for example, a monoglyceride, comprises a single fatty acid, e.g., connected a glycerol; a di-fatty acid ester, or e.g., di-glyceride, comprises two fatty acids, e.g., connected to the glycerol; a tri-fatty acid ester, or e.g., triglyceride, comprises three fatty acids, e.g., connected to a glycerol. In an embodiment, the additive may comprise at least a triglyceride ester of fatty acids (i.e., the same or different fatty acids).

It should be understood that the triglyceride ester may have an esterified glycerol backbone having no nonhydrogen substituents on the glycerol backbone; however, the glycerol backbone may also comprise other substituents. In some forms, the glycerol backbone of the glycerol ester may only comprise hydrogen. The glyceride esters may also comprise polymerized (e.g., tri) glyceride esters, such as a polymerized, saturated glyceride esters.

In a fatty acid ester having more than one ester bond, such as in di- or tri-glycerides, the fatty acid-derived group may be the same, or they may be two or even three different fatty acids-derived groups.

The additive may comprise a mixture of mono-, di-, and/or tri-fatty acid ester (e.g., mono-di- and/or triglyceride) esters with the same fatty-acid derived group per molecule, and/or with different fatty acid-derived groups.

The fatty acids may originate from vegetable, animal, and/or synthetic sources. Some fatty acids may range from a C8 fatty acid to a C30 fatty acid, or from a C12 fatty acid to a C22 fatty acid. Suitable vegetable fatty acids typically include unsaturated fatty acids such as oleic acid, palmitic acid, linoleic acid, and linolenic acid. The fatty acid may be arachidic, stearic, palmitic, myristic, myristoleic, oleic, linoleic, linolenic, and/or arachidonic acid.

In some forms, a substantially saturated fatty acid may be used, particularly when saturation arises as a result of hydrogenation of fatty acid precursor. In an embodiment, a C18 fatty acid, or octadecanoic acid, or more commonly called stearic acid, may be used to form an ester bond of the fatty acid ester herein. Stearic acid may be derived from animal fat and oils as well as some vegetable oils. The stearic acid may also be prepared by hydrogenation of vegetable oils, such as cottonseed oil. The fatty acid ester herein may comprise fatty acids of mixed hydrogenated vegetable oil, such as one having CAS registration number 68334-28-1.

The functional surface additive of the present disclosure may comprise or consist of glyceryl tristearate. In an embodiment, the additive may comprise a glycerol tristearate (CAS No. 555-43-1), also known by such names as tristearin or 1,2,3-Trioctadecanoylglycerol. (In the following, the name glycerol tristearate will be used, and in case of doubt the CAS No. shall be seen as the primary identifier).

In some forms, additives with chemical structures similar to glycerol tristearate or tristearin such as triacylglycerols (triglycerides) including but not limited to trimyristin, tripalmitin, trilaurin, trimargarine, and waxes such as distearin, and mixtures of saturated and unsaturated glycerides, such as 1,3-distearoyl-2-oleoylglycerol (SOS) may be utilized. Non-limiting examples additives having molecular and crystallite structures as similar to tristearin include Alkylketene dimers (AKD), inorganic and organic salts of fatty acids (also known as alkyl carboxylic acids) that comprise of alkyl chains that are mostly saturated and contain between 12 and 22 carbon atoms. Non-limiting examples of salts of fatty acids include zinc stearate, calcium stearate, magnesium stearate, titanium stearate, silver stearate, aluminum di- and tri-stearates, aluminum tripalmitate, aluminum trimyristate, aluminum trilaurate, sorbitan tristearate, sorbitan tripalmitate, sorbitan trimyristate, sorbitan trilaurate, and combinations thereof, which are believed to form flaky and fibrillar lamellar structures on surfaces due to blooming.

In some forms, the fatty acid ester of the functional surface additive may have a number-averaged molecular weight ranging from 500 to 2000, from 650 to 1200, or from 750 to 1000, specifically reciting all whole integer increments within the above-specified ranges and any ranges formed therein or thereby.

The functional surface additive may comprise very little or no halogen atoms; for example, the additive may comprise less than 5 wt. % halogen atoms (by weight of the additive), or less than 1 wt. %, or less than 0.1 wt. % of the functional surface additive. The functional surface additive may be substantially halogen-free.

In some forms, the functional surface additive may be or may comprise a lipid ester or glycerol tristearate. In various forms, the fibrils may comprise, consist of, or consist essentially of (i.e., 51% to 100%, 51% to 99%, 60% to 99%, 70% to 95%, 75% to 95%, 80% to 95%, specifically including all 0.1% increments within the specified ranges and all ranges formed therein or thereby) of the additive.

Nonlimiting examples of suitable alkyl ethoxylates include C12-C22 fatty alcohol ethoxylates having an average degree of ethoxylation of from about 2 to about 30. Non-limiting examples of suitable lower alcohols having from about 1 to about 6 carbon atoms include ethanol, isopropanol, butanediol, 1,2,4-butanetriol, 1,2 hexanediol, ether propanol, and mixtures thereof. Non-limiting examples of suitable low molecular weight glycols and polyols include ethylene glycol, polyethylene glycol (e.g., Molecular Weight 200-600 g/mole), butylene glycol, propylene glycol, polypropylene glycol (e.g., Molecular Weight 425-2025 g/mole), and mixtures thereof.

For those forms where the functional surface additive is provided as a melt additive, e.g., part of the master batch, the functional surface additive may be between 0.25 weight percent to about 20 weight percent of the fiber formulation, or between about 0.5 weight percent and about 10 weight percent, or between about 0.5 weight percent and about 5 weight percent, specifically reciting all values within these ranges and any range formed therein or thereby. For those forms where bi-component fibers are utilized, the functional surface additive may be present at the same level in each of the constituents of the bi-component fiber, may be at different levels with regard to the constituents of the bi-component fiber, or may be preset in one constituent but not the other of a bi-component fiber.

The functional surface additive may be applied to the fibers of the patterned fibrous substrates of the present disclosure as a topical additive by any suitable process. Some examples include spraying, slot coating, kiss coating, or the like. The functional surface additive may be applied at about 0.25 weight percent to about 20 weight percent of the substrate, or between about 0.5 weight percent and about 10 weight percent, or between about 0.5 weight percent and about 5 weight percent, specifically reciting all values within these ranges and any range formed therein or thereby. The functional surface additive may be blended with other topical ingredients, for example in a lotion composition.

The plurality of fibers of the patterned fibrous substrate of the present disclosure may comprise pigment, colorant, and/or dye. In the case of multi-component fibers, the pigment, colorant, and/or dye may be disposed in only one component, or the pigment may be found in more than one component of the fibers. The pigment, colorant, and/or dye may be disposed in the core of a core/sheath multi-component fiber configuration. The pigment, colorant, and/or dye may be disposed in the sheath of a core/sheath multi-component fiber configuration. The pigment may be titanium dioxide. The plurality of fibers of the patterned fibrous substrate of the present disclosure may be devoid of pigment, colorant, and/or dye.

Figure 13:
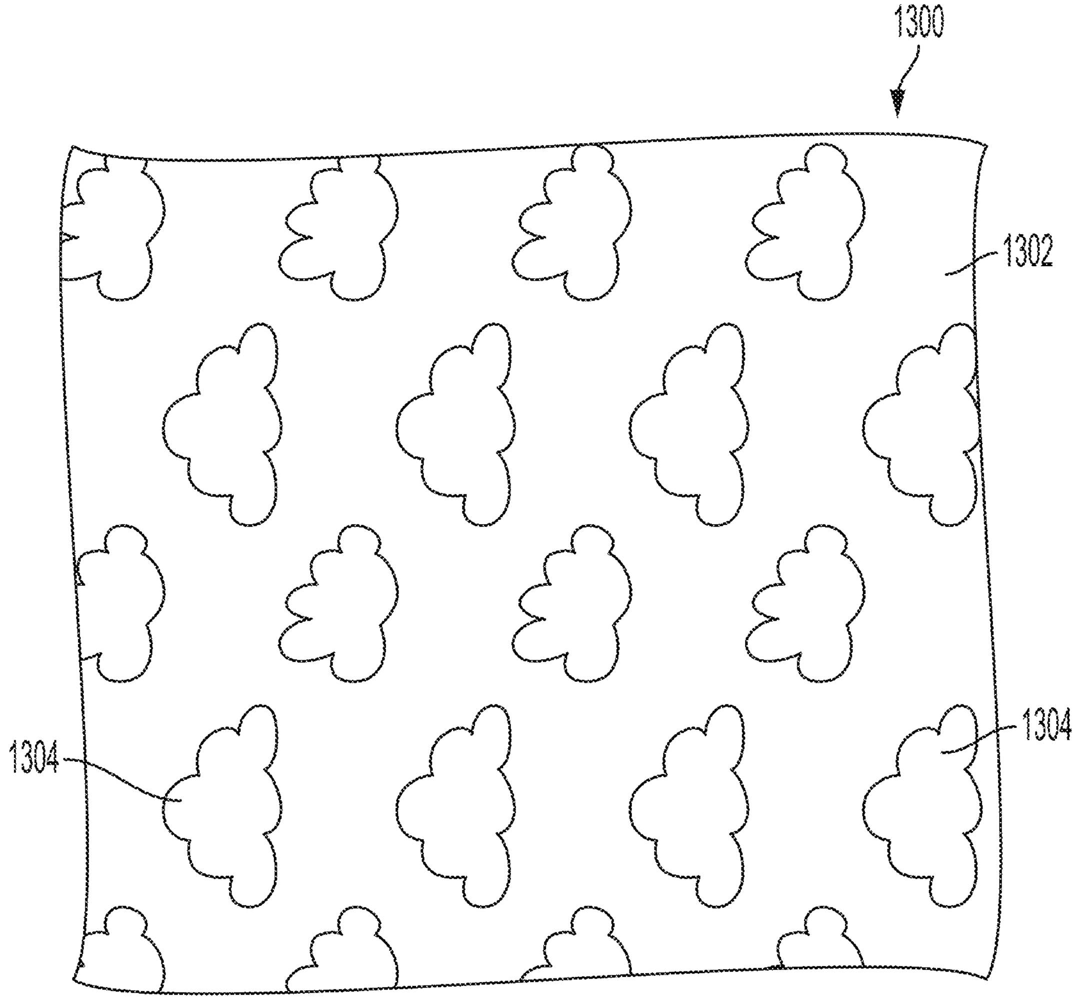
FIG. 13 is an image of a patterned fibrous substrate of the present disclosure.
Figure 14:
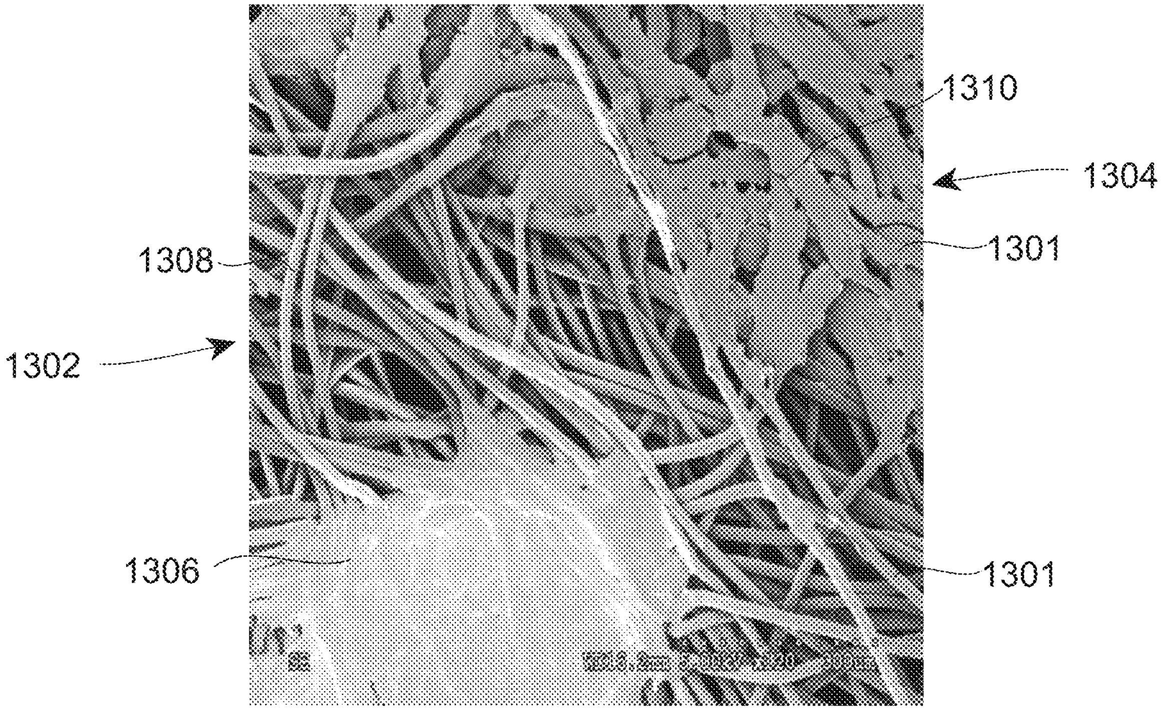
FIG. 14 is a scanning electron micrograph of a portion of a patterned fibrous substrate of the present disclosure.

Referring to FIGS. 13 and 14, the patterned fibrous substrates 1300 of the present disclosure comprise a plurality of individual fibers 1301, a first region 1302, and a second region 1304. The patterned fibrous substrate may also comprise a plurality of primary bonds 1306 distributed throughout the first region 1302 and the second region 1304. The plurality of primary bonds 1306 may comprise small areas of consolidated (fused) substrate fibers configured to hold the web structure together. At least two individual fibers 1301 may be consolidated (fused) to form a primary bond 1306. The individual fibers 1301 of the first region 1302 and the individual fibers 1301 of the second region 1304 are substantially free of bonds other than the primary bonds 1306. In other words, the individual fibers 1301 of the patterned fibrous substrates 1300 are substantially unattached, or unconsolidated, between the plurality of primary bonds 1306.

A plurality of the individual fibers 1301 of the first region 1302 of the patterned fibrous substrate 1300 may have a first shape. A plurality of the individual fibers 1301 of the second region 1304 of the patterned fibrous substrate 1300 may have a second shape. The first shape may be different than the second shape. Referring to FIG. 14, the plurality of the individual fibers 1301 of the first region 1302 and the plurality of the individual fibers 1301 of the second region 1304 may differ in the shape of the fiber when viewed from a first side or a second side (top or bottom) of the patterned fibrous substrate 1300. As shown in FIG. 14, the plurality of individual fibers 1301 of the first region 1302 may have a first diameter 1308, according to the Fiber Diameter Test Method described herein. The plurality of individual fibers 1301 of the second region 1304 may have a second diameter 1310, according to the Fiber Diameter Test Method described herein. The first diameter may be different than the second diameter. The second diameter may be greater than the first diameter. The second diameter may be 15% greater than the first diameter, 20% greater than the first diameter, 25% greater than the first diameter, 30% greater than the first diameter, 40% greater than the first diameter, or 50% greater than the first diameter, according to the Fiber Diameter Test Method described herein. The second diameter may be between about 15% and about 200% greater than the first diameter, between about 20% and about 185% greater than the first diameter, between about 25% and about 175% greater than the first diameter, between about 30% and about 175% greater than the first diameter, between about 40% and about 175% greater than the first diameter, or between about 50% and about 150% greater than the first diameter, all values within these ranges and any ranges formed therein or thereby, according to the Fiber Diameter Test Method described herein. As can be appreciated by FIG. 14, the fiber diameter of the individual fibers 1301 of the second region 1304 may vary as the individual fibers 1301 may not be smooth. The average second diameter, however, may be greater than the first diameter.

Figure 15:
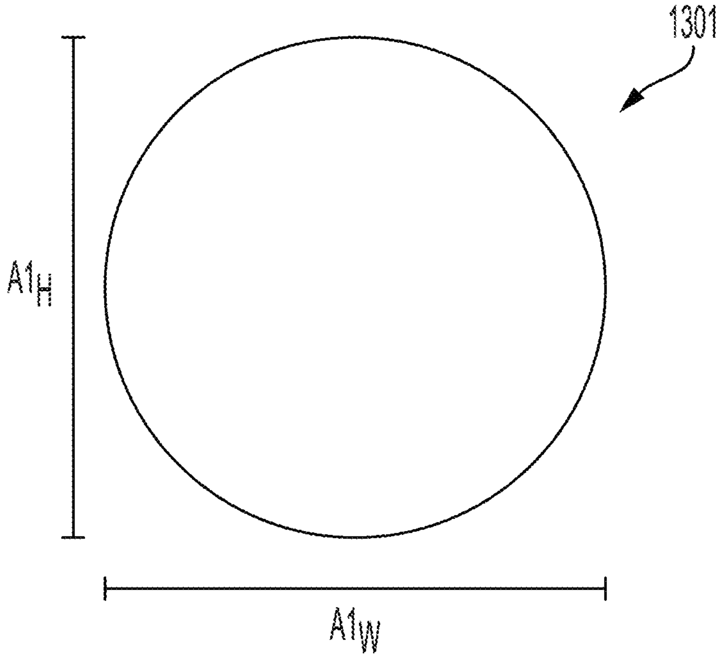
FIG. 15 is a schematic representation of a cross-sectional view of an individual fiber of the first region of a patterned fibrous substrate.
Figure 16:
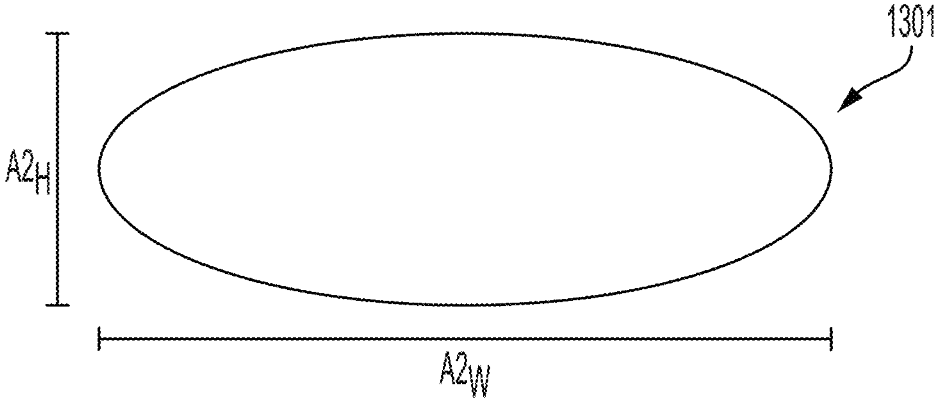
FIG. 16 is a schematic representation of a cross-sectional view of an individual fiber of the second region of a patterned fibrous substrate.

Referring to FIGS. 15 and 16, a plurality of the individual fibers 1301 of the first region 1302 and a plurality of the individual fibers 1301 of the second region 1304 may differ in the shape of the fiber when viewed in cross-section. A plurality of the individual fibers 1301 of the first region 1302 may have a first fiber cross-sectional shape that is substantially circular, as shown in FIG. 15. "Substantially circular," as used herein, means a cross-sectional dimension of an individual fiber having a cross-sectional width to cross-sectional height ratio (aspect ratio) of between about 1:1 to about 1.28:1. "Cross-sectional width," as used herein, means the largest cross-sectional dimension of an individual fiber, regardless of the orientation of the fiber to other fibers or to the plane of the patterned fibrous substrate. "Cross-sectional height," as used herein, means the cross-sectional dimension that is perpendicular to the fiber cross-sectional width. Again referring to FIG. 15, a plurality of the individual fibers 1301 of the first region 1302 may have a first cross-sectional width $\mathbf{A1}_w$ that is in ratio to a first cross-sectional height $\mathbf{A1}_h$ of between about 1:1 and about 1.28:1, between about 1;1 and about 1.25:1, between about 1:1 and about 1.20:1, or between about 1:1 and about 1.15:1, specifically reciting all values within these ranges and any ranges formed therein or thereby. The individual fibers 1301 of the first region 1302 of the patterned fibrous substrate 1300 may have an average aspect ratio of between about 1 and about 1.28, between about 1 and about 1.25, between about 1 and about 1.20, between about 1 and about 1.15, or less than about 1.28, less than about 1.25, less than about 1.20, or less than about 1.15, specifically reciting all values within these ranges and any ranges formed therein or thereby, according to the Aspect Ratio Test Method described herein.

Referring to FIG. 16, a plurality of the individual fibers 1301 of the second region 1304 may have a second fiber cross-section shape that is substantially flat. "Substantially flat," as used herein, means a cross-sectional dimension of an individual fiber having a cross-sectional width to cross-sectional height ratio (aspect ratio) of greater than about 1.30:1, or between about 1.30:1 and about 8:1, between about 1.35:1 and about 7:1, between about 1.4:1 and about 6:1, between about 1.45:1 and about 5:1, or between about 1.5:1 and about 3.5:1, specifically reciting all values within these ranges and any ranges formed therein or thereby, according to the Aspect Ratio Test Method described herein. Again referring to FIG. 16, a plurality of the individual fibers 1301 of the second region 1304 may have a second cross-sectional width $\mathbf{A2}_w$ that is in ratio to a second cross-sectional height $\mathbf{A2}_h$ of between about 1.3:1 and about 8:1, between about 1.35:1 and about 7:1, between about 1.4:1 and about 6:1, between about 1.45:1 and about 5:1, or between about 1.5:1 to about 3.5:1, specifically reciting all values within these ranges and any ranges formed therein or thereby, according to the Aspect Ratio Test Method describe herein. The individual fibers 1301 of the second region 1304 of the patterned fibrous substrate 1300 may have an average aspect ratio of between about 1.3 and about 3.5, between about 1.35 and about 3.0, between about 1.4 and about 2.75, or between about 1.45 and about 2.5, specifically reciting all values within these ranges and any ranges formed therein or thereby, according to the Aspect Ratio Test Method discussed herein.

The aspect ratio of a plurality of individual fibers in the first region of the patterned fibrous substrate ($\mathbf{A1}_w/\mathbf{A1}_h$) may be less than the aspect ratio of a plurality of individual fibers in the second region of the patterned fibrous substrate ($A2_w/A2_h$). In other words, a plurality of individual fibers disposed in the second region have a greater cross-sectional width-to-height ratio than a plurality of individual fibers disposed in the first region. The first cross-sectional width $A1_w$ of the plurality of individual fibers in the first region may be less than the second cross-sectional width $A2_w$ of the plurality of individual fibers in the second region.

A single fiber of the plurality of individual fibers may have a first fiber region having a first shape and a second fiber region having a second shape. The first shape may be different than the second shape. The first shape may differ from the second shape with regard to diameter, cross-sectional width-to-height ratio, and/or overall shape. The first fiber region may have a first shape that is substantially circular. The second fiber region may have a second shape that is substantially flat. The difference in shape of the first shape as compared to the second shape may be due to the first fiber region being disposed in the first region of the substrate, and the second fiber region being disposed in the second region of the substrate.

The patterned fibrous substrate of the present disclosure may be formed from a single fibrous substrate. The first region of the patterned fibrous substrate may not overlap the second region of the patterned fibrous substrate. In other words, the patterned fibrous substrate may be formed from a single fibrous substrate, wherein a first portion of the substrate forms the first region, and wherein a second and different portion of the substrate forms the second region. The patterned fibrous substrates of the present disclosure may be free of apertures.

The first region of the patterned fibrous substrates may be visually different as compared to the second region of the patterned fibrous substrates. The first region may be visually discernable from the second region. Without wishing to be bound by theory, it is believed that the difference in shape and/or aspect ratio and/or width of the plurality of fibers disposed in the first region versus the plurality of fibers disposed in the second region may cause light to reflect differently from the surfaces of the two regions, causing a difference in visual appearance. Due to the visual difference between the first and second regions of the patterned fibrous substrates, the first region and/or the second region may form a pattern or patterns in the fibrous substrate. A "pattern" and "patterns" as used herein may include the depiction of a design or designs, any recognizable indicia such as a number, a letter, a word, a brand name, an icon, a logo, a character, a front/back indicator, any shape and/or symbol (for example hearts, clouds, animals, etc.), as well as visible placement indicia to indicate where a sensor should be attached to the absorbent article, such as a dashed outline that matches the shape of a sensor, for example.

As opposed to forming patterns by traditional embossing, where individual fibers of a substrate fuse (bond) together, or coalesce, to form a film-like structure, the patterned fibrous substrates of the present disclosure comprise individual fibers that are not joined together, or coalesced, between primary bonds. As such, the patterned fibrous substrates of the present disclosure do not form a film-like structure, and therefore may be softer, more flexible, and/or more absorbent as compared to embossed substrates, while still providing a pattern that may be aesthetically pleasing and/or communicate functionality of the substrate.

Figure 30:
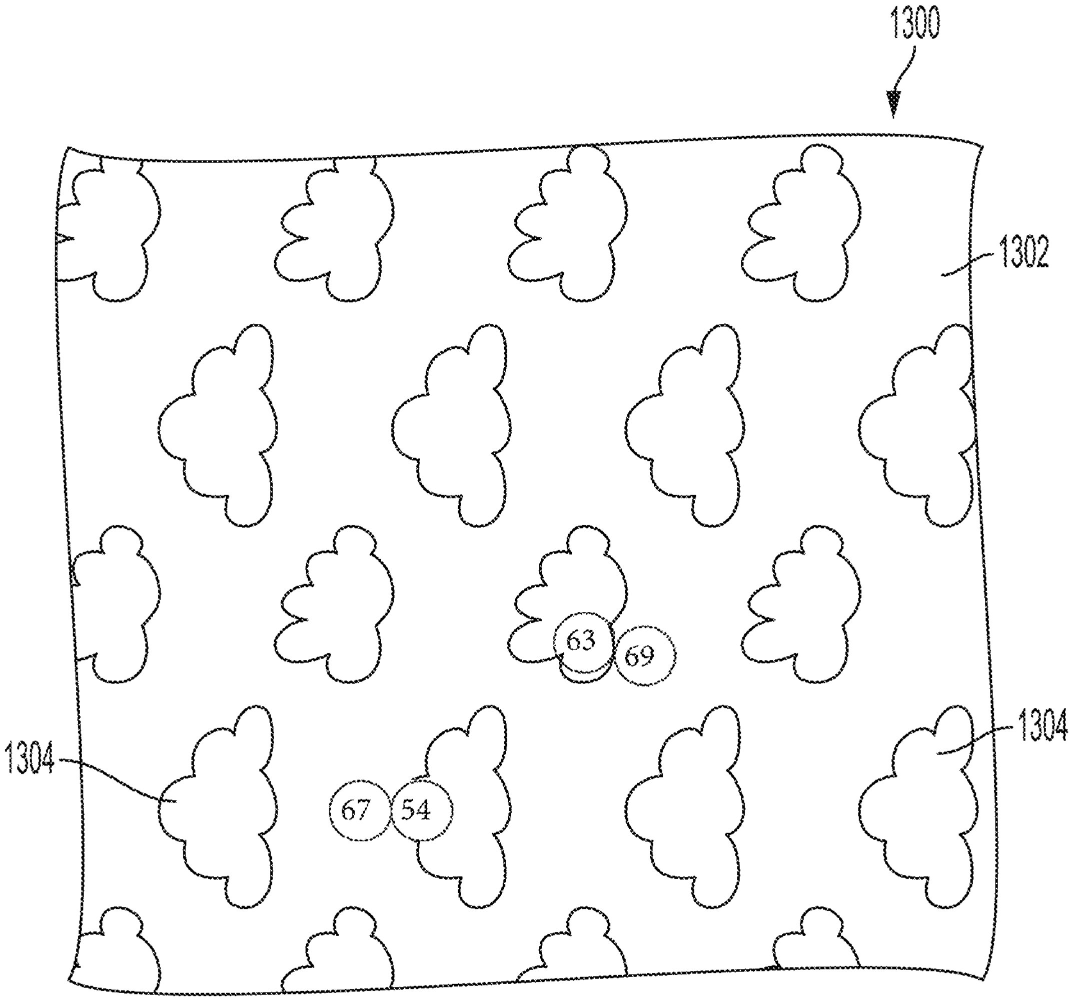
FIG. 30 is an image of a patterned fibrous substrate of the present disclosure utilized for determine light transmission according to the Light Transmission Test Method described herein.

A visual difference between the first region and the second region may be measured as a difference in light transmission value. The first region of the patterned fibrous substrate may have a first light transmission value, according to the Light Transmission Test Method described herein. The second region of the patterned fibrous substrate may have a second light transmission value, according to the Light Transmission Test Method described herein. The first light transmission value may be different than the second light transmission value. The second light transmission value may be less than the first light transmission value, as shown in FIG. 30. The absolute difference (reported as a non-negative number) between the first light transmission value and the second light transmission value is referred to herein as ΔLT. The ΔLT may be greater than 5, greater than 8, greater than 10, or between about 5 and about 50, between about 8 and about 35, or between about 10 and about 25, specifically reciting all values within these ranges and any ranges formed therein or thereby, according to the Light Transmission Test Method described herein. The percent difference between the first light transmission value and the second light transmission score may be between about 5% and about 65%, between about 8% and about 50%, or between about 10% and about 40%, specifically reciting all values within these ranges and any ranges formed therein or thereby, according to the Light Transmission Test Method described herein.

A visual difference between the first region and the second region may be measured as a difference in opacity. The first region of the patterned fibrous substrate may have a first opacity, according to the Opacity Test Method described herein. The second region of the patterned fibrous substrate may have a second opacity, according to the Opacity Test Method described herein. The first opacity may be different than the second opacity. The second opacity may be greater than the first opacity. The absolute difference (reported as a non-negative number) between the first opacity and the second opacity is referred to herein as ΔOpacity. For example, the ΔOpacity between a first opacity of 10% and a second opacity of 14% is 4. The ΔOpacity may be greater than 5, greater than 8, greater than 10, or between about 5 and about 30, between about 8 and about 25, or between about 10 and about 20, specifically reciting all values within these ranges and any ranges formed therein or thereby, according to the Opacity Test Method described herein. The percent difference between the first opacity and the second opacity may be greater than 5%, greater than 10%, greater than 15%, or between about 5% and about 60%, between about 10% and about 60%, or between about 15% and about 50%, specifically reciting all values within these ranges and any ranges formed therein or thereby, according to the Opacity Test Method described herein.

A visual difference between the first region and the second region may be measured as a difference in color. Color and/or colors may be characterized by C.I.E. L*, a*, b* values, according to the Color Test Method described herein. The C.I.E. L*, a*, b* color scale utilizes measures of lightness (L*), redness-greenness (a*), and yellowness-blueness (b*) to characterize colors. A color difference characterized by a difference in C.I.E. L*, a*, and/or b* scores between the first region and the second region may be demonstrated in any of the patterned fibrous substrates of the present disclosure, but may be especially useful where the individual fibers of the substrate comprise a pigment, colorant, and/or dye. In such cases, differences in opacity between the first region and the second region of the substrate may be subtle, and color differences may be more pronounced.

The first region of the patterned fibrous substrate may have a first C.I.E. L* score, according to the Color Test Method described herein. The second region of the patterned fibrous substrate may have a second C.I.E. L* score, according to the Color Test Method described herein. The first C.I.E. L* score may be different than the second C.I.E. L* score. The first C.I.E. L* score may be higher than or lower than the second C.I.E. L*. The absolute difference (reported as a non-negative number) between the first C.I.E. L* score and the second C.I.E. L* score is herein referred to as the ΔL*. A difference in C.I.E. L* score of greater than about 2 may be perceptible to the human eye. The ΔL* may be greater than 4, greater than 6, greater than 10, or between about 4 and about 30, between about 6 and about 20, or between about 10 and about 15, specifically reciting all values within these ranges and any ranges formed therein or thereby, according to the Color Test Method described herein.

The first region of the patterned fibrous substrate may have a first C.I.E. a* score, according to the Color Test Method described herein. The second region of the patterned fibrous substrate may have a second C.I.E. a* score, according to the Color Test Method described herein. The first C.I.E. a* score may be different than the second C.I.E. a* score. The first C.I.E. a* score may be higher than or lower than the second C.I.E. a*. The absolute difference (reported as a non-negative number) between the first C.I.E. a* score and the second C.I.E. a* score is herein referred to as the Δa*. The Δa* may be greater than 5, greater than 8, greater than 10, or between about 5 and about 60, between about 10 and about 60, between about 10 and about 50, or between about 10 and about 40, specifically reciting all values within these ranges and any ranges formed therein or thereby, according to the Color Test Method described herein.

The first region of the patterned fibrous substrate may have a first C.I.E. b* score, according to the Color Test Method described herein. The second region of the patterned fibrous substrate may have a second C.I.E. b* score, according to the Color Test Method described herein. The first C.I.E. b* score may be different than the second C.I.E. b* score. The first C.I.E. b* score may be higher than or lower than the second C.I.E. b*. The absolute difference (reported as a non-negative number) between the first C.I.E. b* score and the second C.I.E. b* score is herein referred to as the Δb*. The Δb* may be greater than 5, greater than 8, greater than 10, or between about 5 and about 60, between about 10 and about 60, between about 10 and about 50, or between about 10 and about 40, specifically reciting all values within these ranges and any ranges formed therein or thereby, according to the Color Test Method described herein.

A visual difference between the first region and the second region may be measured as a difference in gloss. The first region of the patterned fibrous substrate may have a first gloss value, according to the Gloss Test Method described herein. The second region of the patterned fibrous substrate may have a second gloss value, according to the Gloss Test Method described herein. The first gloss value may be different than the second gloss value. The absolute difference (reported as a non-negative number) between the first gloss value and the second gloss value is referred to herein as ΔGloss. The ΔGloss may be greater than 5, greater than 8, greater than 10, or between about 5 and about 50, between about 8 and about 35, or between about 10 and about 25, specifically reciting all values within these ranges and any ranges formed therein or thereby, according to the Gloss Test Method described herein. The percent difference between the first gloss value and the second gloss value may be between about 5% and about 65%, between about 8% and about 50%, or between about 10% and about 40%, specifically reciting all values within these ranges and any ranges formed therein or thereby, according to the Gloss Test Method described herein.

It has been found that patterned fibrous substrates of the present disclosure comprising fibers having little to no pigments and/or opacifiers may result in an increased visual difference (visual contrast) between the first region and the second region, thus making a pattern in the patterned fibrous substrate more noticeable. Pigments and/or opacifiers—such as titanium dioxide—however, may function to reduce the visibility of primary bonds, thus reducing distraction from the pattern created by the visual differences between the first region and the second region. Therefore, there may be a benefit to including a low level of pigment and/or opacifier in the fibers of the patterned fibrous substrates of the present disclosure.

Figure 17:
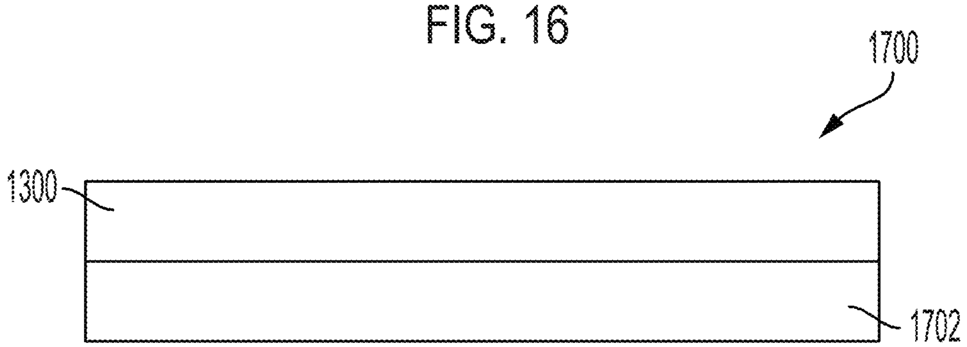
FIG. 17 is a schematic representation of a cross-sectional view of a laminate comprising a patterned fibrous substrate.

As shown in FIG. 17, the patterned fibrous substrate 1300 of the present disclosure may form a portion of a laminate 1700. The laminate 1700 may comprise at least a portion of the patterned fibrous substrate 1300 and at least a portion of a second substrate 1702. The second substrate 1702 may be a nonwoven substrate, a woven substrate, a patterned fibrous substrate of the present disclosure, an elastomeric film or sheet, or any other type of substrate capable of being formed into a laminate. At least a portion of the patterned fibrous substrate 1300 may be joined to at least a portion of the second substrate 1700 by any known method in the art, including by use of adhesives, thermal bonding, pressure bonding, ultrasonic bonding, and combinations thereof. The laminate may comprise a patterned fibrous substrate 1300, a second substrate 1702, and an elastic strand or a plurality of elastic strands disposed at least partially between the patterned fibrous substrate 1300 and the second substrate 1702. In a form, the laminate 1700 may comprise a patterned fibrous substrate 1300, a second substrate 1702, wherein the second substrate 1702 is also a patterned fibrous substrate 1300, and a plurality of elastic strands disposed at least partially between the patterned fibrous substrate 1300 and the second substrate 1702.

The patterned fibrous substrate 1300 may be a first color, and the second substrate 1702 may be a second color. The first color may be the same as the second color, or the first color may be different than the second color. A laminate comprising a patterned fibrous substrate 1300 and a second substrate 1702, wherein the patterned fibrous substrate 1300 and the second substrate 1702 are the same or a similar color, may produce a laminate with a subtle patterned effect. The second substrate 1702 may be a darker color or a lighter color as compared to the patterned fibrous substrate 1300. Combining a patterned fibrous substrate 1300 with a second substrate 1702 of a different color into a laminate may produce a laminate with a pronounced and highly visible patterned effect. The second substrate 1702 may comprise a pattern, wherein the pattern disposed on the second substrate is the same as, or different than, the pattern of the patterned fibrous substrate 1300.

A portion of the patterned fibrous substrate 1300 forming at least a portion of the laminate 1700 may have a first C.I.E. L* score, according to the Color Test Method described herein. A portion of the second substrate 1702 may have a second substrate C.I.E. L* score, according to the Color Test Method described herein. The first C.I.E. L* score may be different than the second substrate C.I.E. L* score. The first C.I.E. L* score may be equal to or greater than the second substrate C.I.E. L* score. It is believed that a laminate comprising a patterned fibrous substrate of the present disclosure and a second substrate, wherein at least a portion of the patterned fibrous substrate has a C.I.E. L* score that is equal to or greater than (equal to or whiter than) the C.I.E.

L* score of the second substrate provides a laminate with a more pronounced and highly visible pattern.

Figure 28A:
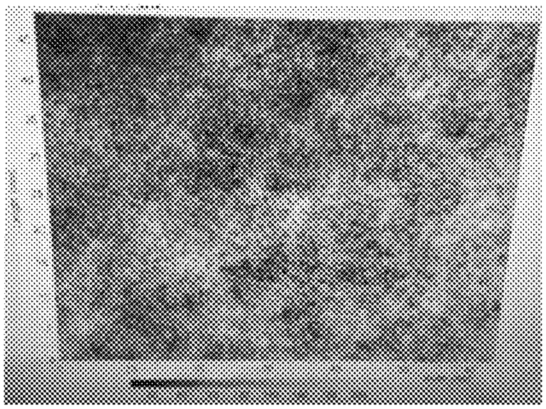
FIG. 28A is an image of a non-patterned fibrous substrate comprising only primary bonds with no patterns or embossing.
Figure 28B:
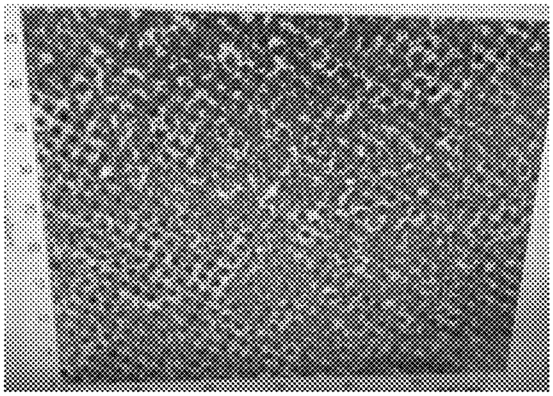
FIG. 28B is an image of a topographical analysis of the non-patterned fibrous substrate of FIG. 28A.
Figure 29A:
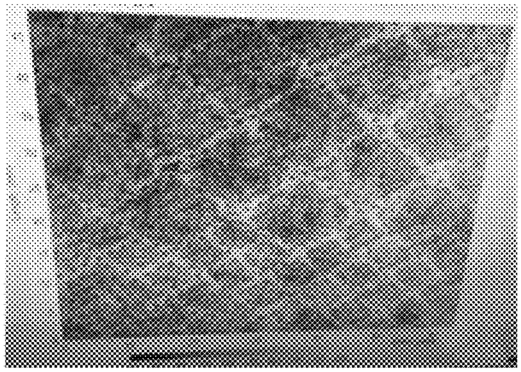
FIG. 29A is an image of a patterned fibrous substrate of the present disclosure.
Figure 29B:
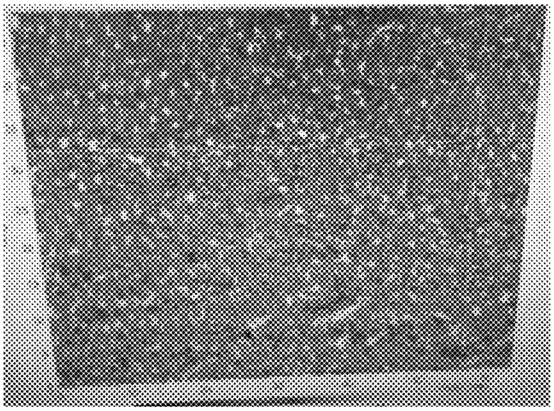
FIG. 29B is an image of a topographical analysis of the patterned fibrous substrate of FIG. 29A.

As opposed to forming patterns by traditional embossing, where individual fibers of a substrate fuse (bond) together, or coalesce, to form a film-like structure, the patterned fibrous substrates of the present disclosure comprise individual fibers that are not joined together, or coalesced, between primary bonds. As such, the patterned fibrous substrates of the present disclosure may have a substantially consistent caliper across both the first region and the second region. Thus, while there is a visual difference between the first region and the second region, there is no substantial difference in thickness, or caliper, of the patterned fibrous substrate when measured in the first region versus measured in the second region. FIG. 28A shows an image of a non-patterned fibrous substrate comprising only primary bonds with no patterns or embossing. FIG. 28B shows an image of a topographical analysis of the non-patterned fibrous substrate of FIG. 28A. FIG. 29A shows an image of a patterned fibrous substrate of the present disclosure, comprising a first region and a second region. The first region is visually different than the second region. The visual difference between the first region and the second creates a pattern of lines forming diamond patterns in the substrate. FIG. 29B is an image of a topographical analysis of the patterned fibrous substrate of FIG. 29A, showing that the diamond pattern is not visible, indicating that the pattern, while visually discernable, does not impact the thickness, or caliper, of the patterned fibrous substrate. It is believed that the visual difference between the first region and the second region of the patterned fibrous substrate is due primarily to the difference in the shape of fibers between these two regions. However, because the fibers of the first region and the fibers of the second region are not embossed, meaning that they are generally free of attachment outside of primary bonds, the loft and/or caliper of the substrate across the first region and second region is substantially consistent. The caliper of the patterned fibrous substrate as measured in the first region may be no greater than 10% different than the caliper of the patterned fibrous substrate as measured in the second region.

The first region of the patterned fibrous substrates of the present disclosure may have a first region permeability score (PS1), according to the Fluid Permeability Test Method disclosed herein. The second region of the patterned fibrous substrates of the present disclosure may have a second region permeability score (PS2), according to the Fluid Permeability Test Method disclosed herein. The first region permeability score (PS1) may be the same as or greater than the second region permeability score (PS2). The first region permeability score (PS1) may be greater than 5.0 Darcy, greater than 25.0 Darcy, greater than 50.0 Darcy, or greater than 70.0 Darcy, according to the Fluid Permeability Test Method disclosed herein. The second region permeability score (PS2) may be greater than 5.0 Darcy, greater than 10.0 Darcy, greater than 15.0 Darcy, or greater than 20.0 Darcy, according to the Fluid Permeability Test Method disclosed herein. The first region permeability score may be between about 1.3 times and about 80 times greater, between about 1.5 times and about 70 times greater, between about 1.8 and about 65 times greater, or between about 2.5 and about 55 times greater than the second region fluid permeability score (PS2). While the first region permeability score (PS1) may be the same as or greater than the second region permeability score (PS2), both PS1 and PS2 may be such that both the first region and the second region both allow the flow of fluid. The first region and the second region of the patterned fibrous substrates of the present disclosure may both be considered fluid permeable. For example, both the first region permeability score (PS1) and the second region permeability score (PS2) may be greater than 5 Darcy. Thus, patterned fibrous substrates of the present disclosure may be particularly suited for use as portions or components of absorbent articles where fluid permeability is a desirable attribute, such as a permeable topsheet, for example.

Where the patterned fibrous substrates of the present disclosure comprise a bond, the area of the patterned fibrous substrate where the bond is disposed (the area of fused fibers), herein known as the bond region, has a bond permeability score (PSB). The first region permeability score (PS1) and the second region permeability score (PS2) may both be greater than the bond permeability score (PSB). It is believed that the first region and second region comprise a plurality of individual fibers that are not fused or otherwise consolidated, whereas a bond region comprises fibers that are fused together. Therefore, the first and second regions may have different permeability scores, but both the first and second regions allow fluid to flow between the separate fibers. The bond region, on the other hand, allows significantly less fluid to flow between fibers because the fibers are fused together. Thus, patterned fibrous substrates of the present disclosure that may be desired for use as a fluid permeable component of an absorbent article, such as a permeable topsheet, for example, may be free of bonds other than primary bonds.

Methods of Making Patterned Fibrous Substrates

Figure 18:
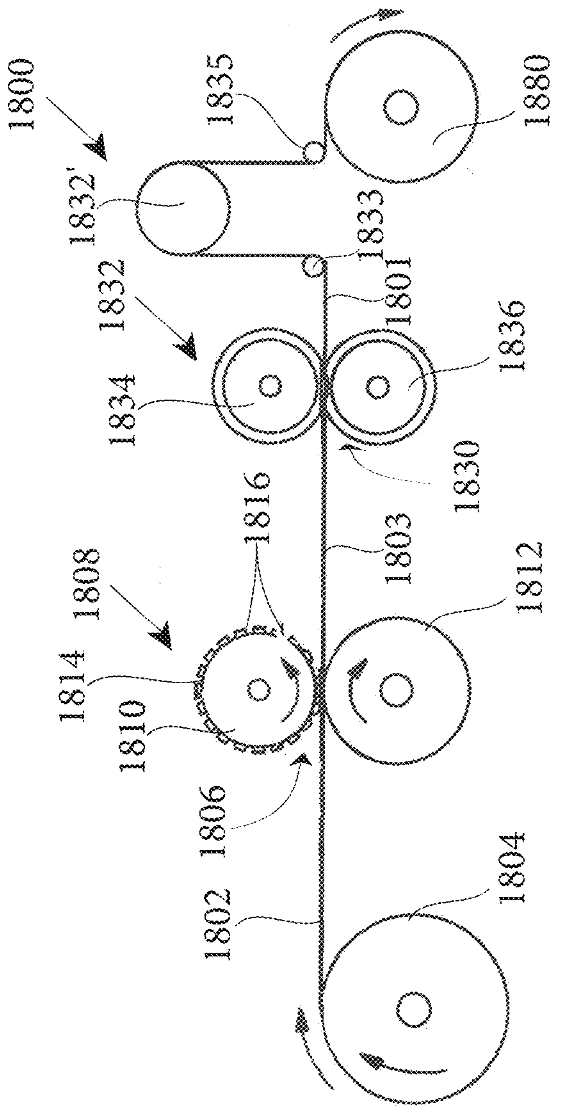
FIG. 18 is a schematic representation of an example process for producing a patterned fibrous substrate.

Referring to FIG. 18, there is schematically illustrated in 1800 one process for forming the patterned fibrous substrates of the present disclosure.

First, a fibrous substrate 1802 of the present disclosure is supplied as a starting material. The fibrous substrate 1802 may be supplied as discrete webs, e.g., sheets, patches, etc. of material for batch processing. For commercial processing, however, the fibrous substrate 1802 may be supplied as roll stock, and, as such it may be considered as having a finite width and an infinite length.

The fibrous substrate 1802 may be one or more fibrous materials (same or different). The fibrous substrate 1802 may be purchased from a supplier and shipped to where the patterned fibrous substrates are being formed or the fibrous substrate 1802 may be formed at the same location as where the patterned fibrous substrates are being produced.

The fibrous substrate 1802 may be unwound from a supply roll 1804 and travel in a direction indicated by the arrow associated therewith as the supply roll 1804 rotates in the direction indicated by the arrow associated therewith. The fibrous substrate 1802 may pass through a nip 1806 of a deforming roller arrangement 1808 formed by rollers 1810 and 1812, thereby forming a regioned fibrous substrate 1803. The regioned fibrous substrate 1803 comprises a first region and a second region after passing through the nip 1806. A plurality of fibers forming the first region have a first cross-sectional shape, and a plurality of the fibers forming the second region have a second cross-sectional shape, wherein the first cross-sectional shape is different than the second cross-sectional shape. The first region and/or the second region may be formed by pattern elements and/or protuberances on the surface of one or both of the rollers 1810 and 1812, as discussed further below.

Referring again to FIG. 18, the fibrous substrate deforming roller arrangement 1808 may comprise a patterned roller 1810 and a smooth anvil roller 1812. One or both of the patterned roller 1810 and the smooth anvil roller 1812 may be heated and the pressure at the nip 1806 may be adjusted by known techniques to provide the desired temperature, if any, and pressure to form a regioned fibrous substrate 1803 comprising a first region and a second region. Generally, the pressure or pressure and heat should be great enough to deform a majority of fibers in one of the first region or second region without fusing the fibers together to form a bond. The pressure at the nip 1806 be in the range of about from about 5,000 psi (pounds per square inch) to about 70,000 psi, from about 10,000 psi to about 70,000 psi, from about 15,000 psi to about 70,000 psi, or from about 25,000 psi to about 70,000 psi, specifically reciting all 1.0 psi increments within the specified ranges and all ranges formed therein or thereby. Where neither roller is heated (the rollers are at ambient temperature), the pressure at the nip 1806 may be in the range of about from about 10,000 psi to about 70,000 psi, from about 25,000 psi to about 70,000 psi, or from about 30,000 psi to about 70,000 psi, specifically reciting all 1.0 psi increments within the specified ranges and all ranges formed therein or thereby. Where either one or both of the rollers 1810 and 1812 are heated, the pressure at the nip 1806 may be in the range of about from about 5,000 psi to about 50,000 psi, from about 10,000 psi to about 35,000 psi, or from about 15,000 psi to about 25,000 psi, specifically reciting all 1.0 psi increments within the specified ranges and all ranges formed therein or thereby.

The temperature of the patterned roller 1810 (or portions thereof) and/or the smooth anvil roller 1812 (or portions thereof) may be ambient temperature or may be in the range of about 50° C. to about 180° C., about 80° C. to about 150° C., or about 100° C. to about 130° C., specifically reciting all 0.5° C. increments within the specified ranges and all ranges formed therein or thereby.

Figure 20:
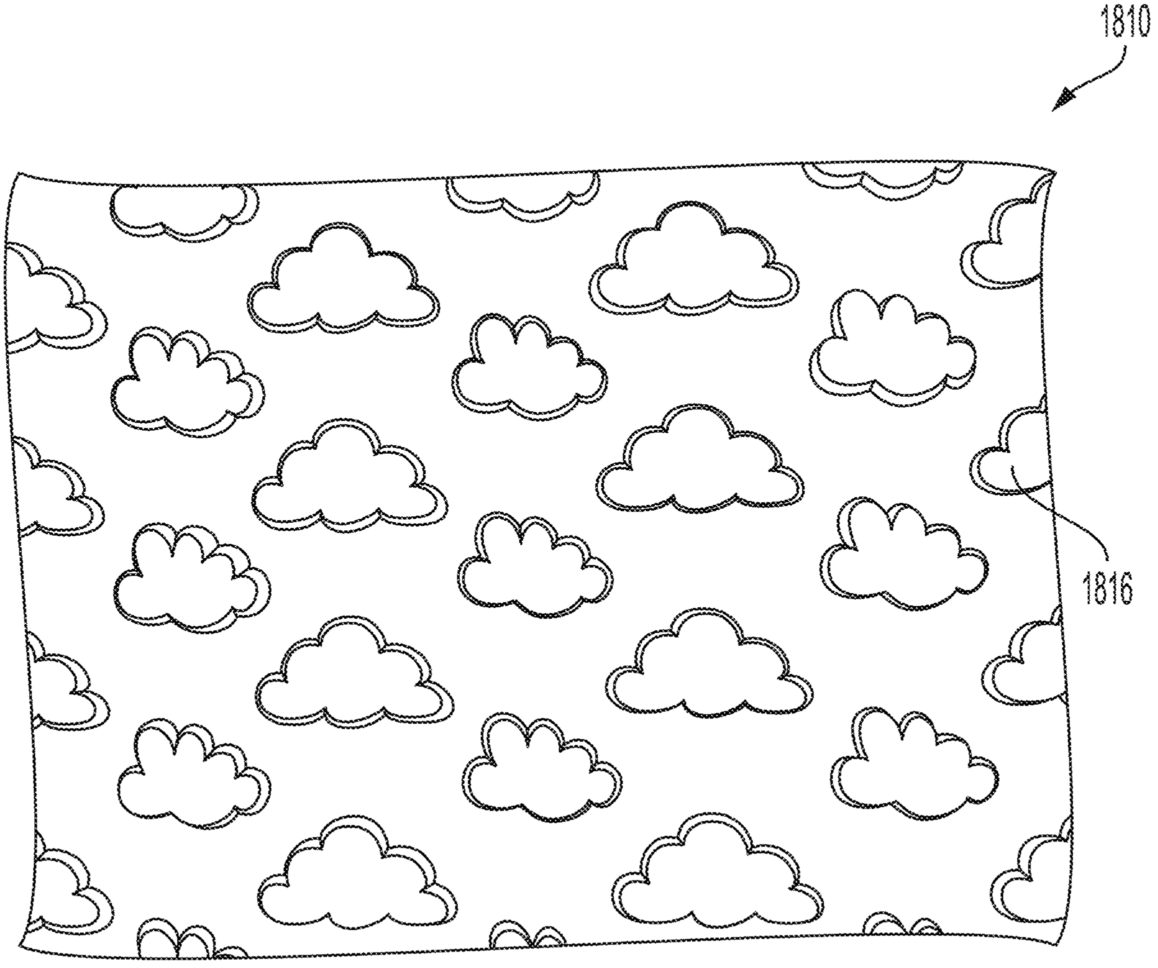
FIG. 20 is a photograph of a portion of a surface of an example deforming roller that can be used as roller 1810 in the deforming roller arrangement of FIG. 19.

The patterned roller 1810 may be configured to have a cylindrical surface 1814, and a plurality of protuberances or pattern elements 1816 which extend outwardly from the cylindrical surface 1814. The pattern elements 1816 are illustrated as a simplified example of a patterned roller 1810 to produce regioned fibrous substrates 1803, but more detailed pattern elements 1816 that can be used to produce a patterned fibrous substrate are illustrated in FIG. 20. The pattern elements 1816 may be disposed in a predetermined pattern with each of the pattern elements 1816 being configured and disposed to form a first region and/or a second region in the regioned fibrous web 1803 to create at least one region comprising a plurality of deformed fibers in the regioned fibrous web 1803. As shown in FIG. 18, the patterned roller 1810 may have a repeating pattern of the protuberances or pattern elements 1816 which extend about the entire circumference of the surface 1814. Alternatively, the protuberances or pattern elements 1816 may extend around a portion, or portions of the circumference of the surface 1814. Also, a single patterned roller may have a plurality of patterns in various zones (i.e., first zone, first pattern, second zone, second pattern). Spacing between adjacent portions of pattern elements 1816 in any direction may be greater than about 0.5 mm, greater than about 0.6 mm, greater than about 0.7 mm, greater than about 0.8 mm, greater than about 0.9 mm, greater than about 1 mm, greater than about 1.1 mm, greater than about 1.2 mm, greater than about 1.3 mm, greater than about 1.4 mm, greater than about 1.5 mm, greater than about 2 mm, greater than about 3 mm, or may be in the range of about 0.7 mm to about 20 mm, or about 0.8 to about 15 mm, specifically reciting all 0.1 mm increments within the specified ranges and all ranges formed therein or thereby.

Figure 19:
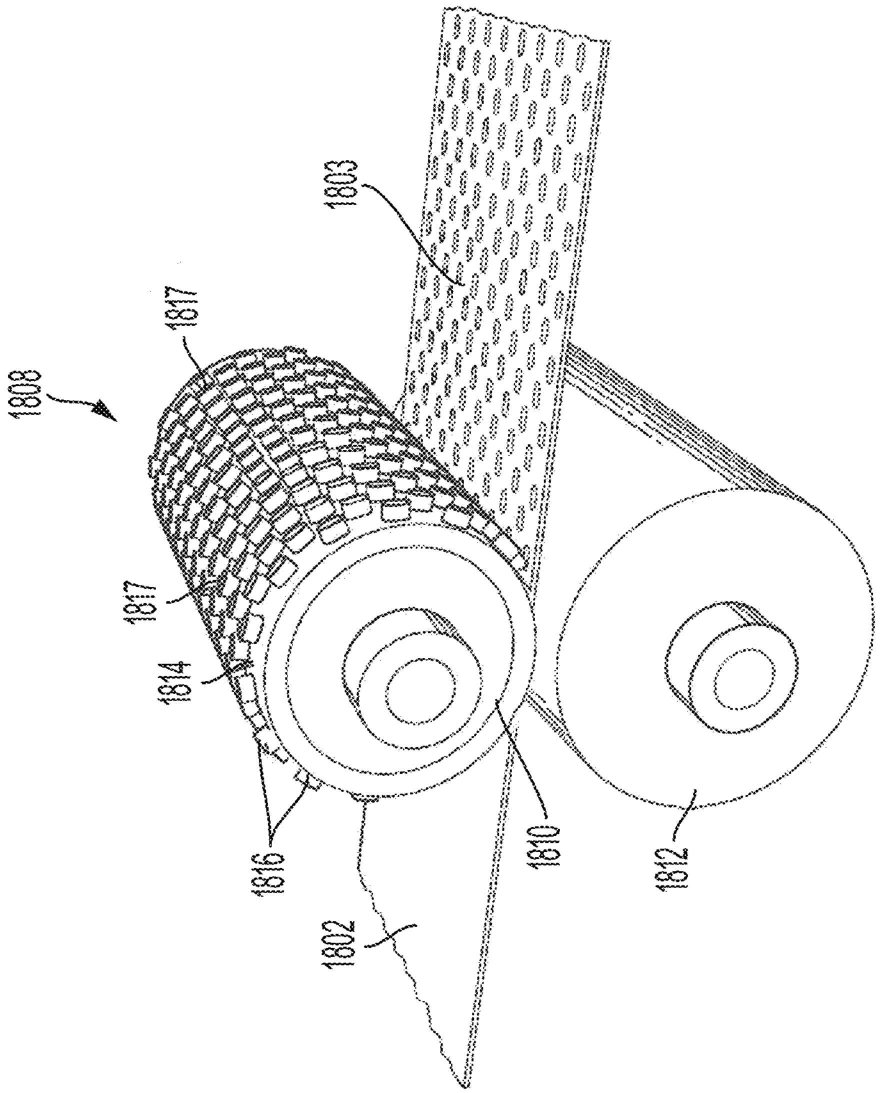
FIG. 19 is a perspective view of a deforming roller arrangement of FIG. 18.

An example roller that may be used as patterned roller 1810 in the process 1800 of FIG. 18 to produce the regioned fibrous substrates of the present disclosure is illustrated in FIG. 20. The pattern of pattern elements 1816 on the patterned roller in FIG. 20 may form a first region and/or a second region in a regioned fibrous substrate 1803, much like regions formed in the regioned fibrous substrate 1203 of FIG. 19. The protuberances an/or pattern elements 1816 may extend radially outwardly from surface 1814 and have distal end surfaces 1817. The anvil roller 1812 may be a smooth surfaced, circular cylinder of steel, rubber, or other material. The anvil roller 1812 and the patterned roller 1810 may be switched in position (i.e., anvil on top) and achieve the same result.

In some cases, the regioned fibrous substrate 1803 is the patterned fibrous substrate of the present disclosure. In such cases, the pressure or combination of pressure and heat of the deforming roller arrangement 1808 may be sufficient to deform the plurality of fibers in the first or second regions of the regioned fibrous substrate without causing the polymer of the fibers to flow and adhere to adjacent fibers. Thus, the individual fibers of the first region and the individual fibers of the second region are substantially free of bonds, other than primary bonds.

In other cases, where some of the individual fibers in the first and/or second regions adhered to adjacent fibers as a result of the deforming process, a further incremental stretching step may be performed. The individual fibers may be re-oriented and spread apart by application of suitable mechanical force. Such mechanical force may be applied by, for example, line tension or by process devices such as, for example, a bow bar(s), tenter frame, bow idlers, power spreader, or by an incremental stretching system as discussed further herein.

Referring again to FIG. 18, from the deforming roller arrangement 1808, the regioned fibrous substrate 1803 may pass through a nip 1830 formed by an incremental stretching system 1832 employing opposed pressure applicators having three-dimensional surfaces which at least to a degree may be complementary to one another.

Figure 21:
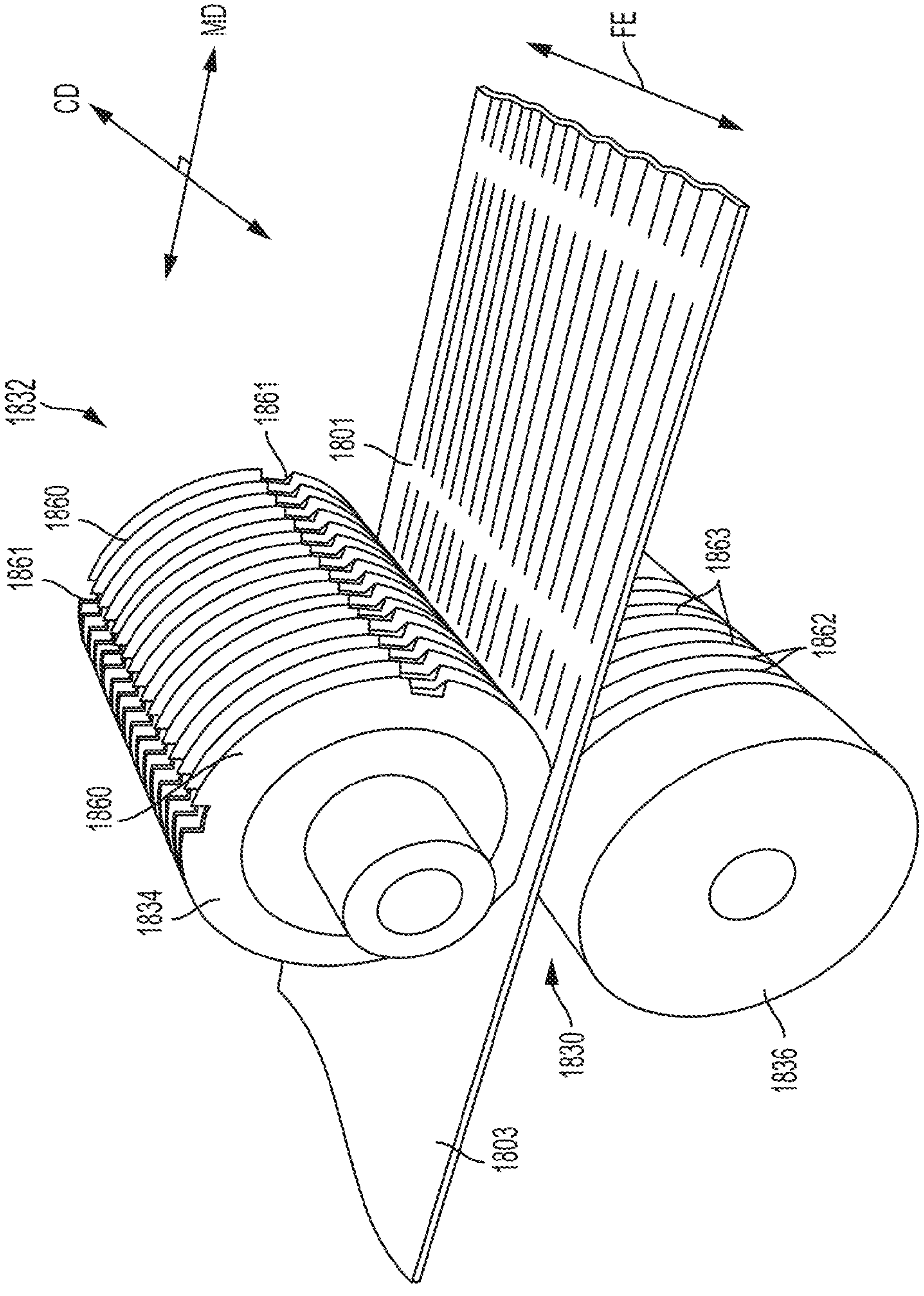
FIG. 21 is a perspective view of an incremental stretching system 1832 of FIG. 18.

Referring now to FIG. 21 there is shown a fragmentary enlarged view of the incremental stretching system 1832 comprising two incremental stretching rollers 1834 and 1836. The first incremental stretching roller 1834 may comprise a plurality of teeth 1860 and corresponding grooves 1861 which may be present about the entire circumference of first incremental stretching roller 1834. The second incremental stretching roller 1836 may comprise a plurality of teeth 1862 and a plurality of corresponding grooves 1863. The teeth 1860 on the first roller 1834 may intermesh with or engage the grooves 1863 on the second roller 1836 while the teeth 1862 on the second roller 1836 may intermesh with or engage the grooves 1861 on the first roller 1834. The spacing and/or pitch of the teeth 1862 and/or the grooves 1863 may match the pitch and/or spacing of the locations of the first and/or second regions in the regioned fibrous substrate 1803 or may be smaller or larger. As the regioned fibrous substrate 1803 passes through the incremental stretching system 1832, the regioned fibrous substrate 1803 is subjected to tensioning in the CD causing the regioned fibrous web 1803 to be extended (or activated) in the CD, or generally in the CD. Additionally, the regioned fibrous substrate 1803 may be tensioned in the MD, or generally in the MD. The CD tensioning force placed on the regioned fibrous substrate may be adjusted such that it causes any individual fibers of the first region and/or the second region that may have bonded to any adjacent fibers, to pull apart, such that the majority of individual fibers in the first region and the second region are substantially free of bonds other than the primary bonds. However, the primary bonds of the patterned fibrous substrate 1801 and the regioned fibrous substrate 1803 may be strong enough such that they may not rupture during tensioning, thereby maintaining the patterned fibrous substrate 1801 in a coherent condition even as any superficial bonding between individual fibers that may have formed during the deforming roller process rupture. However, it may be desirable to have some of the primary bonds rupture during tensioning.

Figure 22:
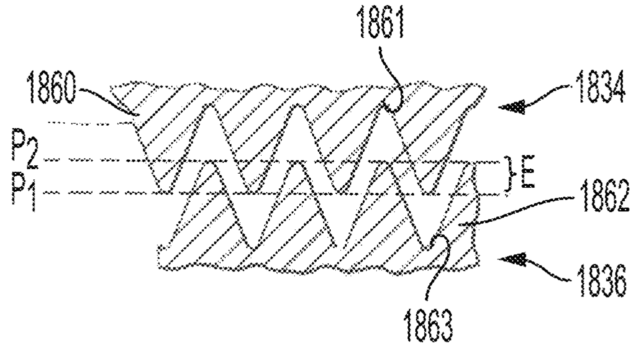
FIG. 22 is an enlarged view showing the details of teeth of the incremental stretching system of FIG. 21.

Referring to FIG. 22, a more detailed view of the teeth 1860 and 1862 and the grooves 1861 and 1863 on the first roller 1834 and second roller 1836 is illustrated. The term "pitch" refers to the distance between the apexes of adjacent teeth. The pitch may be between about 0.02 inches to about 0.40 inches (about 0.51 mm to about 10.16 mm) or may be between about 0.04 inches and about 0.15 inches (about 1.00 mm to about 3.81 mm), specifically reciting all 0.001 inch increments within the above-specified ranges and all ranges formed therein or thereby. The height (or depth) of the teeth may be measured from the base of the tooth to the apex of the tooth, and may or may not be equal for all teeth. The height of the teeth may be between about 0.010 inches (about 0.254 mm) and about 0.90 inches (about 22.9 mm) or may be between about 0.025 inches (about 0.635 mm) and about 0.50 inches (about 12.7 mm), specifically reciting all 0.01 inch increments within the above-specified ranges and all ranges formed therein or thereby. The teeth 1860 in one roll may be offset by about one-half of the pitch from the teeth 1862 in the other roll, such that the teeth of one roll (e.g., teeth 1860) mesh in the valley (e.g., groove 1863) between teeth in the mating roll. The offset permits intermeshing of the two rolls 1834 and 1836 when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 22, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular substrates may be dependent upon the height and the pitch of the teeth and/or the structure of the material. Some example DOEs may be in the range of about 0.005 inches (about 0.127 mm) to about 0.2 inches (5.08 mm), about 0.01 inches (about 0.254 mm) to about 0.1 inches (about 2.54 mm), about 0.015 inches (about 0.381 mm) to about 0.07 inches (about 1.778 mm), specifically reciting all 0.001 inch increments within the above-specified ranges and all ranges formed therein or thereby.

As the regioned fibrous substrate 1803 passes through the incremental web stretching apparatus 1832, the regioned fibrous substrate 1803 may be subjected to tensioning in the cross-machine direction, or substantially in the cross-machine direction, thereby causing the regioned fibrous substrate 1803 to be extended in the cross-machine direction. The tensioning force placed on the regioned fibrous substrate 1803 may be adjusted by varying the pitch, DOE, or teeth size, such that the incremental stretching is sufficient to cause any individual fibers of the first region and/or the second region that may have bonded to any adjacent fibers through the deformer roller arrangement 1808, to pull apart, such that the majority of individual fibers in the first region and the second region are substantially free of bonds other than the primary bonds.

Figure 23:
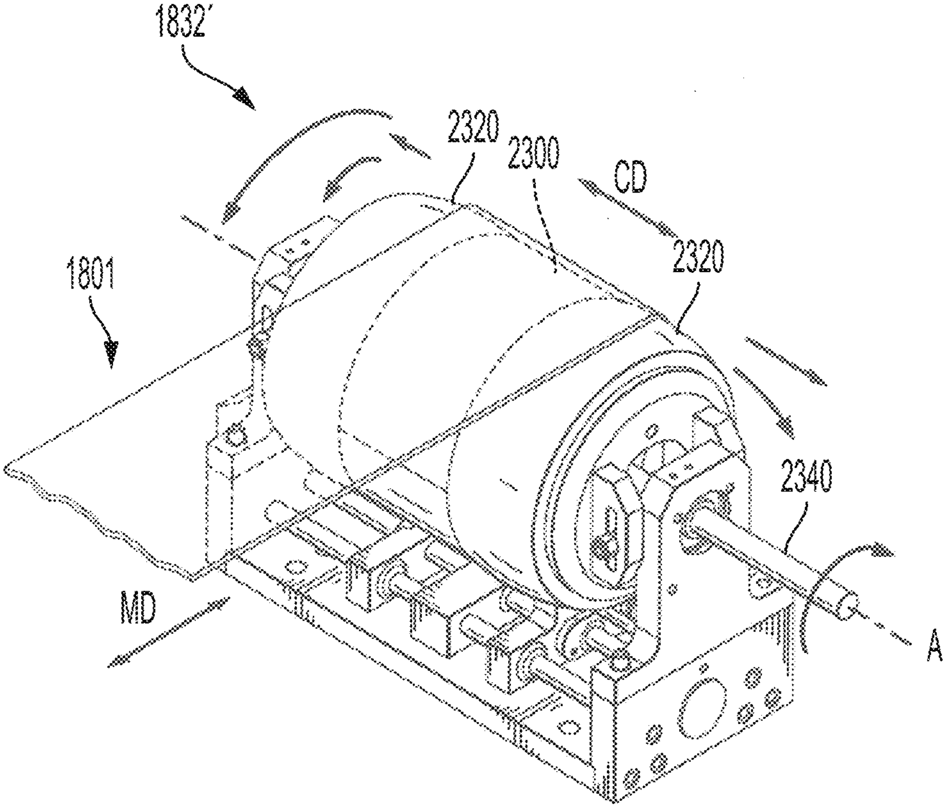
FIG. 23 is a perspective view of an example cross-machine directional tensioning apparatus of FIG. 18.

Referring again to FIG. 18, after, or instead of, passing the regioned fibrous substrate 1803 through the incremental web stretching apparatus 1832, the patterned fibrous substrate 1801 may be advanced to and at least partially around a cross-machine directional tensioning apparatus 1832'. As shown in FIG. 23, the cross-machine directional tensioning apparatus 1832' may be offset from the main processing line by running the regioned fibrous substrate 1803 or patterned fibrous substrate 1801 partially around two idlers 1833 and 1835 or stationary bars, for example. In other instances, the cross-machine tensioning apparatus 1832' may be positioned in line with the main processing line. The cross-machine directional tensioning apparatus 1832' may comprise a roll that comprises at least one outer longitudinal portion that expands along a longitudinal axis of the roll, relative to a middle portion of the roll, to stretch and/or expand the substrate 1801 or 1803 in the cross-machine direction. Instead of, or in addition to, expanding along the longitudinal axis of the roll, the outer longitudinal portion may be angled relative to the longitudinal axis of the roll in a direction away from the substrate 1801 or 1803 being advanced over the roll to stretch the substrate 1801 or 1803 in the cross-machine direction or generally in the cross-machine direction. In an instance, the roll may comprise two outer longitudinal portions that each may expand in opposite directions generally along the longitudinal axis of the roll. The two outer portions may both be angled downwards in a direction away from the substrate 1801 or 1803 being advanced over the roll. This movement or positioning of the outer longitudinal portions of the roll allows for generally cross-machine directional tensioning of the substrate 1801 or 1803, which may cause any individual fibers of the first region and/or the second region that may have bonded to any adjacent fibers through the deformer roller arrangement 1808, and were not separated during the incremental web stretching apparatus 1832, to pull apart.

The outer longitudinal portions of the roll may comprise vacuum, a low tack adhesive, a high coefficient of friction material or surface, such as rubber, and/or other mechanisms and/or materials to hold the fibrous substrate to the outer lateral portions of the roll during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the fibrous substrate from slipping relative to the longitudinal axis, A, of the roll during stretching of the outer lateral portions of the material in the cross-machine direction or generally in the cross-machine direction.

FIG. 23 is a top perspective view of the example cross-machine directional tensioning apparatus 1832'. The cross-machine directional tensioning apparatus 1832' may comprise a roll comprising a middle portion 2300 and two outer longitudinal portions 2320 situated on either end of the middle portion 2300. The roll may rotate about its longitudinal axis, A, on a drive shaft 2340. The roll may rotate relative to the drive shaft 2340 or in unison with the drive shaft 2340, as will be recognized by those of skill in the art. The patterned substrate 1801 or 1803 may be advanced over the entire cross-machine directional width of the middle portion 2300 and at least portions of the cross-machine directional widths of the outer longitudinal portions 2320. The substrate 1801 or 1803 may be advanced over at least about 5% up to about 80% of the circumference of the roll so that the cross-machine directional stretching may be performed.

Figure 24:
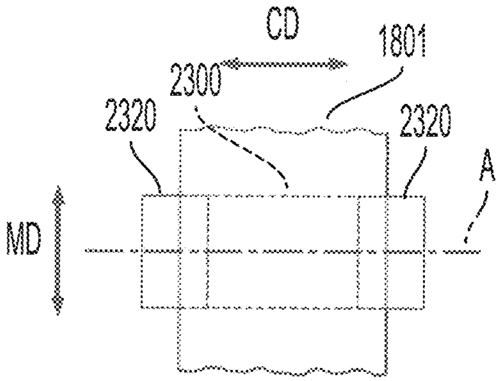
FIG. 24 is a schematic representation of a front view of an example cross-machine directional tensioning apparatus with outer longitudinal portions in an unexpanded and non-angled position relative to a middle portion.
Figure 25:
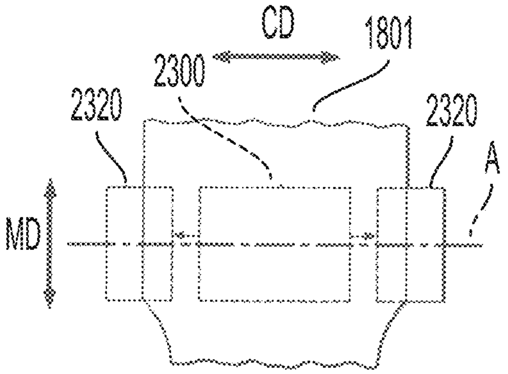
FIG. 25 is a schematic representation of a front view of the cross-machine directional tensioning apparatus of FIG. 24 with the outer longitudinal portions in a longitudinally expanded position relative to the middle portion in accordance with the present disclosure.
Figure 26:
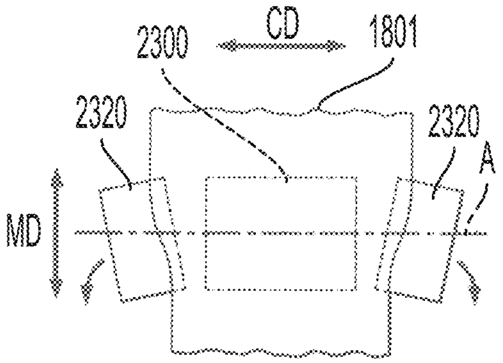
FIG. 26 is a schematic representation of a front view of the cross-machine directional tensioning apparatus of FIG. 24 with the outer longitudinal portions in an angled and expanded position relative to the middle portion.
Figure 27:
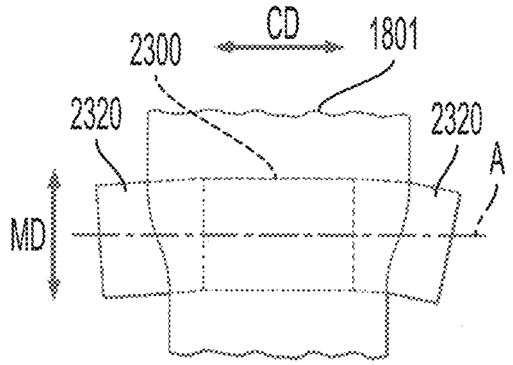
FIG. 27 is a schematic representation of a front view of a cross-machine directional tensioning apparatus with outer longitudinal portions fixed in an angled position relative to a middle portion.

FIG. 24 is a schematic representation of a front view of an example cross-machine directional tensioning apparatus 1832' with outer longitudinal portions 2320 in an unexpanded or non-angled position relative to the middle portion 2300. FIG. 25 is a schematic representation of a front view of the cross-machine directional tensioning apparatus 1832' of FIG. 24 with the outer longitudinal portions 2320 in a longitudinally expanded position relative to the middle portion 2300. FIG. 26 is a schematic representation of a front view of the cross-machine directional tensioning apparatus 1832' of FIG. 24 with the outer longitudinal portions 2320 in an angled and expanded position relative to the middle portion 2300. Regarding FIG. 26, the outer longitudinal portions 2320 may merely move or slide in a direction generally perpendicular to the machine direction of the substrate 1801 or 1803 passing over the roll to apply the cross-machine directional tensioning force to the substrate 1801 or 1803. FIG. 27 is a schematic representation of a front view of a cross-machine directional tensioning apparatus 1832' with the outer longitudinal portions 2320 fixed in an angled position relative to the middle portion 2300 to apply the cross-machine directional tensioning force to the substrate 1801 or 1803. In such a form, the middle portion 2300 and each of the outer longitudinal portions 2320 may comprise a separate roll.

Regardless of whether one or both of the outer longitudinal portions 2320 is moved, slid, rotated, fixed, and/or expanded relative to the middle portion 2300, this relative motion or positioning between the outer longitudinal portions 2320 and the middle portion 2300 stretches the substrate 1801 or 1803 in a cross-machine direction. In an instance, the cross-machine directional tensioning apparatus 1832' may be similar to, or the same as, the incremental stretching apparatus 1832 to apply the cross-machine directional tensioning force. In still other instances, any suitable cross-machine directional tensioning apparatus may be used to apply the cross-machine directional tensioning force to the substrate 1801 or 1803.

If desired, the incremental stretching step or the cross-machine directional stretching step described herein may be performed at elevated temperatures. For example, the regioned fibrous substrate 1803, the patterned fibrous substrate 1801, and/or the rolls may be heated. Utilizing heat in the stretching step may serve to soften the fibrous substrate, and may aid in extending the fibers of the substrate without breaking.

Referring again to FIG. 18, the patterned fibrous substrate 1801 may be taken up on wind-up roll 1880 and stored. Alternatively, the patterned fibrous substrate 1801 may be fed directly to a production line where it is used to form a portion of an absorbent article or other consumer product.

Bio-Based Content for Components

Components of the patterned nonwoven substrates and/or the absorbent articles described herein may at least partially be comprised of bio-based content as described in U.S. Pat. Appl. No. 2007/0219521A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S.A.).

A patterned nonwoven substrate and/or an absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Pat. Appl. Publ. No. 2019/0192723, published on Jun. 27, 2019.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

EXAMPLES

Opacity Measurements

The visual difference between the first regions and the second regions of the patterned fibrous substrates of the present disclosure may be determined using the Opacity Test Method described herein. Briefly, the opacity scores of portions of the first regions of example patterned fibrous substrates (first opacity) are compared to the opacity scores of portions of the second regions (second opacity) to produce a Δ Opacity score and a percent opacity difference for each example patterned fibrous substrate. It is believed that the greater the A opacity score and/or the percent opacity difference is, the greater the visual difference between the first region and the second region of the example patterned fibrous substrate.

Example 1: The patterned fibrous substrate according to the present disclosure described herein as Example 1 is a 22 gsm spunbond nonwoven substrate comprising bicomponent fibers having a core/sheath configuration with 50% polyethylene (sheath) and 50% polypropylene (core), and an average fiber diameter of 22 μm. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.02 inch (0.51 mm) depth of engagement.

Example 2: The patterned fibrous substrate according to the present disclosure described herein as Example 2 is a 24 gsm carded air-through bonded nonwoven substrate comprising bicomponent fibers comprising polyethylene (sheath) and polyethylene terephthalate (PET) (core), and an average fiber diameter of 16 μm. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.015 inch (0.38 mm) depth of engagement.

Example 3: The patterned fibrous substrate according to the present disclosure described herein as Example 3 is a 25 gsm spunbond nonwoven substrate comprising bicomponent fibers having a core/sheath configuration with 70% polyethylene (sheath) and 30% polypropylene (core) and an average fiber diameter of 18 μm, wherein the polypropylene core comprises 5% magenta pigment masterbatch. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.02 inch (0.51 mm) depth of engagement.

Example 4: The patterned fibrous substrate according to the present disclosure described herein as Example 4 is a 50 gsm spunbond nonwoven substrate comprising bicomponent fibers having a core/sheath configuration with 50% polyethylene (sheath) and 50% polypropylene (core) and an average fiber diameter of 21 μm, wherein the polypropylene core comprises 2.5% black pigment masterbatch. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.02 inch (0.51 mm) depth of engagement.

Example 5: The patterned fibrous substrate according to the present disclosure described herein as Example 5 is a 50 gsm spunbond nonwoven substrate comprising bicomponent fibers having a core/sheath configuration with 50% polyethylene (sheath) and 50% polypropylene (core) and an average fiber diameter of 18 μm, wherein no pigment or opacifiers are added to the polypropylene. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.02 inch (0.51 mm) depth of engagement.

Example 6: The patterned fibrous substrate according to the present disclosure described herein as Example 6 is a 50 gsm spunbond nonwoven substrate comprising bicomponent fibers having a core/sheath configuration with 50% polyethylene (sheath) and 50% polypropylene (core) and an average fiber diameter of 18 μm, wherein the polypropylene core comprises 2% yellow pigment masterbatch. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.02 inch (0.51 mm) depth of engagement.

Example 7: The patterned fibrous substrate according to the present disclosure described herein as Example 7 is a 50 gsm spunbond nonwoven substrate comprising bicomponent fibers having a core/sheath configuration with 50% polyethylene (sheath) and 50% polypropylene (core) and an average fiber diameter of 18 μm, wherein the polypropylene core comprises 0.5% teal pigment masterbatch. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.02 inch (0.51 mm) depth of engagement.

TABLE 1

| | Average Fiber Diameter before deformation, μm | Pigment | First Region Opacity | Second Region Opacity | Δ Opacity | Opacity % Difference |
|---|---|---|---|---|---|---|
| Example 1 | 22 | None | 22.5 | 30.5 | 8 | 36% |
| Example 2 | 16 | None | 36.4 | 51.6 | 15.2 | 42% |
| Example 3 | 18 | 5% Magenta | 40.7 | 56.8 | 16.1 | 40% |
| Example 4 | 21 | 2.5% black | 93.8 | 99.1 | 5.3 | 6% |
| Example 5 | 18 | None | 47.1 | 63.8 | 16.7 | 35% |
| Example 6 | 18 | 2% yellow | 61.9 | 72.6 | 10.7 | 17% |
| Example 7 | 18 | 0.5% Teal | 62.2 | 74 | 11.8 | 19% |

As shown in TABLE 1, the opacity of the first region of each patterned fibrous substrate (examples 1-7) is less than the opacity of the second region. In each of examples 1-7, the Δ opacity score was greater than 3, suggesting that the first and second regions would appear different to the human eye.

ΔL* Measurements

The visual difference between the first regions and the second regions of the patterned fibrous substrates of the present disclosure are determined using the Color Test Method described herein. Briefly, the C.I.E. L* scores of portions of the first regions of example patterned fibrous substrates are compared to the C.I.E. L* scores of portions of the second regions to produce a ΔL* score for each example patterned fibrous substrate. The greater the ΔL* score is, the greater the visual difference between the first region and the second region of the example patterned fibrous substrate.

Because non-patterned fibrous substrates may comprise some variability in visual appearance due to, for example, variation in basis weight across the substrate, non-patterned comparative examples are tested. Lighter areas of the non-patterned comparative example are identified as a proxy for a first region, and darker areas are identified as a proxy for a second region.

Example 8: The patterned fibrous substrate according to the present disclosure described herein as Example 8 is a 25 gsm spunbond nonwoven substrate comprising bicomponent fibers having a core/sheath configuration with 70% polyethylene (sheath) and 30% polypropylene (core) and an average fiber diameter of 18 μm, wherein the polypropylene core comprises 5% magenta pigment masterbatch. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.02 inch (0.51 mm) depth of engagement.

Example 9: The patterned fibrous substrate according to the present disclosure described herein as Example 9 is a 50 gsm spunbond nonwoven substrate comprising bicomponent fibers having a core/sheath configuration with 50% polyethylene (sheath) and 50% polypropylene (core) and an average fiber diameter of 21 μm, wherein the polypropylene core comprises 2.5% black pigment masterbatch. The nonwoven substrate is deformed with a patterned plate using a press with a nip pressure of approximately 14,000 psi (96.5 MPa), where the smooth platen is not heated (ambient temperature). The nonwoven is subsequently passed through an incremental stretching system having a 0.040 inch (1.0 mm) pitch and a 0.02 inch (0.51 mm) depth of engagement.

Example 10: the patterned fibrous substrate according to the present disclosure described herein as Example 10 is a 24 gsm carded air-through bonded nonwoven substrate comprising bicomponent fibers comprising polyethylene (sheath) and polyethylene terephthalate (PET) (core), and an average fiber diameter of 16 μm. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.015 inch (0.38 mm) depth of engagement.

Example 11: The patterned fibrous substrate according to the present disclosure described herein as Example 11 is a 25 gsm polypropylene spunbond nonwoven substrate. The nonwoven substrate is passed through a deforming roller arrangement with a nip pressure of approximately 70,000 psi (482.6 MPa), where the patterned roller is at ambient temperature (no heat applied), at approximately 100 feet per minute. The nonwoven is not subsequently passed through an incremental stretching system.

Example 12: The patterned fibrous substrate according to the present disclosure described herein as Example 12 is a 24 gsm carded nonwoven substrate comprising bicomponent fibers comprising polyethylene (sheath) and polyethylene terephthalate (PET) (core). The nonwoven substrate is passed through a deforming roller arrangement with a nip pressure of approximately 70,000 psi, where the patterned roller is at ambient temperature (no heat applied), at approximately 100 feet per minute (30.48 meters per minute). The nonwoven is not subsequently passed through an incremental stretching system.

Comparative Example 1: The fibrous substrate described herein as Comparative Example 1 is a 24 gsm carded nonwoven substrate comprising bicomponent fibers comprising polyethylene (sheath) and polyethylene terephthalate (PET) (core). The substrate is not passed through a deforming roller arrangement or an incremental stretching system.

Comparative Example 2: The fibrous substrate described herein as Comparative Example 2 is a 25 gsm polypropylene spunbond nonwoven substrate. The substrate is not passed through a deforming roller arrangement or an incremental stretching system.

TABLE 2

| | Substrate Color | ΔL* Average |
|---|---|---|
| Example 8 | Magenta | 10.0 |
| Example 9 | Black | 11.7 |
| Example 10 | White | 5.0 |
| Example 11 | White | 7.8 |
| Example 12 | White | 9.4 |
| Comparative Example 1 | White | 0.3 |
| Comparative Example 2 | White | −0.3 |

As shown in TABLE 2, Examples 8-12 of the present disclosure have greater ΔL* Average scores as compared to the Comparative Examples 1 and 2. These data indicate that the first region and the second region of Examples 8-12 are visually discernable to the human eye.

Light Transmission Measurements

Example 13: The patterned fibrous substrate according to the present disclosure described herein as Example 13 is a 24 gsm carded air-through bonded nonwoven substrate comprising bicomponent fibers comprising polyethylene (sheath) and polyethylene terephthalate (PET) (core), and an average fiber diameter of 16 μm. The nonwoven substrate is deformed with a patterned plate using a heated press with a nip pressure of approximately 14,000 psi (96.5 MPa), where the smooth platen is heated to approximately 107° C. The nonwoven is subsequently passed through an incremental stretching system having a 0.040 inch (1.0 mm) pitch and a 0.015 inch (0.38 mm) depth of engagement. The patterning process imparted a pattern of repeating clouds in the substrate, as shown in FIG. 20.

TABLE 3

| First Region of Example 13 | |
|---|---|
| Replicate area 1 avg. L* | 67 |
| Replicate area 2 avg. L* | 69 |
| First Region average L* | 68 |

TABLE 3-continued

| Second Region of Example 13 | |
|---|---|
| Replicate area 1 avg. L* | 54 |
| Replicate area 2 avg. L* | 63 |
| First Region average L* | 58.5 |
| Patterned Fibrous Substrate Example 13 | |
| ΔLT | 9.5 |
| Light Transmission % difference | 14% |

As shown in TABLE 3, the L* values as measured in the first region are greater than the L* values as measured in the second region. The ΔLT and Light Transmission % difference scores suggest that the difference in light transmission between the first region and the second region of the patterned fibrous substrate Example 13 may be visually discernable to the human eye, thereby creating a patterned effect in the substrate.

Fiber Diameter Measurements

Several example patterned fibrous substrates of the present disclosure were measured for fiber diameters of the plurality of individual fibers in the first region and for fiber diameters of the plurality of individual fibers in the second region, according to the Fiber Diameter Test Method disclosed herein. These data are presented in TABLE 4.

Example 14: The patterned fibrous substrate according to the present disclosure described herein as Example 14 is a 25 gsm spunbond nonwoven substrate comprising bicomponent fibers having a core/sheath configuration with 50% polyethylene (sheath) and 50% polypropylene (core), wherein 0.5% $TiO_2$ is present in the polypropylene core. The nonwoven substrate is passed through a deforming roller arrangement with a nip pressure of approximately 50,000 psi (345 MPa), where the patterned roller is at ambient temperature (no heat applied), at approximately 100 feet (30.48 meters) per minute. The nonwoven is subsequently passed through an incremental stretching system having a 0.040 inch (1.0 mm) pitch and a 0.02 inch (0.51 mm) depth of engagement.

Example 15: The patterned fibrous substrate according to the present disclosure described herein as Example 15 is a 24 gsm carded air-through bonded nonwoven substrate comprising bicomponent fibers comprising polyethylene (sheath) and polyethylene terephthalate (PET) (core). The nonwoven substrate is passed through a deforming roller arrangement with a nip pressure of approximately 30,000 psi (206.8 MPa), where the patterned roller is at ambient temperature (no heat applied), at approximately 100 feet (30.48 meters) per minute. The nonwoven is subsequently passed through an incremental stretching system having a 0.040 inch (1.0 mm) pitch and a 0.02 inch (0.51 mm) depth of engagement.

Example 16: The patterned fibrous substrate according to the present disclosure described herein as Example 16 is a 22 gsm spunbond nonwoven substrate comprising bicomponent fibers having a core/sheath configuration with 50% polyethylene (sheath) and 50% polypropylene (core). The nonwoven substrate is passed through a deforming roller arrangement with a nip pressure of approximately 30,000 psi (206.8 MPa), where the patterned roller is at ambient temperature (no heat applied), at approximately 100 feet (30.48 meters) per minute. The nonwoven is subsequently passed through an incremental stretching system having a 0.040 inch (1.0 mm) pitch and a 0.02 inch (0.51 mm) depth of engagement.

TABLE 4

| | Pressure (psi/MPa) | Ring Rolling (yes/no) | First Region Average Fiber Diameter μm | Second Region Average Fiber Diameter μm |
|---|---|---|---|---|
| Example 14 | 50,000/345 | Yes | 14.8 | 19.3 |
| Example 15 | 30,000/206.8 | No | 15.1 | 26.2 |
| Example 16 | 50,000/345 | No | 21.1 | 26.2 |

As shown in TABLE 4, each patterned fibrous substrate example of the present disclosure tested has a second region average fiber diameter greater than a first region average fiber diameter.

Fluid Permeability Measurements

Several example patterned fibrous substrates of the present disclosure were measured for fluid permeability in the first region and in the second region, according to the Fluid Permeability Test Method disclosed herein. These data are presented in TABLE 5.

Example 17: The patterned fibrous substrate according to the present disclosure described herein as Example 17 is a 50 gsm spunbond nonwoven substrate comprising bicomponent fibers having a core/sheath configuration with 50% polyethylene (sheath) and 50% polypropylene (core) wherein the polypropylene core comprises 2.5% black pigment masterbatch. The nonwoven substrate is deformed with a patterned plate press having a cloud pattern, like shown in FIG. 20, with a nip pressure of approximately 14,000 psi (96.5 MPa), where the platen is heated to approximately 225° F. (107° C.). The nonwoven is subsequently passed through an incremental stretching system having a 0.040 inch (1.0 mm) pitch and a 0.02 inch (0.51 mm) depth of engagement.

Example 18: The patterned fibrous substrate according to the present disclosure described herein as Example 18 is a 24 gsm carded air-through bonded nonwoven substrate comprising bicomponent fibers comprising polyethylene (sheath) and polyethylene terephthalate (PET) (core). The nonwoven substrate is deformed with a patterned plate having a cloud pattern, like shown in FIG. 20, with a nip pressure of approximately 14,000 psi (96.5 MPa), where the platen is not heated (ambient temperature). The nonwoven is subsequently passed through an incremental stretching system having a 0.040 inch (1.0 mm) pitch and a 0.015 inch (0.381 mm) depth of engagement.

Example 19: The patterned fibrous substrate according to the present disclosure described herein as Example 19 is a 24 gsm carded air-through bonded nonwoven substrate comprising bicomponent fibers comprising polyethylene (sheath) and polyethylene terephthalate (PET) (core). The nonwoven substrate is deformed with a patterned plate having a cloud pattern, like shown in FIG. 20, with a nip pressure of approximately 2,500 psi (17.2 MPa), where the platen is heated to approximately 225° F. (107° C.). The nonwoven is subsequently passed through an incremental stretching system having a 0.040 inch (1.0 mm) pitch and a 0.015 inch (0.381 mm) depth of engagement.

Example 20: The patterned fibrous substrate according to the present disclosure described herein as Example 20 is a 24 gsm carded air-through bonded nonwoven substrate comprising bicomponent fibers comprising polyethylene (sheath) and polyethylene terephthalate (PET) (core). The nonwoven substrate is deformed with a patterned plate having a cloud pattern, like shown in FIG. 20, with a nip pressure of approximately 14,000 psi (96.5 MPa), where the platen is heated to approximately 225° F. (107° C.). The nonwoven is subsequently passed through an incremental stretching system having a 0.040 inch (1.0 mm) pitch and a 0.015 inch (0.381 mm) depth of engagement.

Example 21: The patterned fibrous substrate according to the present disclosure described herein as Example 21 is a 25 gsm crimped polypropylene spunbond nonwoven substrate. The nonwoven substrate is deformed with a patterned plate having a cloud pattern, like shown in FIG. 20, with a nip pressure of approximately 14,000 psi (96.5 MPa), where the platen is not heated (ambient temperature). The nonwoven is subsequently passed through an incremental stretching system having a 0.040 inch (1.0 mm) pitch and a 0.015 inch (0.381 mm) depth of engagement.

Example 22: The patterned fibrous substrate according to the present disclosure described herein as Example 22 is a 25 gsm crimped polypropylene spunbond nonwoven substrate. The nonwoven substrate is deformed with a patterned plate having a cloud pattern, like shown in FIG. 20, with a nip pressure of approximately 2,500 psi (17.2 MPa), where the platen is heated to approximately 225° F. (107° C.). The nonwoven is subsequently passed through an incremental stretching system having a 0.040 inch (1.0 mm) pitch and a 0.015 inch (0.381 mm) depth of engagement.

Example 23: The patterned fibrous substrate according to the present disclosure described herein as Example 23 is a 25 gsm crimped polypropylene spunbond nonwoven substrate. The nonwoven substrate is deformed with a patterned plate having a cloud pattern, like shown in FIG. 20, with a nip pressure of approximately 14,000 psi (96.5 MPa), where the platen is heated to approximately 225° F. (107° C.). The nonwoven is subsequently passed through an incremental stretching system having a 0.040 inch (1.0 mm) pitch and a 0.015 inch (0.381 mm) depth of engagement.

Example 24: The patterned fibrous substrate according to the present disclosure described herein as Example 24 is a 25 gsm spunbond nonwoven substrate comprising bicomponent fibers having a core/sheath configuration with 50% polyethylene (sheath), 50% polypropylene (core), and 1.5% erucamide in both the sheath and core components. The polypropylene core comprises 0.5% TiO2. The nonwoven substrate is passed through a deforming roller arrangement with a nip pressure of approximately 50,000 psi (345 MPa), where the patterned roller is at ambient temperature (no heat applied), at approximately 100 feet per minute. The nonwoven is not subsequently passed through an incremental stretching system.

Example 25: The patterned fibrous substrate according to the present disclosure described herein as Example 25 is a 25 gsm polypropylene spunbond nonwoven substrate, where the polypropylene fibers comprise 1.5% Erucamide, TiO2, and 10% polyolefin copolymer additive (VISTAMAXX from EXXONMOBILE). The nonwoven substrate is passed through a deforming roller arrangement with a nip pressure of approximately 70,000 psi (482.6 MPa), where the patterned roller is at ambient temperature (no heat applied), at approximately 100 feet per minute. The nonwoven is not subsequently passed through an incremental stretching system.

Example 26: The patterned fibrous substrate according to the present disclosure described herein as Example 26 is a 24 gsm carded air-through bonded nonwoven substrate comprising bicomponent fibers comprising polyethylene (sheath) and polyethylene terephthalate (PET) (core). The nonwoven substrate is passed through a deforming roller arrangement with a nip pressure of approximately 70,000 psi (482.6 MPa), where the patterned roller is at ambient temperature (no heat applied), at approximately 100 feet per minute. The nonwoven is not subsequently passed through an incremental stretching system.

Example 27: The patterned fibrous substrate according to the present disclosure described herein as Example 27 is a 24 gsm carded air-through bonded nonwoven substrate comprising bicomponent fibers comprising polyethylene (sheath) and polyethylene terephthalate (PET) (core). The nonwoven substrate is passed through a deforming roller arrangement with a nip pressure of approximately 30,000 psi (206.8 MPa), where the patterned roller is at ambient temperature (no heat applied), at approximately 100 feet per minute. The nonwoven is not subsequently passed through an incremental stretching system.

TABLE 5

| | Fluid Permeability Score (Darcy) | | | Fluid Permeability Ratio (First |
|---|---|---|---|---|
| | First Region | Second Region | % Difference | Region/Second Region) |
| Example 17 | 62.8 | 7.3 | 88.4 | 8.6 |
| Example 18 | 897.7 | 199.7 | 77.8 | 4.5 |
| Example 19 | 897.7 | 76.4 | 91.5 | 11.8 |
| Example 20 | 897.7 | 113.9 | 87.3 | 7.9 |
| Example 21 | 174.5 | 109.0 | 37.5 | 1.6 |
| Example 22 | 174.5 | 115.2 | 34.0 | 1.5 |
| Example 23 | 174.5 | 58.1 | 66.7 | 3.0 |
| Example 24 | 121.5 | 98.8 | 18.7 | 1.2 |
| Example 25 | 326.5 | 186.0 | 43.0 | 1.8 |
| Example 26 | 749.3 | 11.6 | 98.5 | 64.6 |
| Example 27 | 730.4 | 14.3 | 98.0 | 51.1 |

As shown in TABLE 5, the first region fluid permeability score of each of the patterned fibrous substrate examples is the same as or greater than the second region fluid permeability score, according to the Fluid Permeability Test Method disclosed herein. Additionally, the fluid permeability scores of the first regions and the second regions of all of the examples of the present disclosure are above 5 Darcy, indicating that the first regions and the second regions are generally fluid permeable.

Further Examples

Comparative Example 3: The fibrous substrate described herein as Comparative Example 3 is a 25 gsm spunbond substrate comprising bicomponent fibers having a configuration with 50% polyethylene (sheath) and 50% polypropylene (core). The nonwoven substrate is passed through a deforming roller arrangement with a nip pressure of approximately 50,000 psi (345 MPa), where the patterned roller is at ambient temperature (no heat applied).

Comparative Example 4: The fibrous substrate described herein as Comparative Example 4 is a 22 gsm spunbond substrate comprising bicomponent fibers having a configuration with 50% polyethylene (sheath) and 50% polypropylene (core). The nonwoven substrate is passed through a deforming roller arrangement with a nip pressure of approximately 50,000 psi (345 MPa), where the patterned roller is at ambient temperature (no heat applied).

Comparative Example 5: The fibrous substrate described herein as Comparative Example 5 is a 25 gsm spunbond substrate comprising bicomponent fibers having a configuration with 30% polyethylene (sheath) and 70% polypropylene (core). The nonwoven substrate is passed through a deforming roller arrangement with a nip pressure of approximately 50,000 psi (345 MPa), where the patterned roller is at ambient temperature (no heat applied).

Example 17: The fibrous substrate described herein as Example 17 is a 25 gsm spunbond substrate comprising bicomponent fibers having a configuration with 50% polyethylene sheath and 50% polypropylene core, where both the sheath and the core have 0.5% erucamide. The nonwoven substrate is passed through a deforming roller arrangement with a nip pressure of approximately 50,000 psi (345 MPa), where the patterned roller is at ambient temperature (no heat applied).

Example 18—The fibrous substrate described herein as Example 18 is a 25 gsm spunbond substrate comprising bicomponent fibers having a configuration with 50% polyethylene sheath and 50% polypropylene core, where both the sheath and the core have 1.5% erucamide. The nonwoven substrate is passed through a deforming roller arrangement with a nip pressure of approximately 50,000 psi (345 MPa), where the patterned roller is at ambient temperature (no heat applied).

Example 19: The fibrous substrate described herein as Example 19 is a 25 gsm spunbond substrate comprising bicomponent fibers having a configuration with 30% polyethylene sheath and 70% polypropylene core, where the sheath has 17% glyceryl tristearate added to the masterbatch. The nonwoven substrate is passed through a deforming roller arrangement with a nip pressure of approximately 50,000 psi (345 MPa), where the patterned roller is at ambient temperature (no heat applied).

Example 20: The fibrous substrate described herein as Example 20 is a 22 gsm spunbond substrate comprising bicomponent fibers having a configuration with 50% polyethylene (sheath) and 50% polypropylene (core), and a cationic siloxanes (such as SILASTOL PHP26 from SCHILL+SEILACHER GmbH, Boeblingen, Germany) kiss coated onto the substrate at 2.4 weight percent.

Example 21: The fibrous substrate described herein as Example 21 is a 25 gsm spunbond substrate comprising bicomponent fibers having a configuration with 50% polyethylene (sheath) and 50% polypropylene (core). The nonwoven substrate is passed through a deforming roller arrangement with a nip pressure of approximately 50,000 psi (345 MPa), where the patterned roller is at ambient temperature (no heat applied). The nonwoven is subsequently passed through an incremental stretching system having a 0.040 inch (1.0 mm) pitch and a 0.02 inch (0.51 mm) depth of engagement.

TABLE 6

| | ΔL* |
|---|---|
| Comparative Example 3 | 7.1 |
| Comparative Example 4 | 1.4 |
| Comparative Example 5 | 3.5 |
| Example 17 | 10.1 |
| Example 18 | 9.8 |
| Example 19 | 6.7 |
| Example 20 | 12.0 |
| Example 21 | 9.2 |

As shown in TABLE 6, the ΔL* scores of all of the examples of the patterned substrates of the present disclosure are greater than 4 (and greater than 6), demonstrating that these is a visual distinction between the first region and the second region of each substrate. Of note, the ΔL* score of comparative example 3 is also greater than 4. Comparative example 3, however, has very low liquid permeability in the second region of the patterned fibrous substrate, as shown in TABLE 7 and discussed further below.

TABLE 7

| | Air Permeability (m3/m2/min) | |
|---|---|---|
| | Unpatterned | Patterned |
| Comparative Example 3 | 119 | 94 |
| Example 18 | 113 | 112 |
| | First Region | Second Region |
| | Liquid Permeability (Darcy) | |
| Comparative Example 3 | 287 | 1.4 |
| Example 18 | 121 | 98.8 |
| | Caliper (mm) | |
| Comparative Example 3 | 0.31 | 0.04 |
| Example 18 | 0.38 | 0.38 |

As shown in TABLE 7, Example 18 exhibits much less difference in the functional parameters of air permeability, liquid permeability, and caliper between the unpatterned and patterned substrates or the first region and the second region of the patterned fibrous substrate as compared to Comparative Example 3. Example 17-20 comprise a functional surface additive and did not undergo an incremental stretching process after the application of pressure to form a second region within each substrate. Example 21 does not comprise a functional surface additive but did undergo an incremental stretching process after the application of pressure. The comparative examples 3-5 do not comprise a functional surface additive and did not undergo an incremental stretching process after the application of pressure. Without wishing to be bound by theory, it is believed that the addition of a functional surface additive to the composition of the patterned fibrous substrates of the present disclosure (either as a melt additive or as a topical additive) reduces or prevents individual fibers of the patterned fibrous substrate from fusing or otherwise consolidating with other fibers without the need for the patterned fibrous substrates to be subjected to an incremental stretching process to separate fibers. A reduction or inhibition in fusing or consolidating of fibers is believed to result in higher air permeability and liquid permeability scores—scores similar to the first region of the substrate not subjected to the application of pressure—which may result in a substrate more suitable for fluid-handling components of an absorbent article. Maintenance of a caliper in the second region similar to the caliper of the first region may result in a softer-feeling patterned fibrous substrate, which may be more suitable as a component of an absorbent article that comes into contact with the skin of a wearer or user, such as a topsheet or outer cover. Substrates with consolidated (fused) fibers and reduced caliper often have a hard, plastic feel against the skin.

TABLE 8

| | MD Tensile Peak Load (N) |
|---|---|
| Comparative Example 3 | 59.5 |
| Example 18 | 56.6 |
| Comparative Example 4 | 26.1 |
| Example 20 | 26.7 |

As shown in TABLE 8, the MD tensile peak load, an indication of substrate strength and integrity, is similar in Example 18 and Comparative Example 3, and likewise in Example 20 and Comparative Example 4. Example 18 and Comparative Example 3 are comprised of the same fiber formulation, with the exception that Example 18 also contains a functional surface additive. Example 20 and Comparative Example 4 likewise are comprised of the same fiber formulation, with the exception that Example 20 also contains a functional surface additive. The data presented in TABLE 8, therefore, demonstrate that, while the functional surface additive is believed to keep individual fibers separate—especially in the second region of the substrate that is subjected to pressure—the functional surface additive does not impact the primary bonding of the patterned fibrous substrates, thus allowing the substrate to maintain similar strength and integrity (as shown by the MD Tensile Peak Load data in TABLE 8) as substrates devoid of a functional surface additive.

Test Methods

Light Transmission Test Method.

The light transmission test method measures the average amount of light transmitted through specific regions of a patterned fibrous substrate specimen. A calibrated light transmission image is obtained using a flatbed scanner and color management software. The color calibrated image is analyzed using image analysis software.

Sample Preparation:

To obtain a sample for measurement, lay a single layer of the dry substrate raw material out flat and cut to an appropriate size for analysis.

If the substrate material is a layer of an absorbent article, for example a topsheet, backsheet nonwoven, acquisition layer, distribution layer. or another component layer; tape the absorbent article to a rigid flat surface in a planar configuration. Carefully separate the individual substrate layer from the absorbent article. A scalpel and/or cryogenic spray (such as Cyto-Freeze, Control Company, Houston Tex.) can be used to remove a substrate layer from additional underlying layers, if necessary, to avoid any longitudinal and lateral extension of the material.

If the substrate material is in the form of a wet wipe, open a new package of wet wipes and remove the entire stack from the package. Remove a single wipe from the middle of the stack, lay it out flat and allow it to dry completely prior to analysis.

A sample may be obtained from any location containing the visually discernible areas to be analyzed. An area may be visually discernable due to changes in texture, height, specular light reflectance, gloss, color, tone, or thickness. Care should be taken to avoid folds, wrinkles or tears when selecting a location for sampling and analysis.

Condition the samples at about 23° C.±2 C.° and about 50%±2% relative humidity for 2 hours prior to testing.

Light Transmission Image:

The light transmission measurement is based on the CIE L*a*b* color system (CIELAB). A flatbed scanner capable of scanning a minimum of 24-bit color at 800 dpi and has manual control of color management (a suitable scanner is an Epson Perfection V750 Pro from Epson America Inc., Long Beach Calif. or equivalent) is used to acquire images. The scanner is interfaced with a computer running color management software (suitable color management software is MonacoEZColor available from X-Rite Grand Rapids, MI. or equivalent). The scanner is calibrated against a color transparency target and corresponding reference file compliant with ANSI method IT8.7/1-1993 using the color management software to construct a calibrated color profile. The resulting calibrated scanner profile is used to color correct an image from a test specimen within an image analysis program that supports sampling in CIE L*a*b* (a suitable program is Photoshop S4 available from Adobe Systems Inc., San Jose, CA or equivalent). All testing is performed in a conditioned room maintained at about 23±2° C. and about 50±2% relative humidity.

Turn on the scanner for 30 minutes prior to calibration. Deselect any automatic color correction or color management options that may be included in the scanner software. If the automatic color management cannot be disabled, the scanner is not appropriate for this application. Place the IT8 target face down onto the scanner glass, close the scanner lid, acquire an image at 300 dpi and 24-bit color and remove the IT8 target. Open the image file on the computer with the color management software. Follow the recommended steps within the color management software to create and export a calibrated color profile. These steps may include, ensuring that the scanned image is oriented and cropped correctly. The calibrated color profile must be compatible with the image analysis program. The color management software uses the acquired image to compare with the included reference file to create and export the calibrated color profile. After the profile is created the scan resolution (dpi) for test specimens can be changed, but all other settings must be kept constant while imaging specimens.

Open the scanner lid and place the specimen flat against the scanner glass with the outward facing surface facing the glass. Acquire and import a scan of the specimen region within the interior of the frame into the image analysis software at 24-bit color and at 800 dpi in transparency mode. If necessary, crop image to a rectangular field of view circumscribing the apertured region. Transparency mode illuminates the specimen from one side with the sensor capturing the image from the opposite side. Assign the calibrated color profile to the image and change the color space mode to L*a*b* Color corresponding to the CIE L*a*b* standard. This produces a color corrected image for analysis.

Analysis of Light Transmission Image:

To analyze the specimen light transmission image, first separate the L*, a* and b* channels, and select only the L* channel for analysis. Begin by identifying the boundaries of a selected region. The boundary of a region is identified by visual discernment of differences in physical properties when compared to other regions within the sample. For example, a region boundary can be identified based by visually discerning a color change when compared to another region in the sample. Differences in physical properties such as specular reflection of light or fiber shape can be used to discern region boundaries on either the physical sample itself, cross-sectional images, topography images, or light reflection images.

Using the image analysis software, manually draw the largest circular ROI inscribed within the identified region. The average L* values from within the ROI is measured and recorded. This procedure is repeated at two other identified replicate areas, with their average L* values measured and recorded accordingly. An example is shown in FIG. 30. The arithmetic mean of the three recorded values from each of the three distinct replicate regions is calculated and reported as the light transmission value to the nearest tenth.

Opacity Test Method:

Opacity by contrast ratio measurements are made using a 0°/45° spectrophotometer with adjustable apertures capable of making standard CIE color measurements using XYZ coordinates. An example of a suitable spectrophotometer is the Labscan XE (available from Hunter Associates Laboratory, Inc., Reston, VA, or equivalent). Measurements are conducted on a single layer of patterned fibrous substrate test material. All testing is performed in a room maintained at a temperature of 23° C.±2.0° C. and a relative humidity of 50%±2% and samples are conditioned under the same environmental conditions for at least 2 hours prior to testing.

Obtain a sample patterned fibrous substrate. To obtain a sample from an absorbent article, first identify the portion of the absorbent article of interest. Carefully remove the sample of patterned fibrous material from the absorbent article. A cryogenic spray (such as Cyto-Freeze, Control Company, Houston Tex.) can be used to remove the sample from the underlying and overlaying layers if necessary. Identify a first region(s) and a second region(s) of the patterned fibrous substrate. The first region(s) and the second region(s) are visually different from each other in at least one of color, opacity, tone, shade, gloss, and/or reflectance. If the sample at the testing site contains any holes, tears, or other physical deformations, another site is to be selected. Ensure that all adhesive has been completely removed from the testing site. Obtain a sufficient quantity of the patterned fibrous substrate sample material such that ten replicate measurements can be made on each first region(s) and second region(s).

To measure Opacity, select the disk with the largest measurement port size that can fit within the selected first region. Calibrate and standardize the instrument per the vendor instructions using the standard white and black tiles provided by the vendor. Set the spectrophotometer to use the CIE XYZ color space with a D65 standard illumination, a 10° observer, and set the UV filter to nominal. Place the garment-facing surface of the test sample over the aperture and ensure that the entire aperture opening is covered by the testing site graphic. Place the standard white tile directly against the back side of the sample, take a reading and record the Y value as $Y_{white\ backing}$ to the nearest 0.01 units. Without moving the position of the test sample, remove the standard white tile and replace it with the black standard tile. Take a reading and record the Y value as $Y_{black\ backing}$ to the nearest 0.01 units. Calculate Opacity by dividing the $Y_{black\ backing}$ value by the $Y_{white\ backing}$ value and then multiply by 100. Record Opacity to the nearest 0.1 percent.

In like fashion, repeat the testing procedure for a total of ten on different locations within the first region(s). Calculate the arithmetic mean for Opacity obtained from all ten measurements and report to the nearest 0.1 percent as First Opacity.

Using the same prepared patterned fibrous substrate samples, repeat the testing procedure on ten replicate second region(s). Calculate the arithmetic mean for Opacity obtained from all ten measurements and report to the nearest 0.1 percent as Second Opacity.

Report the difference between the First Opacity and the Second Opacity as A Opacity to the nearest 0.1 percent.

Color Test Method:

The Color Test Method measures the C.I.E. L*a*b* color space values (scores) of an identified, visually discernable, region on the surface of a patterned fibrous substrate. A flatbed scanner capable of scanning a minimum of 24-bit color at 800 dpi with manual control of color management (a suitable scanner is an Epson Perfection V850 Pro from Epson America Inc., Long Beach Calif., or equivalent) is used to acquire images of the patterned fibrous substrate. The scanner is interfaced with a computer running color calibration software capable of calibrating the scanner against a color reflection IT8 target utilizing a corresponding reference file compliant with ANSI method IT8.7/2-1993 (a suitable color calibration software is i1 Profiler available from X-Rite Grand Rapids, MI, or equivalent). The color calibration software constructs an International Color Consortium (ICC) color profile for the scanner, which is used to color correct the output images. The color corrected images are then converted into the C.I.E. L*a*b* color space for subsequent color analysis (a suitable image color analysis software is ImageJ v. 1.52 or equivalent, National Institute of Health, USA).

Sample Preparation:

To obtain a sample for measurement, lay a single layer of the dry substrate raw material out flat and cut to an appropriate size for analysis.

If the substrate material is a layer of an absorbent article, for example a topsheet, backsheet nonwoven, acquisition layer, distribution layer, or another component layer; tape the absorbent article to a rigid flat surface in a planar configuration. Carefully separate the individual substrate layer from the absorbent article. A scalpel and/or cryogenic spray (such as Cyto-Freeze, Control Company, Houston Tex.) can be used to remove a substrate layer from additional underlying layers, if necessary, to avoid any longitudinal and lateral extension of the material.

If the substrate material is in the form of a wet wipe, open a new package of wet wipes and remove the entire stack from the package. Remove a single wipe from the middle of the stack, lay it out flat and allow it to dry completely prior to analysis.

A sample may be obtained from any location containing the visually discernible areas to be analyzed. An area may be visually discernable due to changes in texture, height, specular light reflectance, or thickness. Care should be taken to avoid folds, wrinkles or tears when selecting a location for sampling and analysis.

Image Acquisition:

The scanner is turned on 30 minutes prior to calibration and image acquisition. Deselect any automatic color correction or color management options that may be included in the scanner software. If the automatic color management cannot be disabled, the scanner is not appropriate for this application. The recommended procedures of the color calibration software are followed to create and export an ICC color profile for the scanner. The color calibration software compares an acquired IT8 target image to a corresponding reference file to create and export the ICC color profile for the scanner, which will be applied by the scanner image acquisition software to correct the color of subsequent output images.

The scanner lid is opened, and the sample carefully laid flat on the center of the scanner glass with the surface to be analyzed oriented toward the glass. The sample is backed with a black background and the scanner lid closed. A scanned image containing the region to be analyzed is acquired and imported into the image analysis software at 24-bit color with a resolution of 800 dpi (approximately 31.5 pixels per mm) in reflectance mode. The ICC color profile is assigned to the image producing a color corrected sRGB image. This calibrated image is saved in an uncompressed format to retain the calibrated R,G,B color values, such as a TIFF file, prior to analysis.

The sRGB color calibrated image is opened in the color analysis software and converted into the C.I.E. L*a*b* color space. This is accomplished by the following procedure. First, the sRGB data is scaled into a range of [0, 1] by dividing each of the values by 255. Then the companded sRGB channels (denoted with upper case (R,G,B), or generically V) are linearized (denoted with lower case (r,g,b), or generically v) as the following operation is performed on all three channels (R, G, and B):

$$V \in \{R, G, B\}$$

$$v \in \{r, g, b\}$$

$$v = \begin{Bmatrix} \dfrac{V}{12.92} & \text{if } V \le 0.04045 \\ \left(\dfrac{V + 0.055}{1.055}\right)^{2.4} & \text{otherwise} \end{Bmatrix}$$

The linear r, g, and b values are then multiplied by a matrix to obtain the XYZ Tristimulus values according to the following formula:

$$\begin{bmatrix} X \\ Y \\ Z \end{bmatrix} = \begin{bmatrix} 0.4124 & 0.3576 & 0.1805 \\ 0.2126 & 0.7152 & 0.0722 \\ 0.0193 & 0.1192 & 0.9505 \end{bmatrix} \begin{bmatrix} r \\ g \\ b \end{bmatrix}$$

The XYZ Tristimulus values are rescaled by multiplying the values by 100, and then converted into CIE 1976 L*a*b* values as defined in CIE 15:2004 section 8.2.1.1 using D65 reference white.

C.I.E. L*a*b* Measurement:

To analyze the C.I.E. L*a*b* color values (scores), begin by identifying the boundary of a selected region. The boundary of a region is identified by visual discernment of differences in physical properties when compared to other regions within the sample. For example, a region boundary can be identified based by visually discerning a color change when compared to another region in the sample. Differences in physical properties such as specular reflection of light or fiber shape can be used to discern region boundaries on either the physical sample itself, cross-sectional images, topography images, or light reflection images.

Using the image analysis software, manually draw the largest circular ROI that can be inscribed within the boundaries of the selected region. The average C.I.E. L*, a*, and b* values are measured from within the ROI. This procedure is repeated at fourteen other identified substantially similar replicate regions with their C.I.E. L*, a*, and b* values measured and recorded accordingly. The arithmetic mean of the fifteen recorded L*, a*, and b* values for the region is calculated and reported as its L*, a*, and b* scores to the nearest tenth.

Color ΔE Measurement:

The average L*, a*, and b* values within the inscribed circular ROI drawn within a first region is measured and identified as $L^*_1$, $a^*_1$, and $b^*_1$. The average L*, a*, and b* values are then measured for a second inscribed circular ROI drawn within the boundaries of a second region, and identified as $L^*_2$, $a^*_2$, and $b^*_2$. The ΔE value is then calculated according to the following equation:

$$\Delta E=\sqrt{(L^*_2-L^*_1)^2+(a^*_2-a^*_1)^2+(b^*_2-b^*_1)^2}$$

This procedure is repeated at fourteen other identified replicate regions and ΔE measured and recorded accordingly. The arithmetic mean of the fifteen recorded ΔE values is calculated and reported as their ΔE value to the nearest tenth.

Fiber Diameter Test Method

A Scanning Electron Microscope (SEM) is used to obtain images of the first and/or the second side of a patterned fibrous substrate test sample. From these images, the diameter of the individual fibers of the first region and the second region is determined using image analysis. As used herein, the term "diameter" means the distance between two opposing sides of a fiber as measured using the Fiber Diameter Test Method. All testing is performed in a room maintained at a temperature of 23° C.±2.0° C. and a relative humidity of 50%±2% and samples are conditioned under the same environmental conditions for at least 2 hours prior to testing. Obtain a test sample by removing it from an absorbent article, if necessary. When excising the sample from an absorbent article, use care to not impart any contamination or distortion to the sample layer during the process. The test sample is obtained from an area free of folds or wrinkles. A total of 6 replicate test samples are obtained.

Secondary Electron (SE) images are obtained using an SEM such as the FEI Quanta 450 (available from FEI Company, Hillsboro, OR), or equivalent. The instrument is calibrated according to the manufacturer's instructions prior to use to ensure an accurate distance scale. The test region on the first region of the test sample is viewed at an appropriate magnification (e.g. 1000×; horizontal field width about 200 microns) such that the size (diameter) of the filaments can accurately be measured, and an image is acquired. At a second region of the same test sample, an image of the second region of the test sample is acquired using the same magnification used for the first region.

The image of the first region of the test sample is opened on a computer running image analysis software, such as Image Pro Plus (available from Media Cybernetics, Rockville, MD), or equivalent. The calibrated distance scale is used to measure the diameter of 5 individual fibers of the first region, and these values are recorded as First Region Individual Fiber Diameters, to the nearest 0.01 micron. The diameter of each individual fiber is measured at a location that is perpendicular to the fiber length at each specific measurement location. In like fashion, the individual fiber diameters from the second region are measured on the image of the second region of the test sample, and each recorded to the nearest 0.01 micron.

In like fashion, repeat all measurements for a total of 6 replicate test samples. Calculate the arithmetic mean for first diameter (arithmetic mean of diameter values for individual fibers of the first region) and second diameter (arithmetic mean of diameter values for individual fibers of the second region) obtained for all 6 replicates and report to the nearest 1 unit.

Aspect Ratio Test Method

A Scanning Electron Microscope (SEM) is used to obtain images of a cross-section of a fibrous substrate test sample. From these images, the cross-sectional heights and cross-sectional widths of individual fibers in the first region(s) and the second region(s) of patterned fibrous substrates are determined using image analysis. The first region(s) and the second region(s) are visually different from each other in at least one of color, opacity, tone, shade, gloss, and/or reflectance. All testing is performed in a room maintained at a temperature of 23° C.±2.0° C. and a relative humidity of 50%±2% and samples are conditioned under the same environmental conditions for at least 2 hours prior to testing.

Obtain a test sample by removing it from an absorbent article, if necessary. When excising the sample from an absorbent article, use care to not impart any contamination or distortion to the sample layer during the process. The test sample is obtained from an area free of folds or wrinkles. A total of 6 replicate test samples are obtained. Each test sample is bisected in the first region and the second region, and the test regions are the cross-section of the patterned fibrous substrate at the first and second region for each test sample.

Secondary Electron (SE) images are obtained using an SEM such as the FEI Quanta 450 (available from FEI Company, Hillsboro, OR), or equivalent. The instrument is calibrated according to the manufacturer's instructions prior to use to ensure an accurate distance scale. The cross-section test region of the test sample is viewed at appropriate magnification (e.g., 1000×; horizontal field width about 100 microns) such that the cross-sectional height and cross-sectional width of the fibers can accurately be measured, and an image is acquired. "Cross-sectional width," as used herein, means the largest cross-sectional dimension of an individual fiber, regardless of the orientation of the fiber to other fibers or to the plane of the patterned fibrous substrate. "Cross-sectional height," as used herein, means the cross-sectional dimension that is perpendicular to the fiber cross-sectional width. An image of the second region of the test sample is acquired using the same magnification used for the first region test region.

In like fashion, repeat all measurements on the first region and second region for a total of 6 replicate test samples. Calculate the aspect ratio (cross-sectional width/cross-sectional height) for each region of each test sample. Calculate the arithmetic mean for the aspect ratio of the first region and the arithmetic mean for the aspect ratio of the second region from data obtained for all 6 replicate test samples.

Fluid Permeability Test Method

In the Fluid Permeability Test Method, a region of interest of a nonwoven substrate is structurally characterized using three-dimensional X-ray micro computed tomography (microCT), and the Stokes equations for incompressible Newtonian fluid flow are used to calculate a fluid flow field through the structure, which in turn can be used to calculate a permeability score according to Darcy's Law for that region of interest. In this method, reference to the "z axis" generally refers to the axis perpendicular to the plane of the nonwoven and the "x axis" and "y axis" generally together refer to two orthogonal axes that together define the plane of the nonwoven region of interest.

A region of interest is identified and is excised within a portion sized suitably for analysis with microCT. MicroCT is then performed on the flat excised portion so as enable a three-dimensional structural rendering, centered on the region of interest, and measuring 2.0 mm×2.0 mm in the plane of the nonwoven and encompasses the entire thickness of the nonwoven. The resolution of the microCT structural rendering in each dimension is 4.0 μm or better (that is, each voxel measures 4.0 μm or less along each edge).

One exemplary sample preparation, microCT apparatus, instrument settings, and workflow is the following. The microCT instrument used is a Scanco μCT 50 (available from Scanco Medical AG, Switzerland) or equivalent. A 16-mm specimen disk of nonwoven material is punched, centered on the center of the nonwoven region of interest. The excised nonwoven is placed into an appropriate holder between two rings of low-density foam (such as melamine formaldehyde acoustic foam) with 12-mm inside diameter such that the nonwoven is held flat. This allows the central portion of the sample to lay horizontal and be scanned without having any other materials directly adjacent to its upper and lower surfaces.

The 3D image field of view is approximately 13.6 mm on each side in the xy-plane with a resolution of approximately 3400 by 3400 pixels, and with a sufficient number of 4-μm-thick slices collected to fully include the z-direction of the nonwoven specimen. Projection images are acquired with the source at approximately 45 kVp and 133 μA with no additional low energy filter. These current and voltage settings are optimized to produce the maximum contrast in the projection data with sufficient x-ray penetration through the sample, but once optimized held constant for all substantially similar samples. A total of 1700 projection images are obtained with an integration time of 500 ms and 4 averages. The set of projection images are reconstructed using a Feldkamp-type approach into the 3D image of voxels 4.0 μm on all edges and saved in 16-bit format to preserve the full detector output signal for analysis.

If the microCT data are collected and reconstructed so as to result in a higher resolution (less than 4.0 μm) in any dimension, data are downsampled via tricubic interpolation to arrive at a rendering with 4.0 μm resolution in each dimension. The reconstructed microCT data are then thresholded to arrive at a three-dimensions binary rendering of the nonwoven structure. In this data set, voxels of value 1 correspond to the presence of fiber material, and voxels with a value of 0 correspond to voids absent fiber material. This binary structure, with 4.0 μm resolution in each dimension, is the starting point for the subsequent portions of this method.

The three-dimensional binary structure obtained from microCT is then used directly to define a mesh (4.0 μm in each dimension) of fibers and voids for use in flow calculations. Flow through the structure is considered for an incompressible Newtonian fluid approximating water (density of 103 kg/m3, viscosity of 10−3 Pa s), assuming no slip at the interface of fluid and fibers, and the fibers are assumed to be arbitrarily rigid throughout the calculation. Specifically, the Stokes momentum equation for such a fluid flowing through a nonwoven simplifies to $$\nabla p_9=\mu\nabla^\wedge 2u^{\rightarrow},$$

where p is pressure (Pa), μ is the fluid's dynamic viscosity (Pa s), and u is fluid velocity (m s−1). For this calculation, the mesh derived from microCT is augmented along the z axis such that the mesh is about 1.0 mm in the z axis with the nonwoven is lying approximately at the center of the z dimension. A pressure drop of about 0.02 Pa across the entire z dimension is used, with a periodic boundary condition applied in the z dimension and symmetric boundary conditions applied in x and y. This equation is typically solved numerically over the three-dimensional mesh using a second-order PDE solver and/or computational fluid dynamics software.

One suitable implementation of this calculation is with GeoDict (Math2Market, Kaiserslautern, Germany). The FlowDict module is used for the calculation. MicroCT data in the *.raw format are imported, and 100 voxels of mesh padding are added on each side of the initial mesh such that the overall mesh to be used measured approximately 1.0 mm along the z axis. The "Stokes(-Brinkman) (LIR)" equation option is chosen. In the solver options, an implicit inflow and outflow of 10 voxels is used. All solver defaults are accepted.

The calculated three-dimensional velocity field is then used to determine the permeability of the nonwoven region of interest according to Darcy's Law, which states $$u=-k/\mu\nabla p,$$

where once again p is pressure, μ is the fluid's dynamic viscosity, and u is fluid velocity, and additionally, k is the permeability (in Darcy, where 1 Darcy=9.869233×10−13 m2). In this method, Darcy's Law is applied along the z axis only and is oriented to pertain the pressure drop in the calculation, which in general is almost entirely across the nonwoven. As a result, the simplified equation for Darcy's Law for this method is $$u=-k/\mu L\Delta p,$$

where (1) the value of u is the volume average of the component of velocity parallel to the z axis at all points in the mesh, (2) Δp is the entire pressure drop specifically used in the model (about 0.02 Pa), and (3) L is the thickness of the nonwoven at the center of the region of interest.

The resulting value of permeability k for the nonwoven region of interest is reported as this region's permeability score in units of Darcy to the nearest 0.1 Darcy.

Gloss Measurement Test Method

Measurements for Gloss are made on patterned fibrous substrate test samples that may be removed from absorbent articles, if necessary. When excising the sample from an absorbent article, use care to not impart any contamination or distortion to the sample layer during the process. The test sample is obtained from an area free of folds or wrinkles. A total of 6 replicate test samples are obtained.

Gloss is measured using a gloss meter, such as the Elcometer 480 Glossmeter, available from Elcometer®, Warren, Michigan, U.S.A. In order to determine the most appropriate measurement angle, take an initial measurement set at a 60° angle of incidence. If the result is between 10 GU and 70 GU, the 60° angle of incidence is appropriate. If the result is less than 10 GU, the test sample should be remeasured using an 85° angle of incidence. If the result is greater than 70 GU, the test sample should be remeasured using a 20° angle of incidence. The first region of the test sample is measured for gloss as described above. In like fashion, gloss is measured at the second region of the test sample, and each recorded to the nearest 1 GU with the accompanying angle of incidence.

Method Combinations

B1. A method of making a patterned fibrous substrate comprising the steps of:
 - providing a fibrous substrate comprising a plurality of individual fibers; and
 - applying a distorting force to a portion of the fibrous substrate to create a first region and a second region in the fibrous substrate to form a patterned fibrous substrate, wherein a plurality of fibers of the first region have a first diameter according to the Fiber Diameter Test Method, wherein a plurality of fibers of the second region have a second diameter according to the Fiber Diameter Test Method, and wherein the first diameter is less than the second diameter;
 - wherein the first region has a first C.I.E. L* score, according to the Color Test Method;
 - wherein the second region has a second C.I.E. L* score, according to the Color Test Method;
 - and wherein the first C.I.E. L* score is different than the second C.I.E. L* score.

B2. The method of paragraph B1, wherein the fibers of the first region and the fibers of the second region are substantially free of bonds.

B3. The method of paragraph B1, wherein the fibrous substrate comprises a plurality of primary bonds distributed throughout the fibrous substrate, and wherein the fibers of the first region and the fibers of the second region are substantially free of bonds between the primary bonds.

B4. The method of any of paragraphs B1-B3, wherein the distorting force comprises pressure applied to at least a portion of the fibrous substrate by one or more deforming roller arrangement.

B5. The method of paragraphs B4, wherein the pressure applied to at least a portion of the fibrous substrate by the one or more deforming roller arrangements is from about 2,500 psi to about 70,000 psi, from about 10,000 psi to about 70,000 psi, from about 25,000 psi to about 70,000 psi, or from about 30,000 psi to about 70,000 psi.

B6. The method of any of paragraphs B1-B5, wherein the plurality of individual fibers comprise bi-component fibers having a sheath/core structure, wherein a sheath of the fibers comprise polyethylene, and wherein a core of the fibers comprise polypropylene.

B7. The method of paragraph B6, wherein the bi-component fibers are spunbond.

B8. The method of paragraph B7, wherein the fibrous substrate consists of the spunbond bi-component polyethylene/polypropylene fibers.

B9. The method of any of paragraphs B6-B8, wherein the pressure applied to at least a portion of the fibrous substrate by the one or more deforming roller arrangements is from about 14,000 psi to about 70,000 psi, from about 25,000 psi to about 50,000 psi, or from about 30,000 psi to about 40,000 psi.

B10. The method of any of paragraphs B1-B5, wherein the plurality of individual fibers comprise mono-component polypropylene fibers.

B11. The method of paragraph B10, wherein the mono-component polypropylene fibers are spunbond.

B12. The method of paragraph B11, wherein the fibrous substrate consists of the spunbond mono-component polypropylene fibers.

B13. The method of any of paragraphs B1-B5, wherein the plurality of individual fibers comprise bi-component fibers having a sheath/core structure, wherein a sheath of the fibers comprise polyethylene, and wherein a core of the fibers comprise polyester.

B14. The method of paragraph B13, wherein the fibrous substrate consists of bi-component polyethylene/polyester fibers.

B15. The method of any of paragraphs B10-B14, wherein the pressure applied to at least a portion of the fibrous substrate by the one or more deforming roller arrangements is from about 2,500 psi to about 70,000 psi, from about 30,000 psi to about 70,000 psi, or from about 50,000 psi to about 70,000 psi.

B16. The method of any of paragraphs B1-B15, wherein the distorting force comprises heat applied to at least a portion of the fibrous substrate by the one or more deforming roller arrangements, wherein the heat applied to at least a portion of the fibrous substrate is from about 50° C. to about 180° C., from about 80° C. to about 150° C., or from about 100° C. to about 130° C.

B17. The method of paragraph B16, wherein the pressure applied to at least a portion of the fibrous substrate by the one or more deforming roller arrangements is from about 2,500 psi to about 50,000 psi, from about 10,000 psi to about 35,000 psi, or from about 15,000 to about 25,000 psi.

B18. The method of any of paragraphs B1-B17, comprising the step of extending the fibrous substrate in a machine direction and/or a cross-machine direction.

B19. The method of paragraph B18, further comprising stretching the fibrous substrate by one or more incremental web stretching apparatus.

B20. The method of paragraph B19, wherein the incremental web stretching apparatus has a pitch of between about 0.5 mm to about 10 mm, between about 1 mm and about 5 mm, or between about 1 mm and about 1.5 mm.

B21. The method of any of paragraphs B19 and B20, wherein the incremental web stretching apparatus has a depth of engagement of between about 0.005 inches to about 0.2 inches, between about 0.01 inches to about 0.1 inches, or between about 0.015 inches to about 0.07 inches.

B22. The method of any of paragraphs B1-B21, wherein the fibrous substrate is formed from a single fibrous web.

B23. The method of any of paragraphs B1-B22, wherein the first region does not overlap the second region.

B24. The method of any of paragraphs B1-B23, wherein the second region forms a recognizable design in the fibrous substrate.

B25. The method of any of paragraphs B1-B24, wherein the fibrous substrate is a nonwoven substrate.

B26. The method of any of paragraphs B1-B25, wherein the first region has a first opacity, according to the Opacity Test Method; wherein the second region has a second opacity, according to the Opacity Test Method; and wherein the first opacity is different than the second opacity.

In like fashion, repeat all measurements for a total of 6 replicate test samples. Calculate the arithmetic mean for first region gloss (arithmetic mean of gloss values of the first region) and second region gloss (arithmetic mean of gloss values of the second region) obtained for all 6 replicates and report to the nearest 1 GU. The absolute difference between the first region gloss (first gloss) and second region gloss (second gloss), reported as a non-negative number, is reported as ΔGloss.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. A patterned fibrous substrate comprising a plurality of individual fibers, a first region, and a second region;

wherein the plurality of individual fibers comprise a functional surface additive;

wherein a plurality of individual fibers of the first region have a first diameter according to the Fiber Diameter Test Method, wherein a plurality of individual fibers of the second region have a second diameter according to the Fiber Diameter Test Method, and wherein the first diameter is less than the second diameter;

wherein the plurality of the individual fibers of the first region have a first shape, wherein the first shape is substantially circular;

wherein the plurality of the individual fibers of the second region have a second shape, wherein the second shape is different from the first shape, and wherein the second shape is substantially flat;

wherein the first region has a first C.I.E. L* score, according to the Color Test Method;

wherein the second region has a second C.I.E. L* score, according to the Color Test Method;

and wherein the first C.I.E. L* score is different than the second C.I.E. L* score.

2. The patterned fibrous substrate of claim 1, further comprising a plurality of primary bonds disposed in the first region and the second region.

3. The patterned fibrous substrate of claim 2, wherein the patterned fibrous substrate is free of bonds other than the plurality of primary bonds.

4. The patterned fibrous substrate of claim 1, wherein the patterned fibrous substrate is formed from a single nonwoven web.

5. The patterned fibrous substrate of claim 1, wherein the patterned fibrous substrate consists of a single fiber type.

6. The patterned fibrous substrate of claim 1, wherein the first region does not overlap the second region.

7. The patterned fibrous substrate of claim 1, further comprising a plurality of primary bonds disposed in the first region and the second region, wherein the plurality of fibers of the fibrous substrate are substantially unattached outside of the plurality of primary bonds.

8. The patterned fibrous substrate of claim 1, wherein the functional surface additive is selected from a melt additive or a topical additive.

9. The patterned fibrous substrate of claim 1, wherein the functional surface additive is selected from the group of: fatty amides, monoglycerides, diglycerides, triglycerides, silicones and copolymers thereof, fatty alcohols, fatty acids, fatty acid esters, polyolefin copolymers, and combinations thereof.

10. The patterned fibrous substrate of claim 1, wherein the functional surface additive comprises erucamide.

11. The patterned fibrous substrate of claim 1, wherein the functional surface additive comprises glyceryl tristearate.

12. The patterned fibrous substrate of claim 1, wherein the functional surface additive comprises a silicone-containing compound.

13. The patterned fibrous substrate of claim 1, wherein an absolute difference between the first C.I.E. L* score and the second C.I.E. L* score (ΔL*) is greater than 4.

14. The patterned fibrous substrate of claim 1, wherein the individual fibers comprise mono-component polypropylene fibers.

15. The patterned fibrous substrate of claim 1, wherein the individual fibers comprise bi-component fibers having a sheath/core structure, wherein a sheath of the fibers comprises polyethylene, and wherein a core of the fibers comprises polypropylene and/or polyester.

16. The patterned fibrous substrate of claim 1, wherein the first region has a first opacity, according to the Opacity Test Method, wherein the second region has a second opacity, according to the Opacity Test Method, and wherein the first opacity is different than the second opacity.

17. The patterned fibrous substrate of claim 16, wherein a difference between the first opacity and the second opacity is between about 5% and about 60%, according to the Opacity Test Method.

18. The patterned fibrous substrate of claim 1, wherein the first region has a first region fluid permeability score (PS1), according to the Fluid Permeability Test Method;

wherein the second region has a second region fluid permeability score (PS2), according to the Fluid Permeability Test Method;

wherein the first region fluid permeability score (PS1) is different than the second region fluid permeability score (PS2).

19. The patterned fibrous substrate of claim 18, wherein the first region fluid permeability score (PS1) and the second region fluid permeability score (PS2) are both greater than 5 Darcy, according to the Fluid Permeability Test Method.

20. An absorbent article comprising the patterned fibrous substrate of claim 1, wherein the patterned fibrous substrate forms at least a portion of one of: an outer cover, a topsheet, a front ear, a back ear, a front belt, a back belt, a waistband, and a fastener landing zone.

21. A laminate comprising the patterned fibrous substrate of claim 1, wherein the laminate comprises a second substrate, wherein a portion of the second substrate has a second substrate C.I.E. L* score, according to the Color Test Method; and wherein the first C.I.E. L* score is greater than the second substrate C.I.E. L* score.

22. The laminate of claim 21, wherein the second substrate is a film.

* * * * *